United States Patent
Turner et al.

(10) Patent No.: US 10,352,884 B2
(45) Date of Patent: Jul. 16, 2019

(54) OPERATIONAL CONSTRAINT OPTIMIZATION APPARATUSES, METHODS AND SYSTEMS

(71) Applicant: Schneider Electric USA, Inc., Andover, MA (US)

(72) Inventors: Larry A. Turner, Cary, NC (US); Paul Robert Buda, Raleigh, NC (US); Scott Robert Brown, Wake Forest, NC (US); Gary Brent Pollard, Wendell, NC (US); David R. Glasgow, Wendell, NC (US)

(73) Assignee: Schneider Electric USA, Inc., Andover, MA (US)

( * ) Notice: Subject to any disclaimer, the term of this patent is extended or adjusted under 35 U.S.C. 154(b) by 379 days.

(21) Appl. No.: 14/956,019

(22) Filed: Dec. 1, 2015

(65) Prior Publication Data

US 2016/0223214 A1    Aug. 4, 2016

Related U.S. Application Data

(60) Provisional application No. 62/110,379, filed on Jan. 30, 2015, provisional application No. 62/110,398, (Continued)

(51) Int. Cl.
*G01N 25/18* (2006.01)
*G05B 13/02* (2006.01)
(Continued)

(52) U.S. Cl.
CPC .............. *G01N 25/18* (2013.01); *F24F 11/30* (2018.01); *F24F 11/62* (2018.01); *G05B 13/021* (2013.01);
(Continued)

(58) Field of Classification Search
None
See application file for complete search history.

(56) References Cited

U.S. PATENT DOCUMENTS 4,475,685 A   10/1984  Grimado
5,115,967 A    5/1992  Wedekind
(Continued)

FOREIGN PATENT DOCUMENTS

EP       0246443 A1   11/1987
EP        089893 A1    1/1999
(Continued)

OTHER PUBLICATIONS

International Preliminary Examination, Written Opinion and Search Report for PCT/US2016/015745 dated Mar. 31, 2016.
(Continued)

*Primary Examiner* — Ziaul Karim
*Assistant Examiner* — Saad M Kabir
(74) *Attorney, Agent, or Firm* — Locke Lord LLP

(57) ABSTRACT

A system for comfort based management of thermal systems, including residential and commercial buildings with active cooling and/or heating, is described. The system can operate without commissioning information, and with minimal occupant interactions, and can learn heat transfer and thermal comfort characteristics of the thermal systems so as to control the temperature thereof while minimizing energy consumption and maintaining comfort.

25 Claims, 22 Drawing Sheets

Related U.S. Application Data filed on Jan. 30, 2015, provisional application No. 62/110,344, filed on Jan. 30, 2015, provisional application No. 62/110,393, filed on Jan. 30, 2015, provisional application No. 62/110,386, filed on Jan. 30, 2015.

(51) Int. Cl.

| | | |
|---|---|---|
| *G05D 23/19* | (2006.01) | |
| *G05B 15/02* | (2006.01) | |
| *F24F 11/30* | (2018.01) | |
| *F24F 11/62* | (2018.01) | |
| *F24F 110/10* | (2018.01) | |
| *F24F 110/20* | (2018.01) | |
| *F24F 140/60* | (2018.01) | |
| *F24F 130/00* | (2018.01) | |
| *F24F 130/10* | (2018.01) | |
| *F24F 11/63* | (2018.01) | |
| *F24F 11/58* | (2018.01) | |

(52) U.S. Cl.
CPC ......... *G05B 15/02* (2013.01); *G05D 23/1917* (2013.01); *F24F 11/58* (2018.01); *F24F 11/63* (2018.01); *F24F 2110/10* (2018.01); *F24F 2110/20* (2018.01); *F24F 2130/00* (2018.01); *F24F 2130/10* (2018.01); *F24F 2140/60* (2018.01); *G05B 2219/2642* (2013.01)

(56) References Cited

U.S. PATENT DOCUMENTS

| | | |
|---|---|---|
| 6,478,233 B1 | 11/2002 | Shah |
| 7,130,719 B2 | 10/2006 | Ehlers |
| 8,352,082 B2 | 1/2013 | Parker |
| 8,584,030 B2 | 11/2013 | Laycock et al. |
| 2003/0217143 A1 | 11/2003 | Dudley |
| 2004/0262409 A1 | 12/2004 | Crippen et al. |
| 2007/0191987 A1 | 8/2007 | Dang et al. |
| 2009/0065596 A1 | 3/2009 | Seem et al. |
| 2010/0262298 A1 | 10/2010 | Johnson et al. |
| 2011/0160913 A1 | 6/2011 | Parker |
| 2012/0259469 A1 | 10/2012 | Ward et al. |
| 2013/0085616 A1* | 4/2013 | Wenzel ............... H02J 3/14 700/278 |
| 2014/0222221 A1 | 8/2014 | Boll et al. |
| 2014/0277765 A1 | 8/2014 | Boll et al. |
| 2014/0358291 A1 | 12/2014 | Wells |

FOREIGN PATENT DOCUMENTS

| | | |
|---|---|---|
| EP | 1139035 A2 | 10/2001 |
| WO | WO2002054165 A2 | 7/2002 |

OTHER PUBLICATIONS

International Preliminary Examination, Written Opinion and Search Report for PCT/US2016/015748 dated May 23, 2016.

European Search Opinion and Search Report for EP 16153477 dated Nov. 15, 2016.

Karer G. et al: "Predictive Control of Temperature in a Batch Reactor with Discrete Inputs," Intelligent Control, 2005. Proceedings of the 2005 IEEE International Symposium on, Mediterrean Conference on Control and Automation Limassol, Cyprus Jun. 27-29, 2005, Piscataway, NJ, USA, IEEE, Jun. 27, 2005 (Jun. 27, 2005), pp. 855-860, XP010817135. The entire document.

European Search Report and Written Opinion for EP Application No. EP 16 74 4214 dated completed Sep. 5, 2018.

* cited by examiner

Example: A UML class diagram illustrating the structure of compare and automate classes.

Example: An UML object diagram illustrating the structure and interactions of an exemplary thermal device object for a zone.

Example: A UML object diagram illustrating a structure and interactions of a thermal model object for a zone.

Example: A block diagram illustrating the structure of a thermal system, or site, comprising two zones and a surrounding environment, depicting heat flow into a zone.

Example: A graph illustrating a thermal model coefficient sequence for a zone.

Example: A graph illustrating a thermal temperature estimation sequence for a zone.

Example: A thermal model forward temperature estimation error sequence for an exemplary zone.

Example: A UML object diagram illustrating a structure and interactions of an exemplary weather model object for a site.

Example: A UML class diagram illustrating the structure of a filter, polynomial filter, and rate filter classes.

Example: An graph illustrating a weather model temperature estimation sequence for an exemplary site.

Example: A UML object diagram illustrating a structure and interactions of an exemplary comfort model object a zone.

Example: A graph illustrating a comfort model temperature profile with a plus event, and a plus event, occurring in active heating, over the course of one day, illustrating event response for an exemplary zone.

Example: A graph illustrating a comfort model temperature profile with a plus events, and a plus event, occuring in active heating, over the course of one day, illustrating reference recovery for an exemplary zone.

Example: A UML object diagram illustrating a structure and interactions of an exemplary comfort agent object for a site.

Example: a UML sequence diagram illustrating an update event of a comfort agent object for a site.

Example: Generation of a plurality of commands to optimally control an environment according to one or more constraints.

Example: A graph illustrating a comfort agent effective temperature, optimization temperature, and control temperature sequence for a site.

Example: A graph illustrating comfort agent 300 optimization energy for a site.

OPERATIONAL CONSTRAINT OPTIMIZATION APPARATUSES, METHODS AND SYSTEMS

This application claims the benefit of each of the following applications: (a) U.S. Provisional Application No. 62/110,393, filed Jan. 30, 2015 and titled "Interior Comfort HVAC User-Feedback Control System and Apparatus"; (b) U.S. Provisional Application Ser. No. 62/110,344, filed Jan. 30, 2015 and titled "Interior User-Comfort Energy Efficiency Modeling and Control Systems and Apparatuses"; (c) U.S. Provisional Application Ser. No. 62/110,386, filed Jan. 30, 2015 and titled "Interior Volume Thermal Modeling and Control Apparatuses, Methods and Systems"; (d) U.S. Provisional Application Ser. No. 62/110,398, filed Jan. 30, 2015 and titled "Apparatuses, Methods and Systems for Comfort and Energy Efficiency Conformance in an HVAC System"; and (e) U.S. Provisional Application Ser. No. 62/110,379, filed Jan. 30, 2015 and titled "Operational Constraint Optimization Apparatuses, Methods and Systems"; the entire contents of each of the aforementioned applications are herein expressly incorporated by reference.

This application may contain material that is subject to copyright, mask work, and/or other intellectual property protection. The respective owners of such intellectual property have no objection to the facsimile reproduction of the disclosure by anyone as it appears in published Patent Office file/records, but otherwise reserve all rights.

RELATED APPLICATIONS

This application is related to and hereby incorporates the following applications by reference:

U.S. application Ser. No. 14/956,082, filed Dec. 1, 2015 and titled "Interior Comfort HVAC User-Feedback Control System and Apparatus,"

U.S. application Ser. No. 14/956,227, filed Dec. 1, 2015 and titled "Interior User-Comfort Energy Efficiency Modeling and Control Systems and Apparatuses,"

U.S. application Ser. No. 14/955,971, filed Dec. 1, 2015 and titled "Interior Volume Thermal Modeling and Control Apparatuses, Methods and Systems," and U.S. application Ser. No. 14/956,139, filed Dec. 1, 2015 and titled "Apparatuses, Methods and Systems for Comfort and Energy Efficiency Conformance in an HVAC System";

the entire contents of each of the aforementioned applications are herein expressly incorporated by reference.

BACKGROUND

Users like to interact with intelligent devices which can operate efficiently according to their needs and preferences. Intelligent systems can be aware of current changes in the environment that may eventually affect their goals and plan accordingly to procure a successful outcome.

BRIEF DESCRIPTIONS OF THE DRAWINGS

Figure 1:
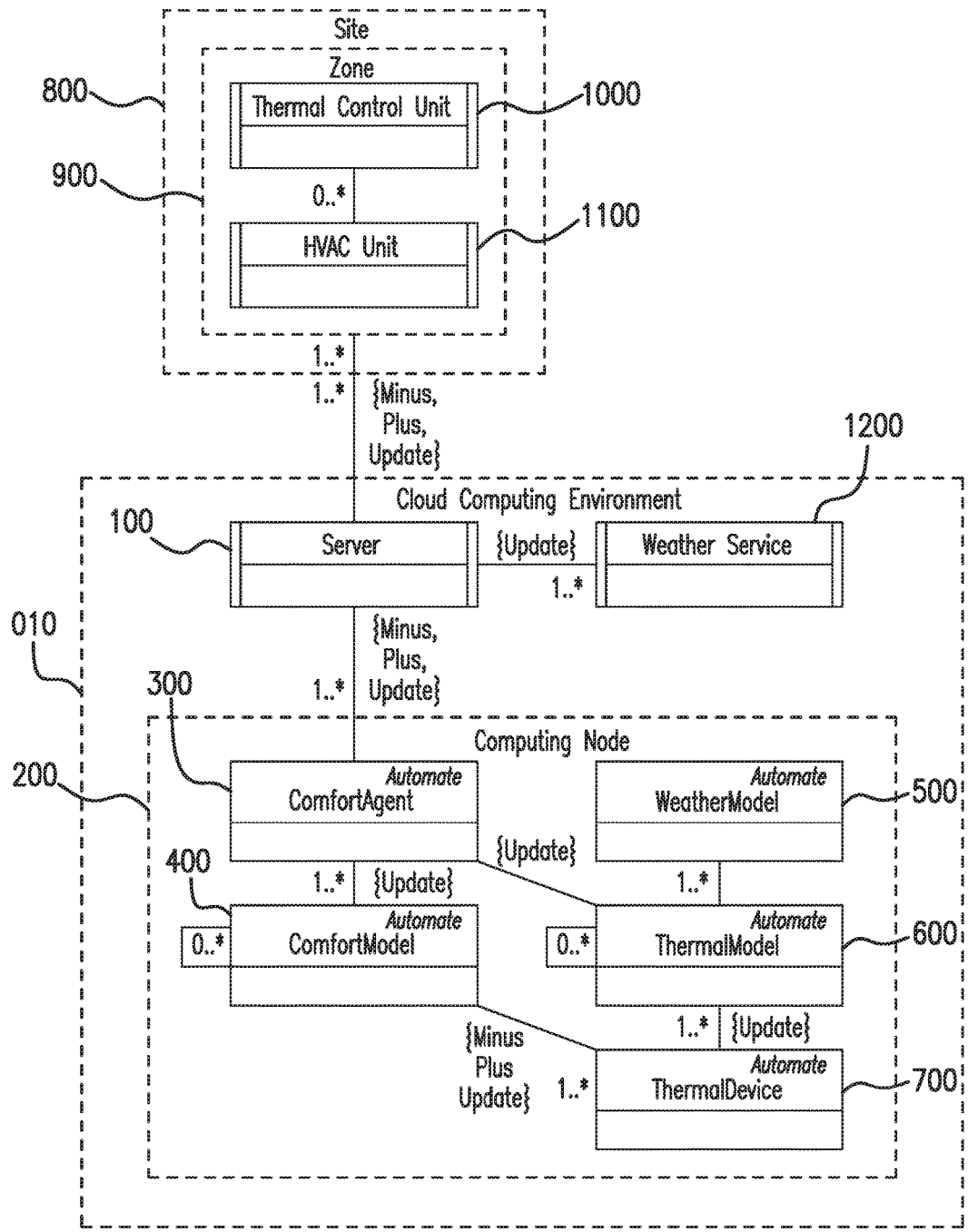
FIG. 1 shows an example of a UML object diagram of a system architecture of an apparatus to facilitate comfort based thermal management to one or more sites, in one embodiment.

While the present disclosure contemplates various modifications and alternative forms, specific embodiments have been shown by way of example in the drawings and will be described in detail herein. It should be understood, however, that the disclosure is not intended to be limited to the particular forms disclosed. Rather, the invention covers all modifications, equivalents, and alternatives falling within the spirit and scope of the invention as claims set forth herein. Subject matter disclosed, for example, in the Abstract, Summary, and Detailed Description sections, but not explicitly set forth in the claims, should not be incorporated into the claims, singly or collectively, by implication, inference or otherwise.

DETAILED DESCRIPTION

In some embodiments, OPERATIONAL CONSTRAINT OPTIMIZATION APPARATUSES, METHODS AND SYSTEMS (hereinafter "OCO") can learn from a set of weather estimations and thermal properties to predict energy consumption, power consumption and/or temperatures associated to one or more volumes or enclosed environments.

Comfort Agent

In some embodiments, a processor-implemented method for adaptive temperature control of a thermal system comprises receiving, at a comfort agent system, one or more thermal device properties associated with one or more volumes of the thermal system. A root state is determined, the root state associated with a first temperature vector comprising a plurality of temperature values associated with the one or more volumes of the thermal system. One or more constraint properties are determined, to define a multi-dimensional space that includes a plurality of states, each state of the plurality of states being associated with a respective further temperature vector, and each said further temperature vector originating with the root state and extending over a duration of time. The plurality of states, and a plurality of transitions each associated with a state of the plurality of states, are calculated. An optimal path is selected, which comprises one or more of the plurality of states and one or more of the plurality of transitions, and the optimal path: (1) originates with the root state; (2) defines a contiguous sequence of the one or more of the plurality of states; and (3) minimizes a cost function. One or more control temperature vectors are calculated, each comprising a plurality of control temperature values associated with the one or more volumes of the thermal system, as a function including at least one of: the one or more constraint properties, and the one or more further temperature vectors associated with the one or more of the plurality of states of the optimal path. The one or more control temperature vectors can be communicated to one or more thermal control units of the one or more volumes of the thermal system, to regulate temperature during an active cooling mode and/or an active heating mode of the thermal control unit.

In some embodiments, a processor-implemented method for adaptive temperature control of a thermal system comprises receiving, at a processor, one or more thermal device properties associated with one or more volumes of a thermal system, and determining a root state associated with a first temperature vector comprising a plurality of temperature values associated with the one or more volumes of the thermal system. One or more constraint properties are determined, including one or more effective temperature vectors, the one or more constraint properties defining a multi-dimensional space having a plurality of states, each state of the plurality of states being associated with a respective further temperature vector, each said further temperature vector originating with the root state and extending over a duration of time. The plurality of states and a plurality of transitions are calculated, each associated with a state of the plurality of states, wherein each state of the plurality of states is associated with a state value vector comprising a plurality of state values that represent the value of being in a specific state, and each transition of the plurality of transitions is associated with an action value vector comprising a plurality of action values that represent the immediate cost of transitioning from the specific state to a child state, the plurality of states including the root state and extending over the duration of time, in the defined multi-dimensional space An optimal path is selected, comprising one or more of the plurality of states and one or more of the plurality of transitions, thereby defining a contiguous sequence having one or more states and one or more transitions, the sequence originating with the root state and extending over the duration of time, each transition being selected to minimize a vector norm of the state value vector associated with one or more child states. One or more control temperature vectors are calculated, comprising a plurality of control temperature values associated with the one or more volumes of the thermal system, as a function to include at least one of: the one or more constraint properties, and the one or more further temperature vectors associated with the one or more of the plurality of states of the optimal path. The one or more control temperature vectors are communicated to one or more thermal control units of the one or more volumes of the thermal system, to regulate temperature during an active cooling mode and/or an active heating mode of the thermal control unit.

System

A system for comfort based management of thermal systems, including residential and commercial buildings with active cooling and/or heating, is described herein. In some embodiments, the system requires no commissioning information, requires minimal occupant interactions, and can learn the heat transfer characteristics of the thermal systems and the thermal comfort characteristics of the occupants, and control the temperature in a manner that minimizes energy consumption while maintaining occupant comfort.

In some embodiments, a thermal model 600 is a representation of the thermal behavior of a volume in a thermal system, which characterizes heat transfer, and estimates energy consumption and temperature. A thermal system can be generalized as a collection of interdependent volumes and boundaries and a surrounding environment, whose behavior is described by the transfer of mass, work, and heat across the boundaries. A thermal system is defined as a site 800, and each volume, a contiguous region of uniform thermal control, is defined as a zone 900.

In some embodiments, a weather model 500 is a representation of a weather service 1200, which defines forecast estimations of properties which are relevant in a specific region of interest which includes the surrounding environment of a site 800.

In some embodiments, a comfort model 400 is a representation of the thermal comfort in a zone 900. The comfort model 400 can estimate the effective temperature at which an occupant is unlikely to object, for example thereby maintaining occupant comfort, while minimizing energy consumption due to active cooling and/or heating. The comfort model can learn multiple independent temperature profiles through observation of the temperature (e.g., of a zone), and through occupant interactions, which indicate a preference to lower or raise the temperature.

In some embodiments, a comfort agent 300 interacts with one or more thermal models 600 to estimate physically realizable discrete temperature states with associated transition values, constrained by comfort model 400 effective temperature estimates, to identify an optimal path and define control temperatures for each zone 900 in a site 800, facilitating optimal start and deterministic temperature control.

System Architecture

Unified Modeling Language ("UML") is a standard recognized by the International Organization for Standardization ("ISO") consisting of semantics to visualize the architecture and behaviors of object-oriented designs. UML is employed to define simplified object and class diagrams corresponding to an exemplary reference design.

International System of Units ("SI") is a nearly universal standard for representing a system of measurements. SI units, and associated common unit abbreviations, are exclusively employed in an exemplary reference design, as a matter of convenience.

With reference to FIG. 1, a system for comfort based thermal management consists of a cloud computing environment 010, which includes one or more servers 100 and one or more computing nodes 200, and interacts with one or more weather services 1200, and one or more sites 800.

A cloud computing environment 010 is a system supporting scalable distributed computing and storage, which allows multiple computing nodes 200 to exchange information with servers 100. Scalability is achieved through flexible resource allocation, often virtualizing servers 100 and computing nodes 200 which are abstracted from the physical hardware on which they reside. Resources can be dynamically allocated and disposed on demand, abstracting infrastructure complexity from computing nodes 200.

A server 100 manages computational and storage resource allocation and disposal, facilitates data transport and synchronization, and interacts with one or more weather services 1200, one or more sites 800, and one or more computing nodes 200.

A weather service 1200 provides forecast estimations of weather conditions which are relevant in a specific region of interest which includes the surrounding environment of a site 800, and interacts with a server 100.

A site 800 contains one or more zones 900. Each zone 900 contains one or more thermal control units 1000, which interact with a server 100 and zero or more HVAC units 1100.

A computing node 200 defines a collection of entities which implement the analysis and control capabilities defining comfort based thermal management of one or more sites 800, and interacts with a server 100.

For each supported site 800, a computing node 200 defines one or more thermal devices 700 for each zone 900, one comfort model 400 for each zone 900, one thermal model 600 for each zone 900, one weather model 500, and one comfort agent 300.

A thermal device 700 interacts with a server 100 to indirectly exchange information with a thermal control unit 1000 in a zone 900.

A thermal model 600 observes one or more thermal devices 700, interacts with zero or more thermal models 600 associated with a site 800, and observes a weather model 500.

A weather model 500 interacts with a server 100 to indirectly exchange information with a weather service 1200.

A comfort model 400 observes one or more thermal devices 700, and interacts with zero or more comfort models 400 associated with a site 800.

A comfort agent 300 interacts with a server 100, and observes one or more comfort models 400, and one or more thermal models 600 associated with a site 800.

Automate

Figure 2:
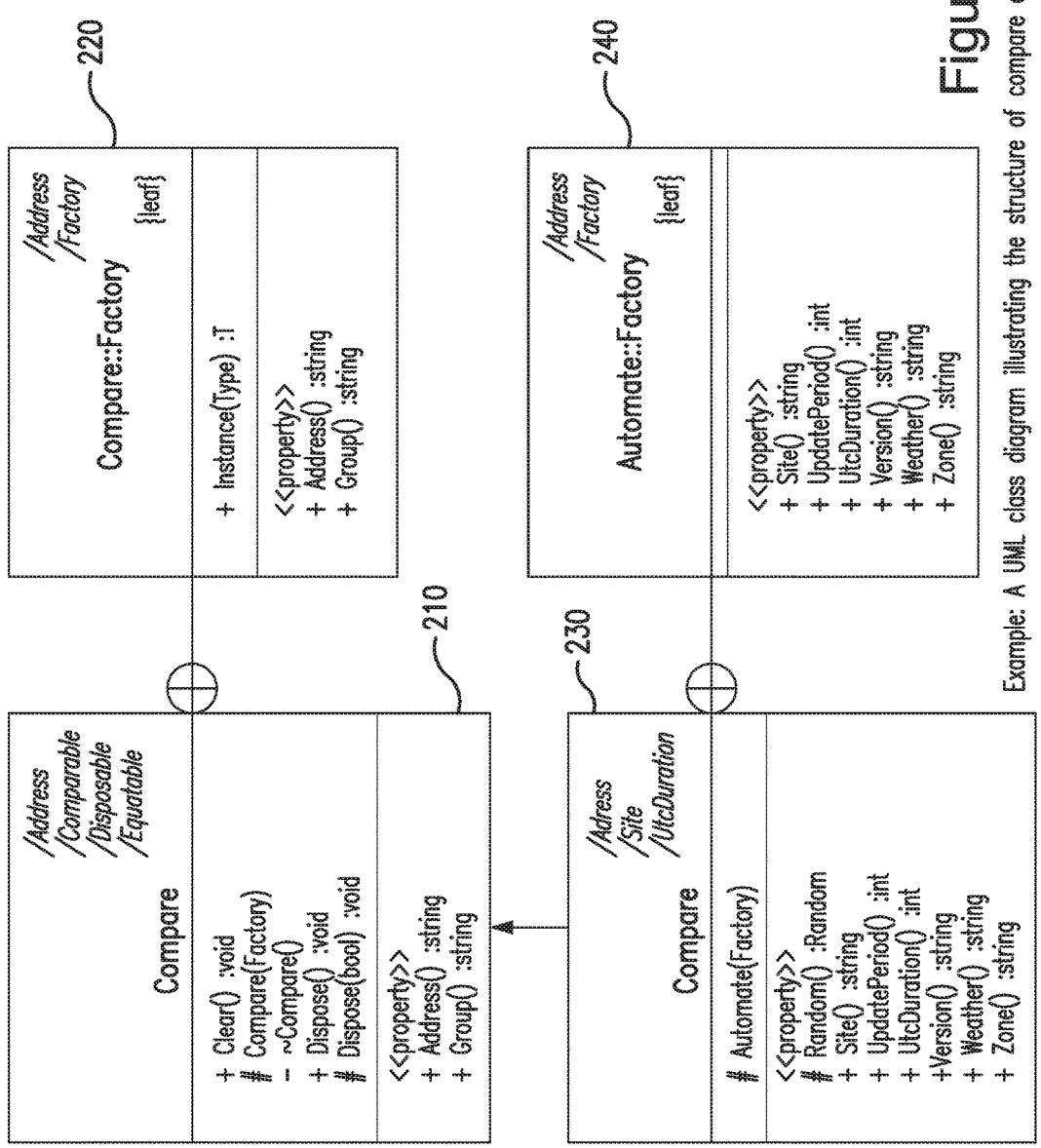
FIG. 2 shows a UML class diagram illustrating the structure of compare and automate classes, in one embodiment.

With reference to FIG. 2, compare 210 is an abstract class which defines properties commonly associated with similar derived classes, facilitating unique addressing and comparison. A compare 210 class defines properties including a unique address and a group. A compare factory 220 is a class which provides a means to construct or retrieve instances of derived concrete types.

Automate 230 is an abstract class which defines properties commonly associated with similar derived classes, facilitating automation, control, and diagnostics applications. An automate 230 class defines properties including a site 800, Universal Time Coordinated ("UTC") duration, weather, and zone 900. An automate factory 240 is a class which provides a means to construct or retrieve instances of derived concrete types.

The address property is a unique identifier which represents an instance, independent of the concrete class type.

The group property is an identifier which represents of the name of a specific concrete class type.

The site 800 property is an identifier which represents the geographic location of a specific thermal system, consisting of one or more zones 900 with active cooling and/or heating.

The update period property is the time interval of an update operation, nominally 10 minutes, in units of s.

The UTC duration property is the local time offset relative to UTC+0, in units of s, including any requisite compensation for daylight savings time, at a specific site 800.

The weather property is an identifier which represents a weather service 1200 associated with a specific geographical region.

The zone 900 property is an identifier which represents a thermal volume, or contiguous region of uniform thermal control, or active cooling and/or heating.

The automate factory 240 instance method constructs or retrieves an object of a concrete type derived from automate 230. A factory design pattern is employed to allow the specific instance properties to be defined prior to instantiation, and ensure property definitions are sufficient and valid immediately prior to object instantiation or retrieval.

Thermal Device

A thermal device 700 is a convenient representation of a specific thermal control unit 1000, a component of a thermal system which observes and controls the temperature of a volume of a thermal system. A thermal system can be generalized as a collection of interdependent volumes and boundaries and a surrounding environment. A thermal system is defined as a site 800, and each volume, a contiguous region of uniform thermal control, is defined as a zone 900.

A thermal control unit 1000 controls zero or more HVAC units 1100, and can regulate the temperature in a zone 900 according to a control temperature, abstracting the details of the internal behavior of HVAC units 1100 with which it interacts. Multiple thermal control units 1000 can be electively utilized in a zone 900 to compensate for volumetric variance in thermal properties, or to ensure redundancy and improve fault tolerance, though only one thermal control unit 1000 in a zone 900 is required.

A thermal control unit 1000 can support active cooling and/or heating. Active cooling employs a cooling type HVAC unit 1100, e.g., including an air conditioner, refrigerator, or freezer, to cool a zone 900, while active heating employs a heating type HVAC unit 1100, e.g., including a furnace, heat pump, resistive heating, or electric or hydronic radiant heating, to heat a zone 900. An HVAC unit 1100 may comprise any device capable of controlling temperature, by producing, consuming, or transferring heat, in a zone 900. Active cooling and heating are mutually exclusive at a specific time.

A thermal control unit 1000 can support occupant interactions, which indicate a preference to lower or raise the temperature, resulting in the synthesis of minus and plus events, respectively. A thermal control unit 1000 can provide an immediate and transient response to increase the thermal comfort of an occupant in response to occupant interactions, by lowering or raising the temperature by a temperature offset over a finite duration.

Thermal Device Architecture

Figure 3:
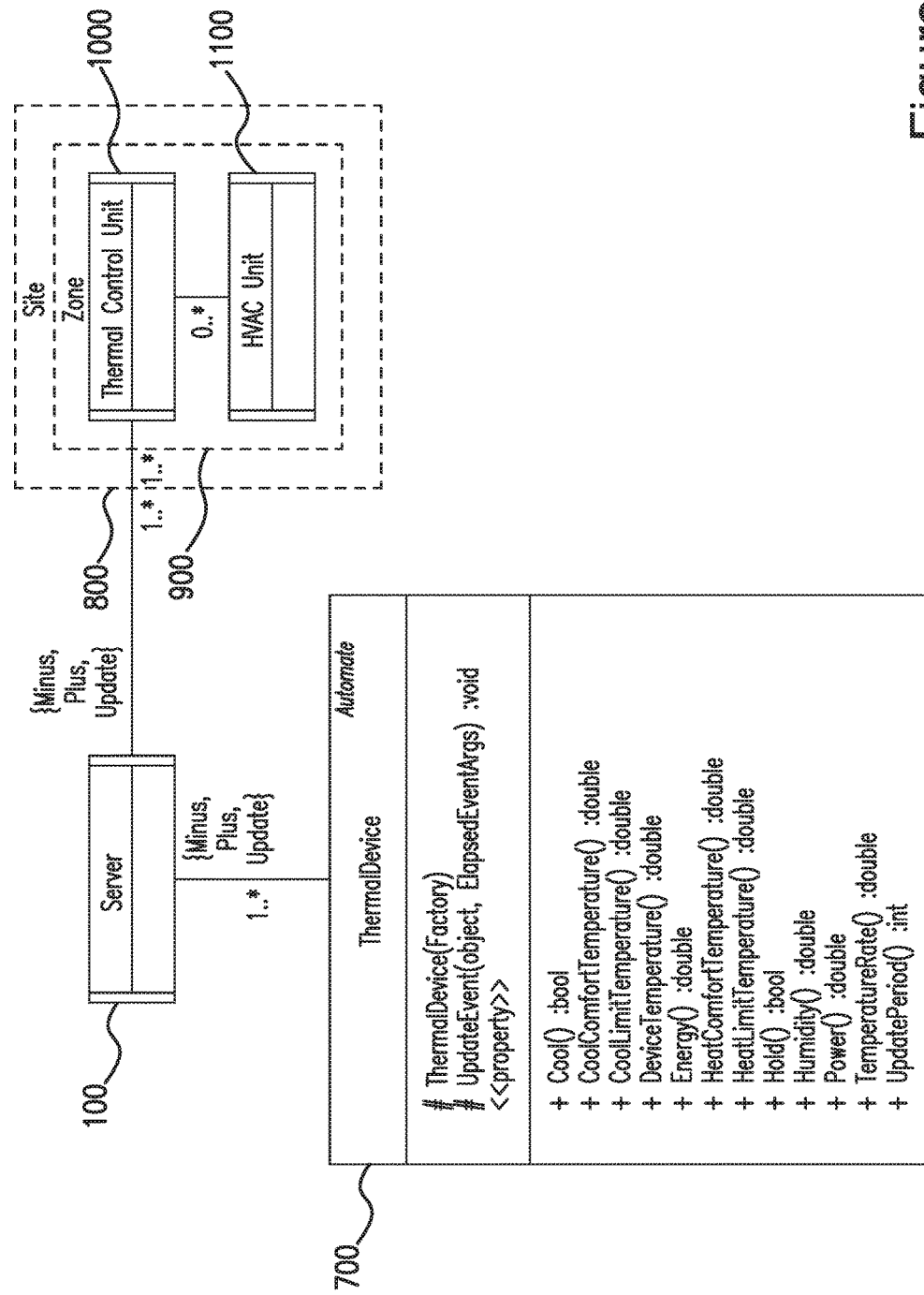
FIG. 3 shows a UML object diagram illustrating the structure and interactions of an exemplary thermal device object for a zone, in one embodiment.

With reference to FIG. 3, a site 800 contains one or more zones 900. Each zone 900 contains one or more thermal control units 1000, which interact with a server 100 and zero or more HVAC units 1100.

A thermal device 700 interacts with a server 100 to indirectly exchange information with a thermal control unit 1000 in a zone 900.

In some embodiments, a thermal device 700 defines properties, including cool, device temperature, energy consumed in active cooling or heating, hold, power capacity, and temperature rate, associated with a specific zone 900, based on observations of conditions. Occupant interactions with a thermal control unit 1000 can indicate a preference to lower or raise the temperature.

In some embodiments, a thermal device 700 defines events, for example to provide observer notifications, including minus, plus, and update. Minus or plus events are signaled when an occupant indicates a desire to lower or raise the temperature, respectively. Update events are signaled during each update period, when a thermal device 700 update is complete.

A thermal device 700 calculates and defines the active cooling or heating state of a zone 900 as a function of the device temperature. Active cooling employs a cooling type HVAC unit 1100 to cool a zone 900, while active heating employs a heating type HVAC unit 1100 to heat a zone 900. Active cooling is indicated above the cool comfort temperature, active heating is indicated below the heat comfort temperature, and the transition between active cooling and heating is defined by hysteresis as a function of device temperature, cool comfort temperature and heat comfort temperature.

The cool property is evaluated in each update period to indicate active cooling selection, applying hysteresis between a cool comfort temperature and a heat comfort temperature. The cool property is true if the device temperature is greater than or equal to the cool comfort temperature, or if the cool property value from the previous evaluation is true and the device temperature is greater than the heat comfort temperature.

The cool comfort temperature and heat comfort temperature properties define the control temperatures which maximize energy consumption, or the minimum and maximum supported control temperatures, in active cooling and heating, respectively, in units of ° C. The range of temperatures between the cool comfort temperature and heat comfort temperature of a zone 900 form a comfort band in which the occupant is implicitly comfortable.

The cool limit temperature and heat limit temperature properties define the control temperatures which minimize energy consumption, or the maximum and minimum supported control temperatures, in active cooling and heating, respectively, in units of ° C. Temperatures outside of this range can be observed, due the system inactivity or capacity limitations in active cooling or heating relative to environmental conditions, though temperature control outside of this range can be restricted.

The device temperature property is the temperature observed in a zone 900, in units of ° C.

In some embodiments, the energy property is the energy consumed during the most recent update period. The energy property can be the energy consumed in active cooling or heating, in units of J or normalized to unity range. In some embodiments, any representation which correlates with the energy consumed by an HVAC unit is a suitable representation of the energy property, including observations or estimates calculated as a function of energy, power, current, relay state, time, and/or duty cycle, in any units or range.

The hold property indicates an occupant preference for manual thermal control.

The humidity property is the humidity observed in a zone 900, normalized to unity range.

In some embodiments, the power property is the power capacity available for consumption for active cooling or heating in an HVAC unit 1100, in units of W or normalized to unity range. In some embodiments, any representation which correlates with the power capacity available for consumption by an HVAC unit is a suitable representation of the power property, including observations or estimates calculated as a function of energy, power, current, relay state, time, and/or duty cycle, in any units or range. Power can be initially unknown, and dynamically estimated for each cool state, by retaining the maximum observed average power.

The temperature rate property is the rate of change of device temperature with respect to the time interval of the most recent update period, in units of ° C./s.

The update period property is the time interval of a thermal device 700 update, which corresponds to the interval at which thermal device 700 properties are modified, nominally 10 minutes, in units of s.

Thermal Model

A thermal model 600 is a representation of the thermal behavior of a volume in a thermal system, which characterizes heat transfer, and estimates energy consumption and temperature. A thermal system can be generalized as a collection of interdependent volumes and boundaries and a surrounding environment, whose behavior is described by the transfer of mass, work, and heat across the boundaries. A thermal system is defined as a site 800, and each volume therein, being a contiguous region of uniform thermal control, is defined as a zone 900.

Open, or "permeable," and mechanically-isolated thermal systems do not support deformation in volumes, and associated work transfer, or mass transfer across boundaries. The behavior of an open, mechanically-isolated thermal system can therefore generally be defined by heat transfer. As such, in some embodiments, a thermal system can be conveniently described as open and mechanically isolated, if the system does not support deformation and/or if the mass within a volume is quasi-stationary, or changes slowly relative to the rate of heat transfer (e.g., where heat conduction within a volume is much faster than heat transfer across a boundary).

Simple transient conduction, associated with a lumped capacitance model, implies that pressure and temperature are substantially uniform within a volume, though not necessarily across a boundary. In some embodiments, a thermal system can employ simple transient conduction to simplify analysis by neglecting temperature and pressure gradients within a volume by assuming that heat is conducted within a volume much faster than heat transfer across a boundary. Simple transient conduction can be a convenient approach, for example, when there are constraints on the spatial and temporal resolution at which temperature and pressure within a volume can be practically observed, to reduce computational complexity, and/or to improve utility. The thermal model 600 described herein, according to some embodiments, is suitable for application in an open, mechanically-isolated thermal system, having behavior consistent with simple transient conduction, and where the thermal system consists of a collection of one or more zones 900 and boundaries, and a surrounding environment.

Thermal Model Architecture

Figure 4:
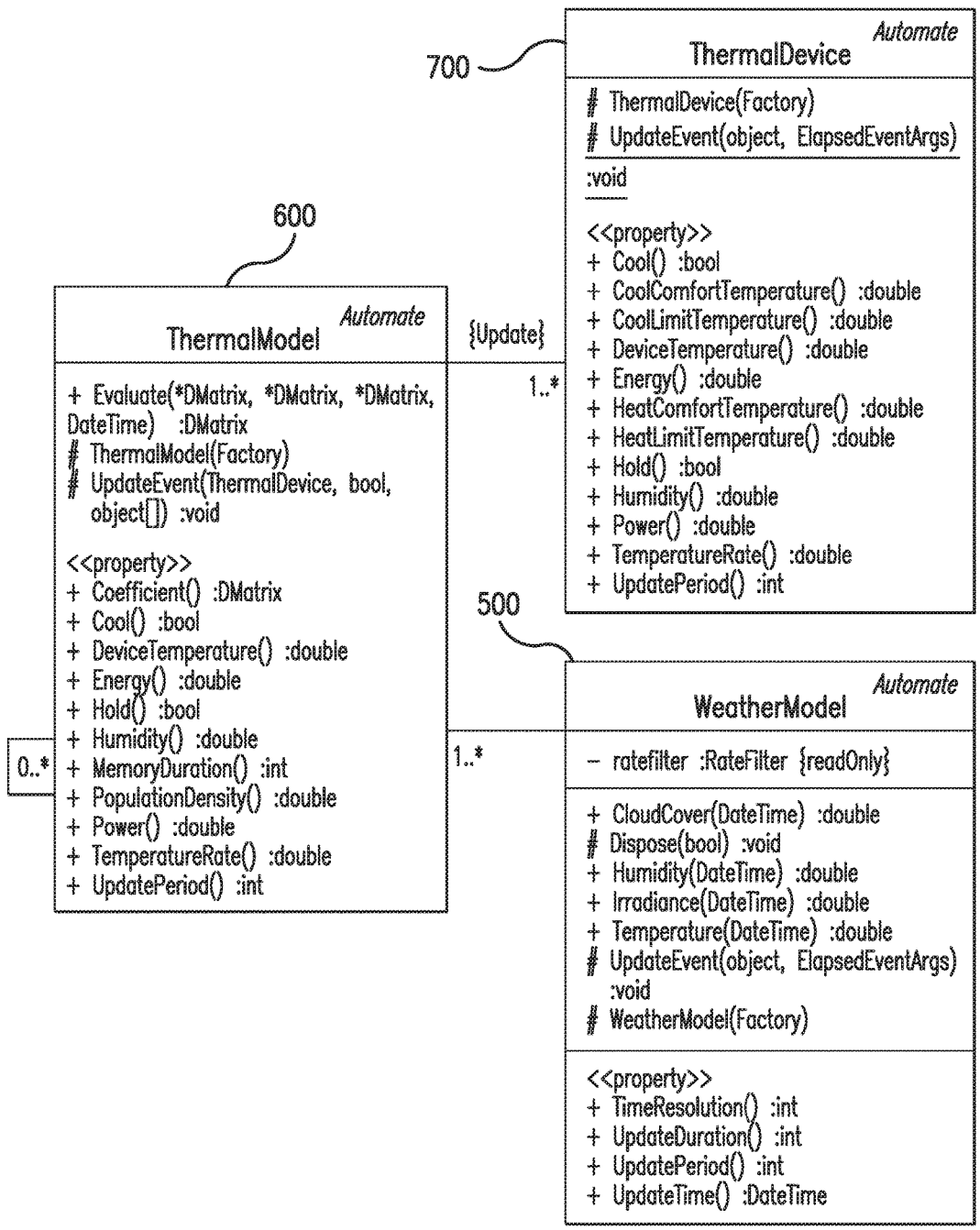
FIG. 4 shows a UML object diagram illustrating a structure and interactions of a thermal model object for a zone, in one embodiment.

With reference to FIG. 4, in some embodiments a thermal model 600 observes one or more thermal devices 700, interacts with zero or more further thermal models 600 associated with a site 800, and/or observes a weather model 500. The thermal model 600 can update properties and events at an update period. The thermal model 600 can aggregate thermal device 700 properties and/or events associated with a zone 900 having one or more thermal devices 700 associated therewith. The aggregation of thermal device 700 properties and/or events may include filtering, integration, and/or selection, as appropriate, to form a unified representation of thermal model 600 properties.

The thermal model 600 can interact with zero or more thermal models 600 associated with a site 800. Interaction between thermal models 600 associated with a site 800 can be necessary, for example, to facilitate thermal model 600 update and estimation efforts, as passive heat transfer across the boundary of a zone 900 can occur with respect to each zone 900 with a shared boundary.

The specific geometry of a thermal system can be unknown. In some embodiments, thermal model 600 can dynamically determine the effective connectivity of zones 900 in a site 800, and/or which connections are relevant to estimate passive heat transfer. A thermal model 600 can elect to ignore connectivity with a zone 900 that is determined to have negligible effect on heat transfer estimation. Eliminating weak connections can reduce thermal model 600 order and computational complexity, and can improve the numerical accuracy of the solution.

In some embodiments, inter-zone passive heat transfer can be ignored, negating the need for a thermal model 600 to interact with thermal models 600 associated with other zones 900 in a site 800, depending on the specific geometry, materials, and observed temperature differences at zone 900 boundaries. If the temperatures in zones sharing a boundary are consistently similar, the thermal system may not exhibit sufficient diversity to support robust estimation of inter-zone passive heat transfer.

In some embodiments, a weather model 500 provides a thermal model 600 with properties such as (but not limited to) cloud cover, humidity, solar irradiance, and temperature, related to the surrounding environment, (i.e., the volume exterior to the thermal system). In some embodiments, weather model 500 properties are available as forecast data associated with a date time value that extends over a weather duration, for example 24 hours, from the current time.

In some embodiments, a thermal model 600 observes thermal device 700 properties associated with a zone 900, observes weather model 500 properties, and relates the observed rate of temperature change to the estimated heat transfer. Heat transfer can be estimated as a function of inter-zone 900 temperature differences, energy consumed in active cooling or heating, cloud cover, solar irradiance, and/or the like. Forward and reverse energy and temperature estimation can also be performed by the thermal model 600.

In some embodiments, a thermal model 600 defines properties associated with a specific zone 900, such as (but not limited to): a coefficient property, a "cool" property, a cool comfort temperature property, a heat comfort temperature property, a cool limit temperature property, a heat limit temperature property, a device temperature property, an energy property, a hold property, a humidity property, a memory duration property, a population density property, a power property, a temperature rate property, and/or an update period property, each defined below. In some embodiments, a thermal model 600 defines events, for example to provide observer notifications, including update(s). Update events can be signaled or triggered during one or more update periods, and can occur, for example, when a thermal model 600 update is complete.

The coefficient property defines dynamic and order-specific thermal model 600 parameters relating passive, active, solar, and unobserved heat transfer rates, necessary to facilitate energy and temperature estimation.

The cool property indicates active cooling selection. The cool property is true if the device temperature is greater than or equal to the cool comfort temperature, or if the cool property value from the previous evaluation is true and the device temperature is greater than the heat comfort temperature.

The cool comfort temperature and heat comfort temperature properties define the control temperatures which maximize energy consumption, or the minimum and maximum supported control temperatures, in active cooling and heating, respectively, in units of ° C. The range of temperatures between the cool comfort temperature and heat comfort temperature of a zone 900 form a comfort band in which the occupant is implicitly comfortable.

The cool limit temperature and heat limit temperature properties can define the control temperatures which minimize energy consumption, or the maximum and minimum supported control temperatures, in active cooling and heating, respectively, in units of ° C. Temperatures outside of this range can be observed, due the system inactivity or capacity limitations in active cooling or heating relative to environmental conditions, though temperature control outside of this range can be restricted.

In some embodiments, the device temperature property is the temperature observed in a zone 900, in units of ° C.

In some embodiments, the energy property is the energy consumed during the most recent update period. The energy property is the energy consumed in active cooling or heating, in units of J or normalized to unity range. In some embodiments, any representation that correlates with the energy consumed by an HVAC unit is a suitable representation of the energy property, including observations or estimates calculated as a function of energy, power, current, relay state, time, and/or duty cycle, in any units or range.

The hold property indicates an occupant preference for manual thermal control.

The humidity property is the humidity observed in a zone 900, normalized to unity range.

The memory duration property is the contiguous window of time over which a thermal model 600 retains and considers observations necessary to solve thermal coefficients, nominally 10 days, in units of s.

The population density property is the minimum ratio of elements in a column of an incident matrix associated with a thermal model 600 with absolute values greater than a small positive value, nominally 0.025.

The power property is the power capacity available for consumption for active cooling or heating in an HVAC unit 1100, in units of W or normalized to unity range. Any representation that correlates with the power capacity available for consumption by an HVAC unit is a suitable representation of the power property, including observations or estimates calculated as a function of energy, power, current, relay state, time, and/or duty cycle, in any units or range. Power can be initially unknown, and dynamically estimated for each cool state, by retaining the maximum observed average power.

The temperature rate property is the rate of change of device temperature with respect to the time interval of the most recent update period, in units of °C./s.

The update period property is the time interval of a thermal model 600 update, which corresponds to the update event period of an observed thermal device 700, nominally 10 minutes, in units of s.

Heat Transfer

Heat transfer, $$\frac{d}{dt}(Q_{i,c,t}),$$

to zone 900 $i$, in cool state c, at time t, in units of W, is a measure of the rate of thermal energy change from various sources, for example including passive heat transfer, $$\frac{d}{dt}(Q_{Pi,t}),$$

active heat transfer, $$\frac{d}{dt}(Q_{Ai,c,t}),$$

solar heat transfer, $$\frac{d}{dt}(Q_{Si,t}),$$

and/or unobserved heat transfer, $$\frac{d}{dt}(Q_{Ui,t}),$$

$$\frac{d}{dt}(Q_{i,c,t}) = \frac{d}{dt}(Q_{Pi,t}) + \frac{d}{dt}(Q_{Ai,c,t}) + \frac{d}{dt}(Q_{Si,t}) + \frac{d}{dt}(Q_{Ui,t}) \quad (1.1)$$

In some embodiments, one or more components of heat transfer, $$\frac{d}{dt}(Q_{i,c,t}),$$

to zone 900 $i$, in cool state c, at time t, in units of W, can be neglected (e.g., observed or determined to be negligible), supporting a scalable solution based on available information, and/or a priori knowledge.

Figure 5:
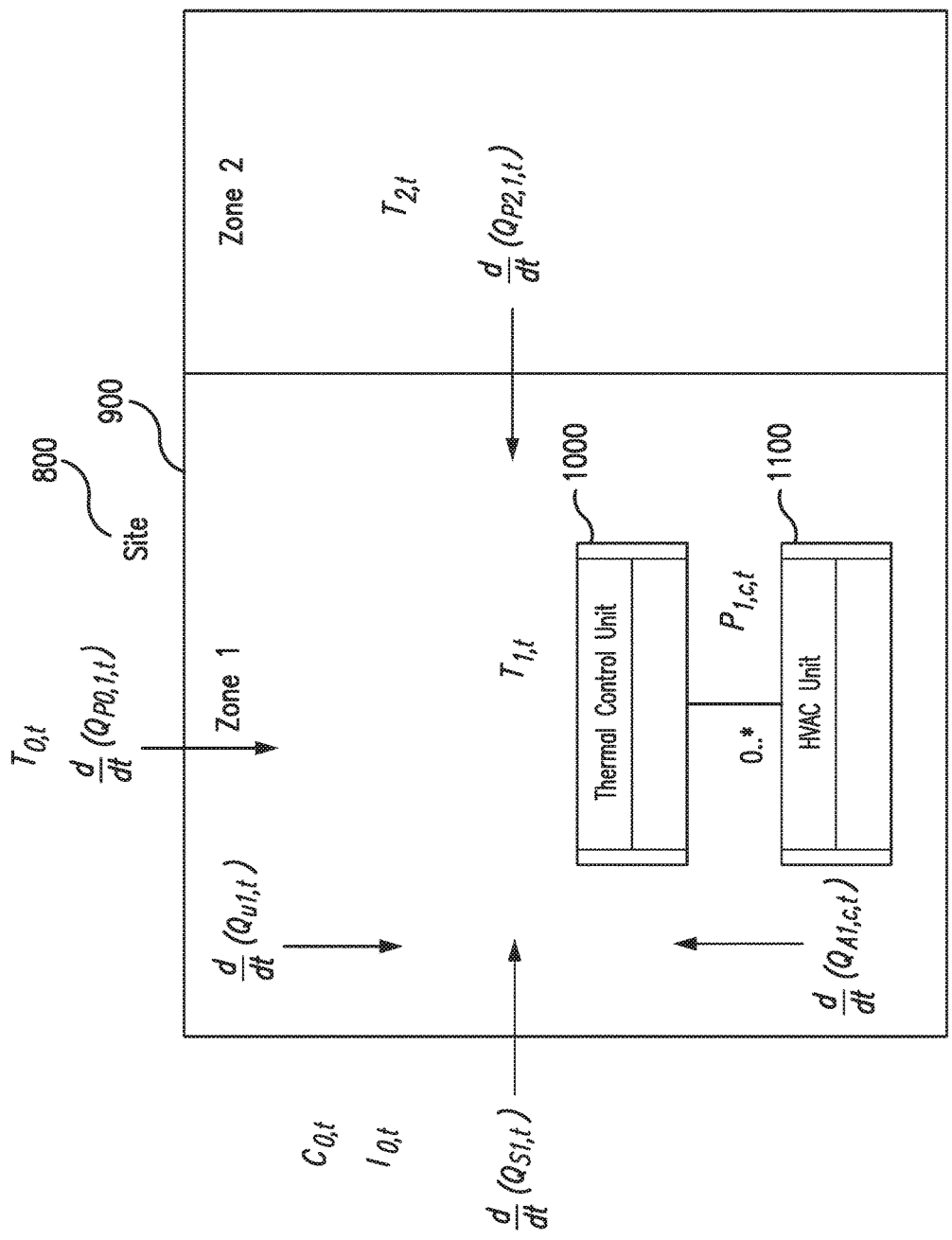
FIG. 5 shows a block diagram illustrating the structure of a thermal system, or site, comprising two zones and a surrounding environment, depicting heat flow into a zone, in one embodiment.

With reference to FIG. 5, heat transfer, $$\frac{d}{dt}(Q_{i,c,t}),$$

to zone 900 1, in a site 800 with two zones 900 and a surrounding environment, according to some embodiments of the disclosed thermal system, is illustrated.

Passive Heat Transfer

Newton's law of cooling concisely states that the passive heat transfer to a zone 900 $i$ across a boundary from an adjacent zone 900 $j$ is proportional to the difference in temperature between the zones 900, $T_{j,t} - T_{i,t}$.

Passive heat transfer, $$\frac{d}{dt}(Q_{Pi,j,t}),$$

to zone 900 $i$ from zone 900 $j$, at time t, in units of W, is equal to the product of the thermal transmittance, $h_{Pi,j}$, a property related to the heat transfer characteristics of the boundary material, in units of W/m²° C., the surface area of the shared zone 900 boundary, $A_{Pi,j}$, in units of m², and the difference between the temperature $T_{j,t}$, in zone 900 $j$, and $T_{i,t}$, in zone 900 $i$, in units of ° C., as shown in (1.2).

$$\frac{d}{dt}(Q_{Pi,t}) = \sum_{\substack{j=0 \\ j \neq i}}^{J} \frac{d}{dt}(Q_{Pi,j,t}) = \sum_{\substack{j=0 \\ j \neq i}}^{J} h_{Pi,j} A_{Pi,j}(T_{j,t} - T_{i,t}) \quad (1.2)$$

Passive heat transfer, $$\frac{d}{dt}(Q_{Pi,t}),$$

to zone 900 $i$, at time t, is equal to the sum of the heat transfer from zone 900 $j$, to each of J zones 900 which can share a boundary with zone 900 $i$. In some embodiments, passive heat transfer relative to the surrounding environment behaves in a manner similar to that of inter-zone (i.e., between zones 900) passive heat transfer, and thus can be modeled as a separate zone 900 for notational convenience.

Passive heat transfer, $$\frac{d}{dt}(Q_{Pi,j,t}),$$

to zone 900 $i$ from zone 900 $j$, at time t, in units of W, can be neglected, for example if the temperatures in zones 900 are correlated, similarly controlled, or otherwise insufficiently diverse to observe heat transfer between the zones 900.

Active Heat Transfer

Active heat transfer, $$\frac{d}{dt}(Q_{Ai,c,k,t}),$$

to zone 900 $i$, in cool state c, in HVAC unit 1100 $k$, at time t, in units of W, is equal to the product of the thermal efficiency, $\eta_{i,c,k}$, defined as the ratio of power produced or transported and power consumed by unit k, and the power, $P_{i,c,k,t}$, in units of W, consumed by HVAC unit 1100 $k$.

$$\frac{d}{dt}(Q_{Ai,c,t}) = \sum_{k=0}^{K-1} \frac{d}{dt}(Q_{Ai,c,k,t}) = \sum_{k=0}^{K-1} \eta_{i,c,k} P_{i,c,k,t} \quad (1.3)$$

Active heat transfer, $$\frac{d}{dt}(Q_{Ai,c,t}),$$

to zone 900 $i$, in cool state c, at time t, is equal to the sum of the heat transfer from HVAC unit 1100 $k$, in each of K units contained in the zone 900.

Substantially uniform thermal efficiency, $\eta_{i,c,k}$, associated with zone 900 $i$, in cool state c, of HVAC unit 1100 $k$, relative to power consumption can be assumed if the thermal efficiency of a specific HVAC unit 1100 $k$ is relatively constant, or sufficiently similar over the range of power consumption.

Multimodal HVAC units 1100, for example heat pumps, can exhibit non-uniform thermal efficiency relative to power consumption, often demonstrating discontinuous or nonlinear thermal efficiency with increasing power consumption. In some embodiments, a thermal model 600 indirectly forms an aggregate estimate of thermal efficiency in multimodal environments, extracted from the states of operation which are specifically observed.

Active heat transfer, $$\frac{d}{dt}(Q_{Ai,c,t}),$$

to zone 900 $i$, in cool state c, at time t, in units of W, is equal to the product of thermal efficiency, $\eta_{i,c}$, defined as the ratio of power produced or transported and power consumed in zone 900 $i$, in cool state c, and the power, $P_{i,c,t}$, in units of W, or normalized to unity range, consumed in zone 900 $i$.

$$\frac{d}{dt}(Q_{Ai,c,t}) = \sum_{k=0}^{K-1} \eta_{i,c,k} P_{i,c,k,t} = \eta_{i,c} P_{i,c,t} \quad (1.4)$$

The power, $P_{i,c,t}$, consumed in zone 900 $i$, in cool state c, at time t, in units of W, may not be an available or observable property. In such systems, the power, $P_{i,c,t}$, can be abstracted to a normalized representation which defines the duty cycle, or percentage of active time, in a zone 900 over a specific period of observation.

Thermal efficiency, $\eta_{i,c}$, associated with zone 900 $i$, in cool state c, can be independently defined in a specific zone 900, in the context of active cooling or heating operation. Active cooling and heating are generally supported by heterogeneous HVAC units 1100, and it is unreasonable to assume common thermal efficiency relative to cool state. In diagnostic applications, thermal efficiency, $\eta_{i,c}$, can be estimated in terms of active heat transfer, $$\frac{d}{dt}(Q_{Ai,c,t})$$

or derivative expressions.

Solar Heat Transfer

Solar heat transfer, $$\frac{d}{dt}(Q_{Si,s,t}),$$

to zone 900 $i$, from surface s (e.g., one or more walls, one or more windows, etc.), at time t, in units of W, is equal to the product of thermal transmittance of surface s, $h_{Si,s}$, a property related to the heat transfer characteristics of the surface material, in units of W/m²° C., the surface area of the shared boundary exposed to solar incidence, $A_{Si,s}$, in units of m², the complement of cloud cover, $c_{i,t}$, defined as the ratio of solar irradiance obscured by clouds and total solar irradiance, and solar irradiance, $I_{i,s,t}$, in units of W/m².

$$\frac{d}{dt}(Q_{Si,t}) = \sum_{s=0}^{S-1} \frac{d}{dt}(Q_{Si,s,t}) = \sum_{s=0}^{S-1} h_{Si,s} A_{Si,i}(1 - c_{i,t}) I_{i,s,t} \quad (1.5)$$

Solar irradiance, $I_{i,s,t}$, a measure of normalized solar power that is incident upon and normal to surface s, at time t, relates solar elevation, $\theta_t$, the angle of the sun on a plane normal to the horizon, solar azimuth, $\phi_t$, the angle of the sun on a plane parallel to the horizon relative to a north clockwise orientation, surface elevation, $\alpha_{i,s}$, and surface azimuth, $\beta_{i,s}$, in units of radians, and the available solar irradiance, $I_{i,t}$, in units of W/m².

$$I_{i,s,t} = \sin(\theta_t + \alpha_{i,s})\sin\left((\phi_t + \beta_{i,s}) - \frac{\pi}{2}\right)I_{i,t} \quad (1.6)$$

Solar heat transfer, $$\frac{d}{dt}(Q_{Si,t}),$$

to zone 900 i, at time t, is equal to the sum of the heat transfer from surface s, in each of S surfaces exposed to solar incidence which share a boundary with the surrounding environment and zone 900 i.

As the specific geometry of a thermal system can be unknown, it is impractical to assume that the surface elevation or surface azimuth, or even the surface quantity, is available for each surface which shares a boundary with every zone 900. Similarly, solar elevation and solar azimuth may not be readily available without implicit estimation, which is dependent upon latitude, longitude, and solar declination. The assumption of uniform cloud cover and solar irradiance, on an inter-zone 900 basis, is useful and generally sufficient.

Solar heat transfer, $$\frac{d}{dt}(Q_{Si,t}),$$

to zone 900 i, at time t, in units of W, is equal to the product of thermal transmittance, $h_{Si}$, in units of W/m²° C., of an aggregate surface, the surface area of the shared boundary exposed to solar incidence, $A_{Si}$, in units of m², the complement of cloud cover, $c_{i,s}$, and solar irradiance, $I_{i,t}$ in units of W/m².

$$\frac{d}{dt}(Q_{Si,t}) = h_{Si}A_{Si}(1 - c_{i,t})I_{i,t} \quad (1.7)$$

A weather model 500 can conveniently provide relevant estimates of solar irradiance, $I_{i,t}$ incident upon a single aggregate surface on a plane parallel to the horizon, and cloud cover, $c_{i,t}$, normalized to unity, supporting practical and effective solar heat transfer estimation.

Unobserved Heat Transfer

Unobserved heat transfer, $$\frac{d}{dt}(Q_{Ui,t}),$$

to zone 900 i, at time t, in units of W, is equal to unobserved heat, $q_{i,t}$, in units of W, which represents the heat transfer in zone 900 i from unobserved, unknown, or unmeasured sources, such as (but not limited to): fireplaces, ovens, stoves, lighting, non-instrumented HVAC units 1100, animals, and/or people.

$$\frac{d}{dt}(Q_{Ui,t}) = q_{i,t} \quad (1.8)$$

In some embodiments, unobserved heat transfer can be reasonably neglected if the unobserved heat sources in a zone 900 are known to be negligible, for example to reduce the order and complexity and/or to improve the numerical stability of a thermal model 600.

Combined Heat Transfers

In some embodiments, heat transfer, $$\frac{d}{dt}(Q_{i,c,t}),$$

to zone 900 i, in cool state c, at time t, in units of W, is equal to the sum of passive heat transfer, $$\frac{d}{dt}(Q_{Pi,t}), \quad (1.2),$$

active heat transfer, $$\frac{d}{dt}(Q_{Ai,c,t}), \quad (1.4),$$

solar heat transfer, $$\frac{d}{dt}(Q_{Si,t}), \quad (1.7),$$

and unobserved heat transfer, $$\frac{d}{dt}(Q_{Ui,t}), \quad (1.8),$$

as shown in (1.9).

$$\frac{d}{dt}(Q_{i,c,t}) = \sum_{\substack{j=0 \\ j\neq i}}^{J} h_{Pi,j}A_{Pi,j}(T_{j,t} - T_{i,t}) + \eta_{i,c}P_{i,c,t} + h_{Si}A_{Si}(1 - c_{i,t})I_{i,t} + q_{i,t} \quad (1.9)$$

A thermal model 600 can assume simple transient conduction to simplify analysis of a thermal system, for example by ignoring temperature and pressure gradients within a volume, thereby allowing an entire zone 900 to be considered as a single reservoir of heat, analogous to a thermal capacitor, which relates heat transfer and the rate of temperature change in a zone 900.

In some embodiments, heat transfer, $$\frac{d}{dt}(Q_{i,c,t}),$$

to zone 900 $i$, in cool state c, at time t, in units of W, is equal to the product of thermal mass, $C_i$, in units of J/° C., and rate of temperature change, $$\frac{d}{dt}(T_{i,c,t}),$$

in units of ° C./s.

$$\frac{d}{dt}(Q_{i,c,t}) = C_i \frac{d}{dt}(T_{i,c,t}) \qquad (1.10)$$

In some embodiments, thermal mass, $C_i$, in zone 900 $i$, in units of J/° C., is equal to the product of mass density, $p_i$, in units of kg/m³, volume, $V_i$, in units of m³, and mass specific heat, $c_{pi}$, in units of J/kg ° C.

$$C_i = p_i V_i c_{pi} \qquad (1.11)$$

Mechanically isolated systems do not support deformation in volumes, and associated work transfer, or mass transfer across boundaries. Mass density, volume, mass specific heat, and thermal mass, $C_i$, in zone 900 $i$, can be reasonably considered to be constant, if the distribution of mass in a thermal system is quasi-stationary, or changes slowly relative to the convergence period of a thermal model 600.

The rate of temperature change, $$\frac{d}{dt}(T_{i,c,t}),$$

in zone 900 $i$, in cool state c, at time t, in units of ° C./s, is equal to heat transfer (1.9) divided by the thermal mass, $C_i$, in units of J/° C. (1.10).

$$\frac{d}{dt}(T_{i,c,t}) = \qquad (1.12)$$

$$\sum_{\substack{j=0 \\ j \neq i}}^{J} \frac{h_{P_i,j} A_{P_i,j}}{C_i}(T_{j,t} - T_{i,t}) + \frac{\eta_{i,c}}{C_i}P_{i,c,t} + \frac{h_{S_i} A_{S_i}}{C_i}(1 - c_{i,t})I_{i,t} + \frac{q_{i,t}}{C_i}$$

The rate of temperature change, $$\frac{d}{dn}(T_{i,c,n}),$$

in zone 900 $i$, in cool state c, at sample n, in units of ° C./s, is an equivalent causal discrete time representation of the continuous form (1.12).

$$\frac{d}{dn}(T_{i,c,n}) = \sum_{\substack{j=0 \\ j \neq i}}^{J} \frac{h_{P_i,j} A_{P_i,j}}{C_i}(T_{j,n-1} - T_{i,n-1}) + \qquad (1.13)$$

$$\frac{\eta_{i,c}}{C_i}P_{i,c,n} + \frac{h_{S_i} A_{S_i}}{C_i}(1 - c_{i,n-1})I_{i,n-1} + \frac{q_{i,n-1}}{C_i}$$

The power, $P_{i,c,n}$, consumed in zone 900 $i$, in cool state c, at sample n, in units of W, represents the average power consumed in zone 900 $i$ during the preceding update period, $T_S$, in active cooling or active heating operation.

The energy, $E_{i,c,n}$, consumed in zone 900 $i$, in cool state c, at sample n, in units of J, is equal to the product of the power, $P_{i,c,n}$, consumed in zone 900 $i$, in units of W, and update period, $T_S$, in units of s.

$$E_{i,c,n} = T_S \sum_{k=0}^{K-1} P_{i,c,k,n} = T_S P_{i,c,n} \qquad (1.14)$$

It is not necessary to explicitly define several thermal system properties related to heat transfer, including thermal transmittances, areas, and thermal mass. Specific parameterized solutions, while potentially interesting in a diagnostics context, are not necessarily useful in energy or temperature estimation.

The thermal coefficients, $\omega_{i,j,c,n}$, associated with zone 900 $i$, in index j, in cool state c, at sample n, can be introduced for notational convenience from the rate of temperature change, $$\frac{d}{dn}(T_{i,c,n}),$$

in zone 900 $i$, (1.13). In other words, the thermal coefficients can be defined as the coefficients in the equation for the rate of temperature change (1.13)

$$\omega_{i,j,c,n} = \begin{cases} \frac{h_{P_i,j} A_{P_i,j}}{C_i} & j:[0, J-1] \\ \frac{\eta_{i,c}}{C_i} & j = J \\ \frac{h_{S_i} A_{S_i}}{C_i} & j = J+1 \\ \frac{q_{i,n-1}}{C_i} & j = J+2 \end{cases} \qquad (1.15)$$

In some embodiments, passive heat transfer coefficients can be re-indexed in index j, thereby eliminating the condition j=i, and sequentially indexing the surrounding environment and each of J zones 900 that can share a boundary with zone 900 $i$, including the surrounding environment. Passive heat transfer coefficients can be ordered according to zone 900 identifier, or according to any other consistent deterministic criterion. Active heat transfer coefficients can be independently defined in a specific zone 900 in the context of active cooling or active heating operation. The thermal coefficient, $\omega_{i,J+1,c,n}$, associated with active heat transfer, can be independently evaluated from observations constrained to either active cooling or active heating operation.

The incident parameters, $x_{i,j,c,n}$, associated with zone 900 $i$, in index $j$, in cool state c, at sample n, can be introduced from the rate of temperature change, $$\frac{d}{dn}(T_{i,c,n}),$$

in zone 900 $i$, (1.13), expressed as the difference between the temperature $T_{j,t}$, in zone 900 $j$, and $T_{i,t}$, in zone 900 $i$, in units of ° C., energy, $E_{i,c,n}$, consumed in zone 900 $i$, in cool state c, in units of J, and update period, $T_S$, in units of s, (1.14), the complement of cloud cover, $c_{i,t}$, and solar irradiance, $I_{i,s,t}$, in units of W/m².

$$x_{i,j,c,n} = \begin{cases} (T_{j,n-1} - T_{i,n-1}) & j:[0, J-1] \\ \frac{E_{i,c,n}}{T_S} & j = J \\ (1 - c_{i,n-1})I_{i,n-1} & j = J+1 \\ 1.0 & j = J+2 \end{cases} \quad (1.16)$$

The rate of temperature change, $$\frac{d}{dn}(T_{i,c,n}),$$

in zone 900 $i$, in cool state c, at sample n, in units of ° C./s, substituting thermal coefficients, $\omega_{i,j,c,n}$, (1.15), and incident parameters, $x_{i,j,c,n}$, associated with zone 900 $i$, is an equivalent representation of the discrete time form (1.13).

$$\frac{d}{dn}(T_{i,c,n}) = \qquad (1.17)$$

$$\sum_{j=0}^{J-1} \omega_{i,j,c,n} x_{i,j,n} + \omega_{i,J,c,n} x_{i,J,n} + \omega_{i,J+1,c,n} x_{i,J+1,n} + \omega_{i,J+2,c,n} x_{i,J+2,n}$$

The reference, $y_{i,c,n}$, equal to the observed rate of temperature change, $$\frac{d}{dn}(T_{i,c,n}),$$

in zone 900 $i$, in cool state c, at sample n, in units of ° C./s, (1.17), can be expressed as a discrete time derivative of temperature, $T_{i,n}$, equal to the product of the thermal coefficient vector, $\overline{\omega}_{i,c,n}$, and incident vector, $\overline{x}_{i,c,n}$.

$$y_{i,c,n} = \frac{d}{dn}(T_{i,c,n}) \approx \frac{T_{i,n} - T_{i,n-1}}{T_S} \approx \frac{T_{i,n} - T_{i,n-2}}{2T_S} = \overline{x}_{i,c,n}\overline{\omega}_{i,c,n} \quad (1.18)$$

The discrete time derivative of temperature, $T_{i,n}$, can be an appropriate causal approximation. The order of the selected discrete time derivative approximation is significant, as latency is order-dependent. First and second order discrete time derivative approximations are convenient and compact representations, as defined, with 0.5 and 0.0 sample phase bias, and 0.5 and 1.0 sample latencies, respectively. Higher order discrete time derivative approximations may not be sufficiently compact relative to the rate of temperature change in a thermal system.

Updating the Thermal Model

In some embodiments, the thermal coefficient vector, $\overline{\omega}_{i,c,n}$, associated with zone 900 $i$, in cool state c, at sample n, with dimension [J+3,1], is adaptively estimated by solving a system of linear equations, each equation formed from an independent observation of an incident vector, $\overline{x}_{i,c,n}$, and a reference, $y_{i,c,n}$. The thermal coefficient vector, $\overline{\omega}_{i,c,n}$, can be solved synchronously, for example on availability of new information at update period, $T_S$, in units of s, or asynchronously, for example when a norm of energy or temperature estimation error indicates the current solution demonstrates insufficient accuracy.

The observed rate of temperature change, $$\frac{d}{dn}(T_{i,c,n}),$$

in zone 900 $i$, in cool state c, at sample n, in units of ° C./s, (1.18), is expressed as the product of the thermal coefficient vector, $\overline{\omega}_{i,c,n}$, and incident vector, $\overline{x}_{i,c,n}$, in the form of a discrete difference equation. A thermal model 600 update is defined to occur on integral sample boundaries, with update period, $T_S$, in units of s, as a matter of convenience.

A thermal model 600 can be alternatively and equivalently defined as an asynchronous system by retaining the time intervals between asynchronous samples.

Figure 6:
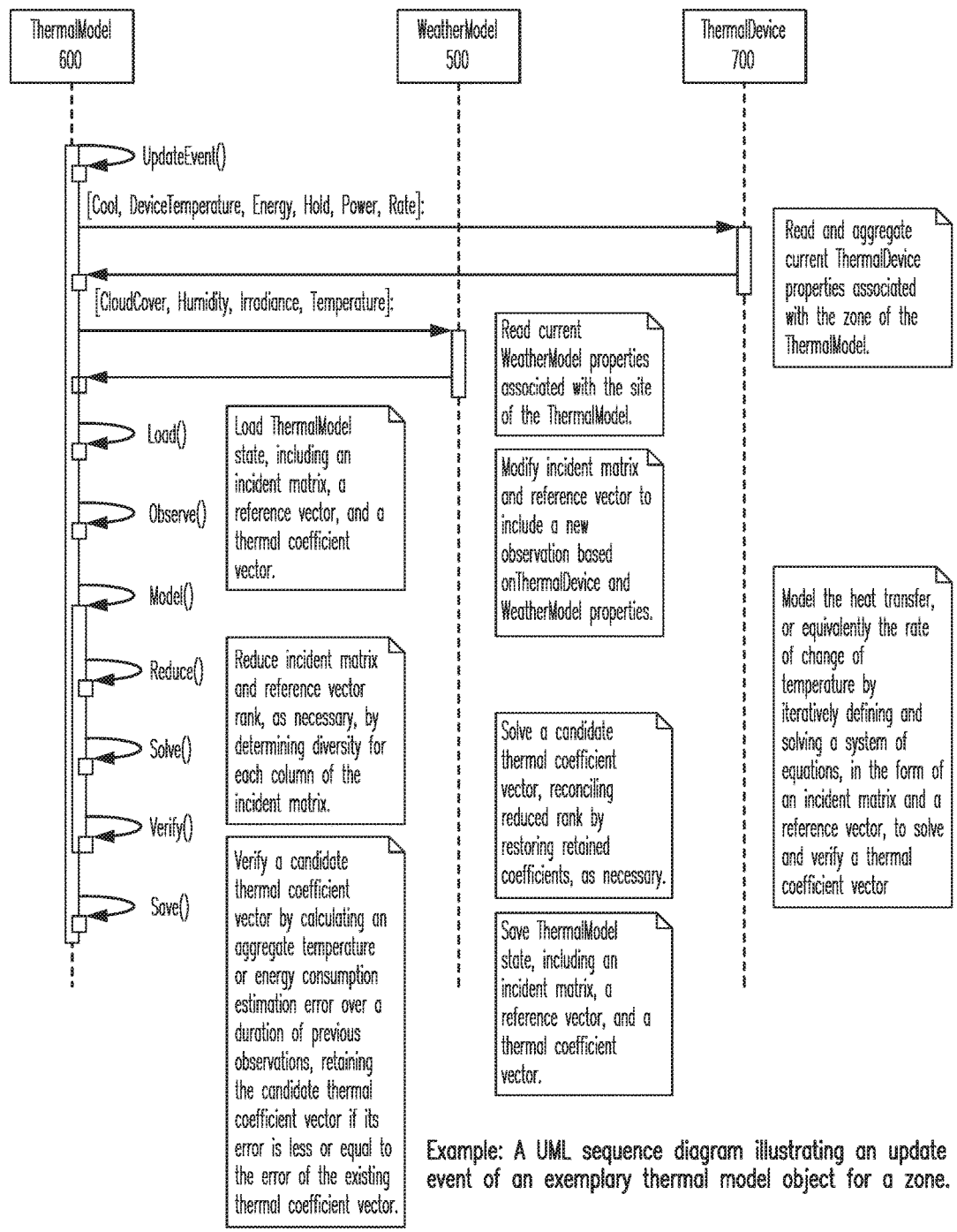
FIG. 6 shows a UML sequence diagram illustrating an update event of an exemplary thermal model object for a zone, in one embodiment.

With reference to FIG. 6, in some embodiments a thermal model 600 observes one or more thermal devices 700, interacts with zero or more thermal models 600 associated with a site 800, and/or observes a weather model 500, in an update event.

Observation

The incident matrix, $\overline{X}_{i,c,n}$, associated with zone 900 $i$, in cool state c, at sample n, with dimension [N,J+3], can be formed from N independent observations of incident vectors, $\overline{x}_{i,c,m}$, at sample m, where m: [0,N−1].

$$\overline{X}_{i,c,n} = \begin{bmatrix} \overline{x}_{i,c,n-(N-1)} \\ \overline{x}_{i,c,n-(N-2)} \\ \vdots \\ \overline{x}_{i,c,n} \end{bmatrix} \quad (1.19)$$

The reference vector, $\overline{y}_{i,c,n}$, associated with zone 900 $i$, in cool state c, at sample n, with dimension [N,1], is formed from N independent observations of references, $y_{i,c,m}$, at sample m, where m: [0,N−1] and corresponds to sample indices selected to form the incident matrix, $\overline{X}_{i,c,n}$.

$$\overline{y}_{i,c,n} = \begin{bmatrix} y_{i,c,n-(N-1)} \\ y_{i,c,n-(N-2)} \\ \vdots \\ y_{i,c,n} \end{bmatrix} \quad (1.20)$$

In some embodiments, the memory duration, N, of the incident matrix, $\bar{X}_{i,c,n}$, and reference vector, $\bar{y}_{i,c,n}$, associated with zone 900 $i$, at sample n, assuming contiguous observations, is equal to the integral ratio of the observation duration, $T_X$, and update period, $T_S$, in units of s. The incident matrix, $\bar{X}_{i,c,n}$, and reference vector, $\bar{y}_{i,c,n}$, observations need not be sequential, nor contiguous, to facilitate a solution.

$$N = \left\lceil \frac{T_X}{T_S} \right\rceil \quad (1.21)$$

The memory duration, N, can be selected to ensure that a sufficiently diverse set of observances are used in solving the thermal coefficient vector, $\bar{y}_{i,c,n}$, and/or to ensure that the numerical accuracy of the solution results in energy or temperature estimation error that satisfies a specified norm.

Solution

In some embodiments, the reference vector, $\bar{y}_{i,c,n}$, associated with zone 900 $i$, in cool state c, at sample n, is equal to the product of the incident matrix, $\bar{X}_{i,c,n}$, and the thermal coefficient vector, $\bar{\omega}_{i,c,n}$. The thermal coefficient vector, $\bar{\omega}_{i,c,n}$, is indirectly solved by minimizing the $L_2$ error in the linear system.

$$\bar{y}_{i,c,n} = \bar{X}_{i,c,n} \bar{\omega}_{i,c,n} \quad (1.22)$$

The transpose of the incident matrix, $\bar{X}_{i,c,n}^T$, associated with zone 900 $i$, in cool state c, at sample n, can be multiplied by the linear system (1.22), as shown in (1.23) below.

$$\bar{X}_{i,c,n}^T \bar{y}_{i,c,n} = \bar{X}_{i,c,n}^T \bar{X}_{i,c,n} \bar{\omega}_{i,c,n} \quad (1.23)$$

The inverse of the product of the transpose of the incident matrix, $\bar{X}_{i,c,n}^T$, and the incident matrix, $\bar{X}_{i,c,n}$, associated with zone 900 $i$, in cool state c, at sample n, is multiplied by the linear system, (1.23), and simplified to isolate a solution for the thermal coefficient vector, $\bar{\omega}_{i,c,n}$.

$$\bar{\omega}_{i,c,n} = (\bar{X}_{i,c,n}^T \bar{X}_{i,c,n})^{-1} \bar{X}_{i,c,n}^T \bar{y}_{i,c,n} \quad (1.24)$$

The thermal coefficient vector, $\bar{\omega}_{i,c,n}$, associated with zone 900 $i$, in cool state c, at sample n, can be extracted by explicit matrix inversion, (1.24), though this technique is computationally more expensive, at $O((J+3)^3)$, and numerically less accurate than several alternative methods.

The thermal coefficient vector, $\bar{\omega}_{i,c,n}$, associated with zone 900 $i$, in cool state c, at sample n, can be solved using a generalization of the inverse matrix, including a variant of the Moore Penrose method, using QR decomposition, single value decomposition, or Gaussian elimination.

The source matrix, $\bar{U}_{i,c,n}$, and the target vector, $\bar{z}_{i,c,n}$, associated with zone 900 $i$, in cool state c, at sample n, are substituted in the linear system, (1.23).

$$\bar{z}_{i,c,n} = \bar{U}_{i,c,n} \bar{\omega}_{i,c,n} \quad (1.25)$$

Gauss Jordan elimination or Gaussian elimination compose an augmented matrix equation from the source matrix, $\bar{U}_{i,c,n}$, and the target vector, $\bar{z}_{i,c,n}$, associated with zone 900 $i$, in cool state c, at sample n, and perform a sequence of elementary row operations, including scaling and adding or subtracting two rows to replace an existing row, or reordering rows. The sequence of elementary row operations continues until the augmented matrix equation is in upper row echelon form, or upper triangular with leading coefficients equal to one.

$$\begin{bmatrix} u_{0,0} & u_{0,1} & \cdots & u_{0,J+1,n} \\ u_{1,0} & u_{1,1} & \cdots & u_{1,J+1,c,n} \\ \vdots & \vdots & \vdots & \vdots \\ u_{J+1,0} & u_{J+1,1} & \cdots & u_{J+1,J+1} \end{bmatrix} \begin{bmatrix} z_0 \\ z_1 \\ \vdots \\ z_{J+1} \end{bmatrix} \Rightarrow \quad (1.26)$$

$$\begin{bmatrix} 1 & v_{0,1} & \cdots & v_{0,J+1} \\ 0 & 1 & \cdots & v_{1,J+1} \\ \vdots & \vdots & \vdots & \vdots \\ 0 & 0 & \cdots & 1 \end{bmatrix} \begin{bmatrix} \zeta_0 \\ \zeta_1 \\ \vdots \\ \zeta_{J+1} \end{bmatrix} \Rightarrow \begin{bmatrix} 1 & 0 & \cdots & 0 \\ 0 & 1 & \cdots & 0 \\ \vdots & \vdots & \cdots & \vdots \\ 0 & 0 & \cdots & 1 \end{bmatrix} \begin{bmatrix} \omega_{i,0,c,n} \\ \omega_{i,1,c,n} \\ \vdots \\ \omega_{i,J+1,c,n} \end{bmatrix}$$

Gauss Jordan elimination continues the sequence of elementary row operations until the augmented matrix equation, (1.26), is in reduced row echelon form, or an identity matrix and the solution thermal coefficient vector, $\bar{\omega}_{i,c,n}$.

Gaussian elimination employs back substitution to an upper row echelon form matrix to directly solve the lower order coefficients and substitute the results into higher order terms, until the augmented matrix equation, (1.26), is in reduced row echelon form, reducing computational complexity.

The thermal coefficient vector, $\bar{\omega}_{i,c,n}$, associated with zone 900 $i$, in cool state c, at sample n, can be solved for multiple memory durations, N, which can be particularly useful in transient heat transfer conditions.

In some embodiments, unobserved heat transfer, $$\frac{d}{dn}(Q_{Ui,n}),$$

to zone 900 $i$, at sample n, in units of W, is assumed to be quasi-stationary, or changes slowly relative to the convergence period of the thermal model 600. If unobserved heat transfer, $$\frac{d}{dn}(Q_{Ui,n}),$$

is not quasi-stationary, a reduced memory duration, N, can be applied to extract the thermal coefficient, $\omega_{i,J+2,c,n}$, related to unobserved heat transfer, and the remaining thermal coefficient vector, $\bar{\omega}_{i,c,n}$, can be solved at an increased memory duration, N, to retain the advantages associated with reducing the condition of the solution while accommodating transient unobserved heat transfer.

It can be useful to detect or monitor change in the passive heat transfer, $$\frac{d}{dn}(Q_{Pi,n}),$$

active heat transfer, $$\frac{d}{dn}(Q_{Ai,c,n}),$$

solar heat transfer, $$\frac{d}{dn}(Q_{Si,n}),$$

and unobserved heat transfer, $$\frac{d}{dn}(Q_{Ui,n}),$$

which could indicate inefficient operation or necessary maintenance.

Diagnostic conditions of interest, including open or closed doors and/or windows, and reduced thermal efficiency, $\eta_{i,c}$, can be transient relative to the nominal memory duration, N, or can require lower detection latency. The thermal coefficient vector, $\overline{\omega}_{i,c,n}$, can be solved at an appropriate reduced memory duration, N, to accommodate transient conditions and reduce latency, as necessary and/or desired.

Quasi-stationary thermal model 600 coefficient vector, $\overline{\omega}_{i,c,n}$, states and transitions can be observed over the memory duration, N, and diagnostic properties can be extracted from the coefficient solutions.

Thermal efficiency, $\eta_{i,c}$, associated with zone 900 $i$, can be estimated from the thermal coefficient, $\omega_{i,j,c,n}$, associated with zone 900 $i$, in index j, in cool state c, representing active heat transfer, (1.15).

Thermal transmittance, $h_{Si}$, in units of W/m$^{2\circ}$ C., and changes in relative geometry, possibly due to opened or closed doors or windows, can be detected from the thermal coefficients, $\omega_{i,j,c,n}$, associated with zone 900 $i$, in index j, in cool state c, representing passive heat transfer, (1.15).

Thermal mass, $C_i$, in zone 900 $i$, in units of J/° C., and surface area of the shared zone 900 boundary, $A_{Pi,j}$, relative to zone 900 $j$, in units of m$^2$, can be normalized to unity to estimate normalized thermal efficiency, $\eta_{i,c}$, and/or thermal transmittance, $h_{Si}$.

Rank Reduction

In some embodiments, the numerical accuracy of the thermal coefficient vector, $\overline{\omega}_{i,c,n}$, associated with zone 900 $i$, in cool state c, at sample n, is related to the diversity or independence of observations in the incident matrix, $\overline{X}_{i,c,n}$, and reference vector, $\overline{y}_{i,c,n}$. Diversity can be quantified in the form of the condition number, $\kappa(\overline{U}_{i,c,n})$, of the source matrix, $\overline{U}_{i,c,n}$, which quantifies the sensitivity of a solution to perturbations or errors in the matrix, as the ratio of range of eigenvalues of the matrix, $\lambda_{M,\overline{U},i,c,n}$ and $\lambda_{N,\overline{U},i,c,n}$, respectively.

$$\kappa(\overline{U}_{i,c,n}) = \|(\overline{U}_{i,c,n})^{-1}\|_2 \|(\overline{U}_{i,c,n})\|_2 = \frac{\lambda_{M,\overline{U},i,c,n}}{\lambda_{N,\overline{U},i,c,n}} \quad (1.27)$$

The condition number, $\kappa(\overline{U}_{i,c,n})$, indicates that the source matrix, $\overline{U}_{i,c,n}$, associated with zone 900 $i$, in cool state c, at sample n, is well-conditioned when the result approaches unity, is singular as the result approaches infinity, and is considered ill-conditioned above a threshold defined by a specified numerical accuracy.

The digits of accuracy lost, $D_{i,c,n}$, in the solution due to perturbations or errors in the source matrix, $\overline{U}_{i,c,n}$, independent of the effects of finite numerical precision, is proportional to the logarithm of the condition number.

$$D_{i,c,n} \propto \log_{10}(\kappa(\overline{U}_{i,c,n})) \quad (1.28)$$

Computation of the condition number of the source matrix, $\overline{U}_{i,c,n}$, associated with zone 900 $i$, in cool state c, at sample n, prior to each solution of the thermal coefficient vector, $\overline{\omega}_{i,c,n}$, can significantly increase the complexity of the solution, and may not be practical in some environments.

As an alternative to computation of the condition number of the source matrix, $\overline{U}_{i,c,n}$, associated with zone 900 $i$, in cool state c, at sample n, applies rank reduction to indirectly reduce the condition number, $\kappa(\overline{U}_{i,c,n})$, and increase numerical accuracy, prior to solution of the thermal coefficient vector, $\overline{\omega}_{i,c,n}$.

An incident population density, $\rho_{i,j,c,n}$, associated with zone 900 $i$, in index j, in cool state c, at sample n, is equal to the ratio of elements in the incident matrix, $\overline{X}_{i,c,n}$, in index j, with absolute values greater than $\varepsilon_N$, a small positive threshold, and the memory duration, N. If the incident population density, $\rho_{i,j,c,n}$, does not exceed the minimum incident population density, $\rho_N$ the column of the incident matrix, $\overline{X}_{i,c,n}$, the row of the reference vector, $\overline{y}_{i,c,n}$, and the row of the thermal coefficient vector, $\overline{\omega}_{i,c,n}$, in index j, are excluded prior to the solution.

$$\rho_{i,j,c,n} = \frac{\sum_{m=0}^{N-1}(|\overline{X}_{i,j,c,m}| > \varepsilon_N)}{N} \leq \rho_N \quad (1.29)$$

Transient rank reduction of the incident matrix, $\overline{X}_{i,c,n}$, and the reference vector, $\overline{y}_{i,c,n}$, associated with zone 900 $i$, in cool state c, at sample n, is applied to the current solution of the thermal coefficient vector, $\overline{\omega}_{i,c,n}$, and not necessarily retained for subsequent solutions. The thermal coefficient vector, $\overline{\omega}_{i,c,n}$, is partially solved in reduced rank solutions, and coefficients corresponding to excluded model indices are either retained from the most recent solution, or assigned nominal values.

A priori rank reduction does not guarantee a sufficiently well-conditioned solution of the thermal coefficient vector, $\overline{\omega}_{i,c,n}$, associated with zone 900 $i$, in cool state c, at sample n. Therefore, in some embodiments it is necessary to verify the range of each thermal coefficient, $\omega_{i,c,n}$, according to expected norms. A thermal coefficient, $\omega_{i,c,n}$, that is out of range is excluded, and the coefficient from the most recent solution is retained.

Persistent rank reduction of the incident matrix, $\overline{X}_{i,c,n}$, and the reference vector, $\overline{y}_{i,c,n}$, associated with zone 900 $i$, in cool state c, at sample n, is applied to the current solution of the thermal coefficient vector, $\overline{\omega}_{i,c,n}$, and is retained for subsequent solutions. Persistent rank reduction eliminates thermal coefficients, $\omega_{i,c,n}$, which have relatively negligible effect on thermal model 600 confidence, to indirectly reduce the condition number, $\kappa(\overline{U}_{i,c,n})$, and increase numerical accuracy.

In a thermal model 600 with relatively high confidence, quantified indirectly by condition number, or directly by energy or temperature estimation error, a thermal coefficient, $\omega_{i,c,n}$, having an absolute value that is insignificant relative to other modes of heat transfer or production, can be excluded in some embodiments. Persistent rank reduction eliminates the column of the incident matrix, $\overline{X}_{i,c,n}$, the row of the reference vector, $\bar{y}_{i,c,n}$, and the row of the thermal coefficient vector, $\bar{\omega}_{i,c,n}$, in index j, corresponding to an excluded thermal coefficient. Persistent rank reduction is opportunistic, reconciling a priori assumptions of the physics of the thermal system with a posteriori observations.

Thermal Coefficients

Figure 7:
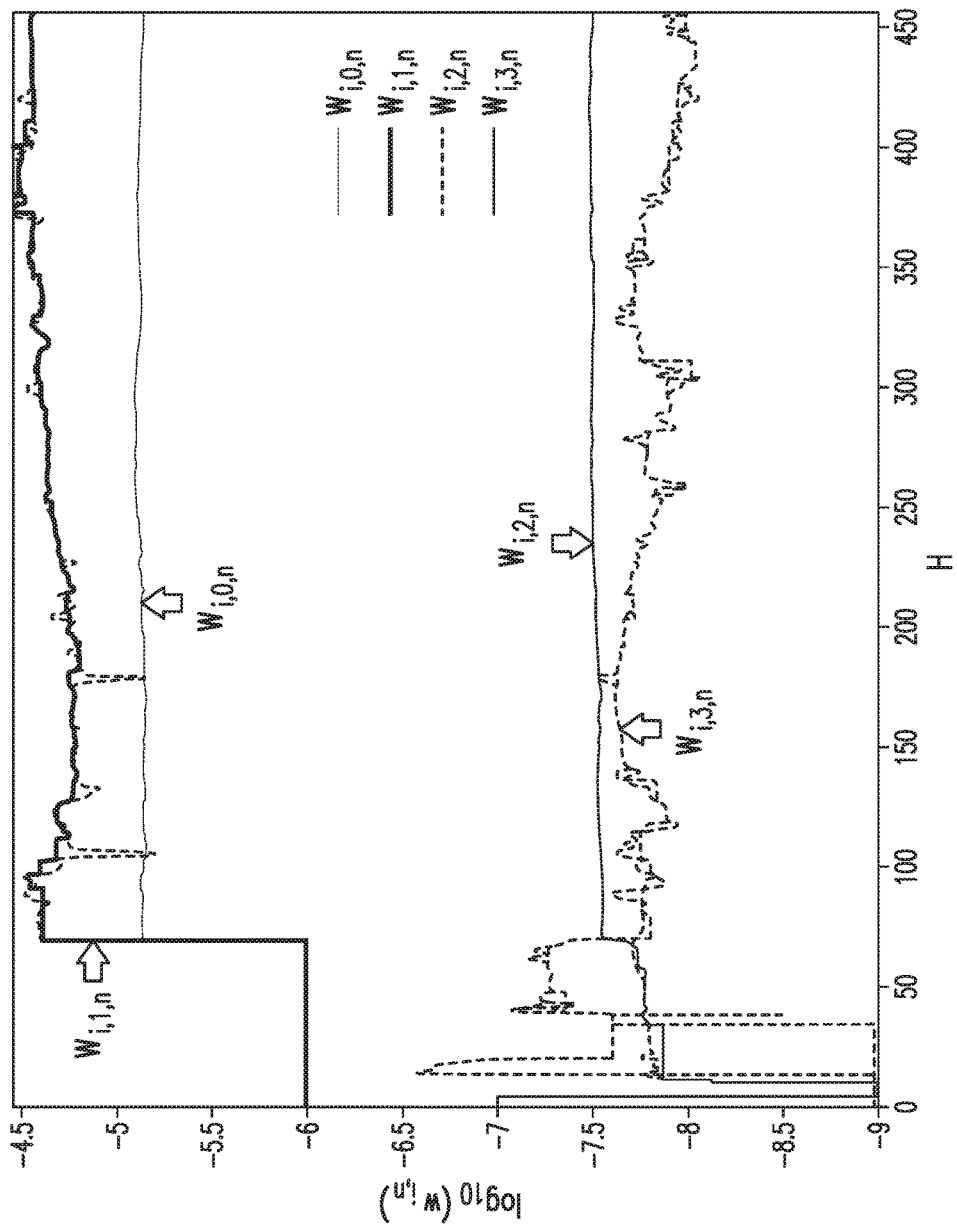
FIG. 7 shows a graph illustrating a thermal model coefficient update sequence for a zone, in one embodiment.

With reference to FIG. 7, a thermal model 600 associated with zone 900 i, in a site 800 having two zones 900, and memory duration, N, equal to 10 days, was updated over a duration of 20 days, exclusively in active heating mode, modifying incident matrices, $\bar{X}_{i,c,n}$, and reference vectors, $\bar{y}_{i,c,n}$, in each update period, $T_S$, in units of s, applying rank reduction as appropriate, and solving thermal coefficient vectors, $\bar{\omega}_{i,c,n}$.

The thermal coefficient vector, $\bar{\omega}_{i,c,n}$, associated with zone 900 i, in cool state c, at sample n, relates the rate of temperature change, $$\frac{d}{dn}(T_{i,c,n}),$$

in units of ° C./s, to passive heat transfer from the surrounding environment, $\omega_{i,0,c,n}$, passive heat transfer from the adjacent zone 900, $\omega_{i,1,c,n}$, active heat transfer, $\omega_{i,2,c,n}$, from a heating type HVAC unit 1100, in zone 900 i, and solar heat transfer, $\omega_{i,3,c,n}$.

A verification test was employed to improve the accuracy and stability of subsequent energy and temperature estimation. The thermal coefficient vector, $\bar{\omega}_{i,c,n}$, was only retained if it exhibited a lower $L_2$ error in forward temperature estimation over a recent window of observations, nominally 6 hours. The selection of error metric, or norm, and window of observation to perform thermal coefficient verification was made strictly on the basis of convenience, though any measure of error related to energy or temperature estimation over a contiguous or discontiguous set of observations may be suitable for determining whether a candidate thermal coefficient vector demonstrates improved estimation accuracy relative to an existing thermal coefficient vector. Thermal coefficient vector verification continuously improves the accuracy and stability of a thermal model 600, by retaining the representation having the best observed performance. The light volatile lines without enumeration correspond to the thermal coefficient vector, $\bar{\omega}_{i,c,n}$, without the use of a verification test.

Estimation

In some embodiments, the utility of the thermal coefficient vector, $\bar{\omega}_{i,c,n}$, is found in the form of energy and temperature estimation, exercised to accommodate the specific requirements of an application, to include temperature control by estimating either energy to minimize consumption, or temperature to facilitate optimal start. Energy and temperature estimation are agnostic with respect to temporal direction.

Energy Estimations

The energy, $E_{i,c,n}$, consumed in zone 900 i, in cool state c, between sample n−1 and sample n, in units of J, can be estimated from the reference, $y_{i,c,n}$, in units of ° C./s, (1.18), thermal model 600 coefficient, $\omega_{i,j,c,n}$, (1.15), and incident parameter, $x_{i,j,c,n}$, (1.16), definitions reorganized to express energy, $E_{i,c,n}$, as a function of the thermal coefficient vector, $\bar{\omega}_{i,c,n}$, incident vector, $\bar{x}_{i,c,n}$, and update period, $T_S$, in units of s.

$$E_{i,c,n} = \left(\frac{T_S}{\omega_{i,J,c,n}}\right)\left(y_{i,c,n} - \bar{x}_{i,c,n}\bar{\omega}_{i,c,n}\big|_{x_{i,J,c,n}=E_{i,c,n}=0}\right) \quad (1.30)$$

The energy, $E_{i,c,n}$, consumed in zone 900 i, in cool state c, at sample n, in units of J, is equivalently defined from the reference, $y_{i,c,n}$, in units of ° C./s, (1.17), as a function of thermal model 600 coefficients, $\omega_{i,j,c,n}$, temperatures, $T_{i,n-1}$ and $T_{i,n}$, in zone 900 i, at samples n−1 and n, and $T_{j,n-1}$, in zone 900 j, in each of J zones 900 which can share a boundary with zone 900 i, including the surrounding environment, at sample n−1, in units of ° C., cloud cover, $c_{i,n-1}$, solar irradiance, $I_{i,n-1}$, in units of W/m², and update period, $T_S$, in units of s.

$$E_{i,c,n} = \left(\frac{T_S}{\omega_{i,J,c,n}}\right)\left(\left(\frac{T_{i,n}-T_{i,n-1}}{T_S}\right) - \left(\sum_{j=0}^{J-1}\omega_{i,j,c,n}(T_{j,n-1}-T_{i,n-1}) + \omega_{i,J+1,c,n}(1-c_{i,n-1})I_{i,n-1} + \omega_{i,J+2,c,n}\right)\right) \quad (1.31)$$

The energy, $E_{i,c,n}$, consumed in zone 900 i, in cool state c, at sample n, in units of J, can be used to estimate energy consumption required to realize a future forecast temperature sequence, or to verify the energy consumed in a previously observed temperature sequence, $T_{i,n-1}$ and $T_{i,n}$, in zone 900 i, in units of ° C.

The energy, $E_{i,c,n}$, consumed in zone 900 i, between samples n−1 and n, in units of J, is restricted in range to the maximum available energy, $E_{M,i,c}$, in cool state c, in units of J, equal to the product of the maximum available power, $P_{M,i,c}$, in cool state c, in units of W, and update period, $T_S$, in units of s.

$$E_{i,n}:[0,E_{M,i,c}]=[0,T_S P_{M,i,c}] \quad (1.32)$$

Forward or reverse temperature estimation can be applied to reconcile the range restricted energy, $E_{i,c,n}$, with the appropriate temperature, $T_{i,n}$ or $T_{i,n-1}$, respectively.

Temperature Estimations

The temperature, $T_{i,n}$, in zone 900 i, at sample n, in units of ° C., can be estimated as a function of a temperature, $T_{i,n-1}$, at sample n−1, in units of ° C., and energy, $E_{i,c,n}$, in units of J. Alternatively, the temperature, $T_{i,n-1}$, in zone 900 i, at sample n−1, in units of ° C., can be estimated as a function of a temperature, $T_{i,n-1}$, at sample n, in units of ° C., and energy, $E_{i,c,n}$, in units of J.

Forward Temperature Estimations

In some embodiments, the temperature, $T_{i,n}$, in zone 900 i, at sample n, in units of ° C., is defined from the reference, $y_{i,c,n}$, in units of ° C./s, (1.17), as a function of thermal model 600 coefficients, $\omega_{i,j,c,n}$, temperature, $T_{i,n-1}$, in zone 900 i, and $T_{j,n-1}$, in zone 900 j, at sample n−1, in each of J zones 900 that can share a boundary with zone 900 i, including the surrounding environment, at sample n−1, in units of ° C., energy, $E_{i,c,n}$, in units of J, cloud cover, $c_{i,n-1}$, solar irradiance, $I_{i,n-1}$, in units of W/m², and update period, $T_S$, in units of s.

$$T_{i,n} = T_{i,n-1} + T_S \left( \sum_{j=0}^{J-1} \omega_{i,j,c,n}(T_{j,n-1} - T_{i,n-1}) + \omega_{i,J,c,n}\left(\frac{E_{i,c,n}}{T_S}\right) + \omega_{i,J+1,c,n}(1 - c_{i,n-1})I_{i,n-1} + \omega_{i,J+2,c,n} \right) \quad (1.33)$$

The temperature, $T_{i,n}$, in zone 900 $i$, at sample n, in units of ° C., can be estimated from a previously observed or estimated temperature, $T_{i,n-1}$, at sample n-1, in units of ° C., and the energy, $E_{i,c,n}$, consumed in zone 900 $i$, in cool state c, at sample n, in units of J, consumed during the sequence.

The temperature, $T_{i,n}$, in zone 900 $i$, at sample n, in units of ° C., can be contiguously estimated from the previous estimated temperature, $T_{i,n-1}$, at sample n-1, in units of ° C., such that only the first sample in the sequence, $T_{i,0}$, is actually observed and used to estimate the next sample, $T_{i,1}$. In a causal system, only forecast temperature estimates are available, and any prediction error that occurs in estimation of the temperature, $T_{i,n}$, is cumulative.

Figure 8:
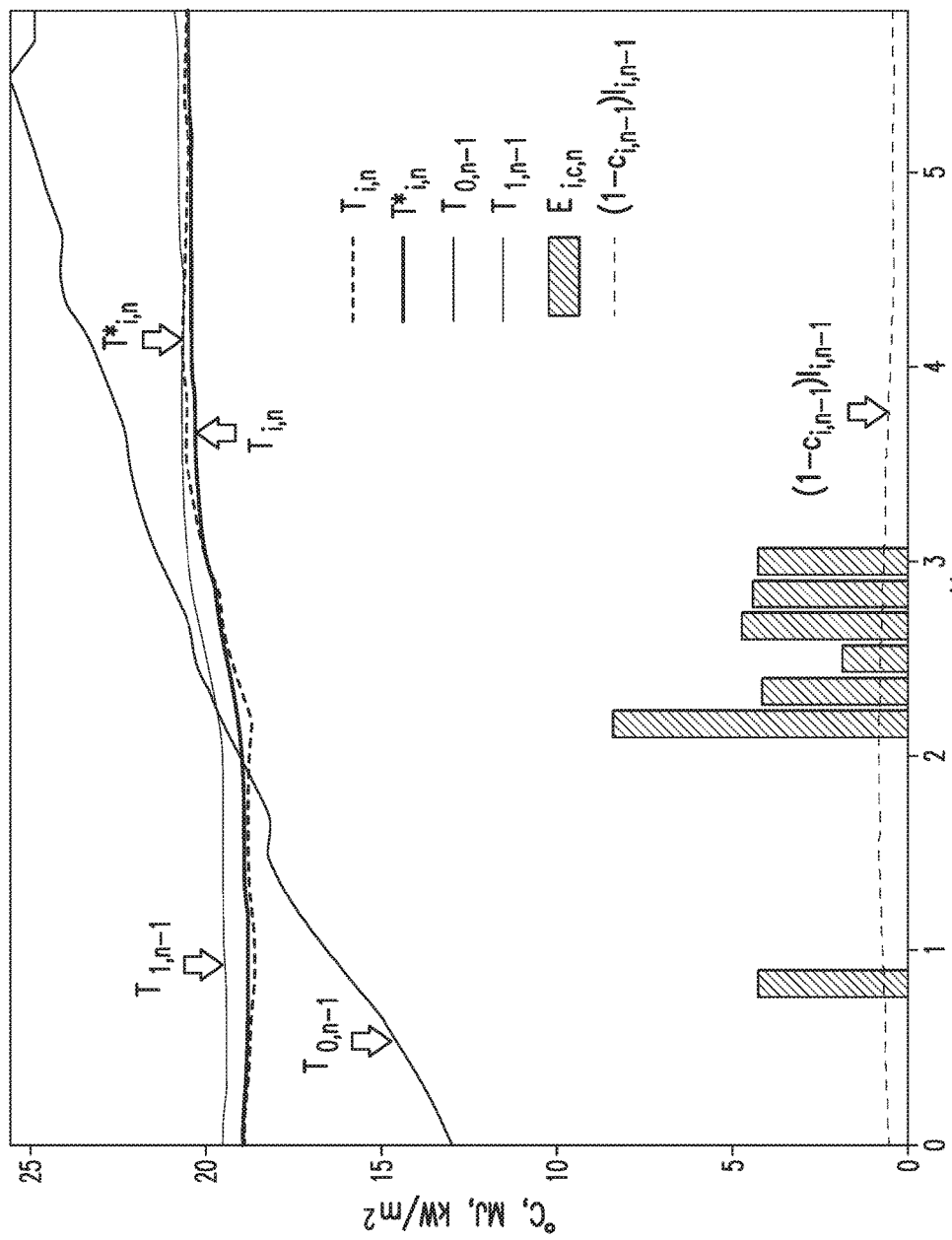
FIG. 8 shows a graph illustrating a thermal model forward temperature estimation sequence for a zone, in one embodiment.

With reference to FIG. 8, the temperature, $T_{i,n}$, was estimated in zone 900 $i$, in a site 800 with two zones 900, over a duration of 6 hours.

The temperature, $T_{i,n}$, in zone 900 $i$, at sample n, in units of ° C., is illustrated as the observed temperature, $T_{i,n}$, and the independently estimated temperature, $T_{i,n}^*$, which is related to the temperature in the surrounding environment, $T_{0,n-1}$, temperature in the adjacent zone 900, $T_{1,n-1}$, in units of ° C., energy, $E_{i,c,n}$, in units of J, cloud cover, $c_{i,n-1}$, and solar irradiance, $I_{i,n-1}$, in units of W/m.

Figure 9:
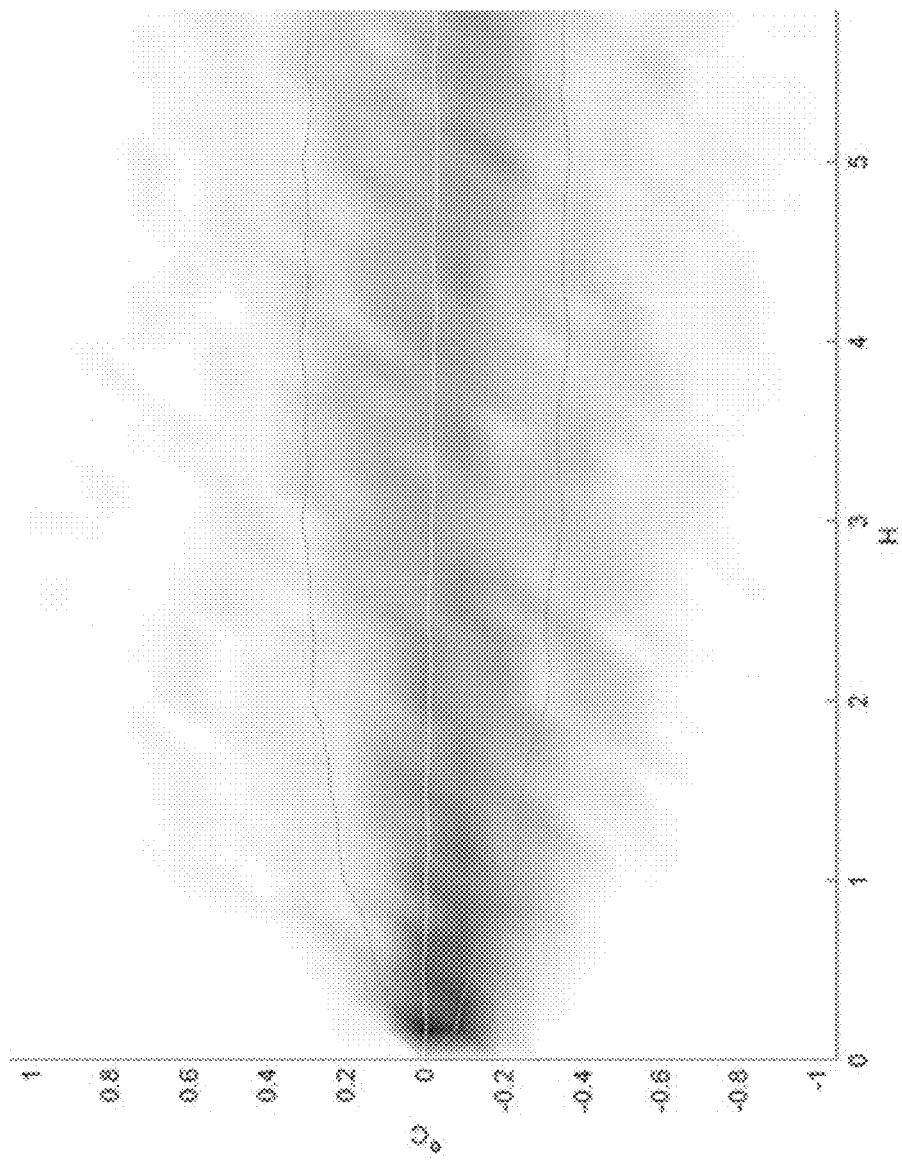
FIG. 9 shows a thermal model forward temperature estimation error sequence for an exemplary zone, in one embodiment.

With reference to FIG. 9, the temperature, $T_{i,n}$, was estimated in zone 900 $i$, in a site 800 with two zones 900, to form overlapping sequences, over a duration of 6 hours, at a period of 1 hour, for 24 hours. Overlaying the temperature estimation sequences in time produces a pattern that can be used to statistically quantify temperature estimation error as a function of time.

In some embodiments, a probability density function, $p_{T^*,i,c,n}$, of forward temperature estimation error, in zone 900 $i$, in cool state c, at sample n, is formed by aggregating errors in estimating temperature, $T_{i,n}$, in zone 900 $i$, at sample n, in units of ° C. The mean, $\mu_{T^*,i,c,n}$, and standard deviation relative to the mean, $\mu_{T^*,i,c,n} \pm \sigma_{T^*,i,c,n}$, corresponding to the sequence of probability density functions, $\bar{p}_{T^*,i,c,n}$, are illustrated in light and dark lines, respectively. In this specific environment, the mean, $\mu_{T^*,i,c,n}$, is approximately zero, and the standard deviation, $\sigma_{T^*,i,c,n}$, slowly increases to approximately 0.3° C. for temperature estimation 6 hours in the future.

Temperature estimation error is implicitly conditionally dependent upon the accuracy of forecast data, including the temperature in the surrounding environment, $T_{0,n-1}$, temperature in the adjacent zone 900, $T_{1,n-1}$, in units of ° C., energy, $E_{i,c,n}$, in units of J, cloud cover, $c_{i,n-1}$, and solar irradiance, $I_{i,n-1}$, in units of W/m.

Reverse Temperature Estimations

The temperature, $T_{i,n-1}$, in zone 900 $i$, at sample n-1, in units of ° C., is defined from the reference, $y_{i,c,n}$, in units of ° C./s, (1.17), as a function of thermal model 600 coefficients, $\omega_{i,j,c,n}$, temperature, $T_{i,n}$, in zone 900 $i$, at sample n, and $T_{j,n}$, in zone 900 $j$, in each of J zones 900 that can share a boundary with zone 900 $i$, including the surrounding environment, at sample n, in units of ° C., energy, $E_{i,c,n}$, in units of J, cloud cover, $c_{i,n}$, solar irradiance, $I_{i,n}$, in units of W/m², and update period, $T_S$, in units of s.

$$T_{i,n-1} = T_{i,n} - T_S \left( \sum_{j=0}^{J-1} \omega_{i,j,c,n}(T_{j,n} - T_{i,n}) + \omega_{i,J,c,n}\left(\frac{E_{i,c,n}}{T_S}\right) + \omega_{i,J+1,c,n}(1 - c_{i,n})I_{i,n} + \omega_{i,J+2,c,n} \right) \quad (1.34)$$

The temperature, $T_{i,n-1}$, in zone 900 $i$, at sample n-1, in units of ° C., is estimated from an observed or estimated temperature, $T_{i,n}$, at sample n, in units of ° C., and the energy, $E_{i,c,n}$, consumed in zone 900 $i$, in cool state c, at sample n, in units of J.

Weather Model

In some embodiments, a weather model 500 is a representation of a weather service 1200, which defines forecast estimations of properties which are associated with a specific region of interest which can include the surrounding environment of a site 800. The weather model 500 estimates future conditions indirectly from a weather service 1200, which provides properties at a default resolution, for example 1 hour, considered to be valid over a weather duration, nominally 24 hours, and a finite geographical range of support that includes a site 800, location, city, region and/or the like. For example, a weather model 500 can have a unique association with a specific region of interest. Weather service 1200 properties can require spatial or temporal interpolation to achieve a specified effective resolution or improve accuracy.

Weather Model Architecture

Figure 10:
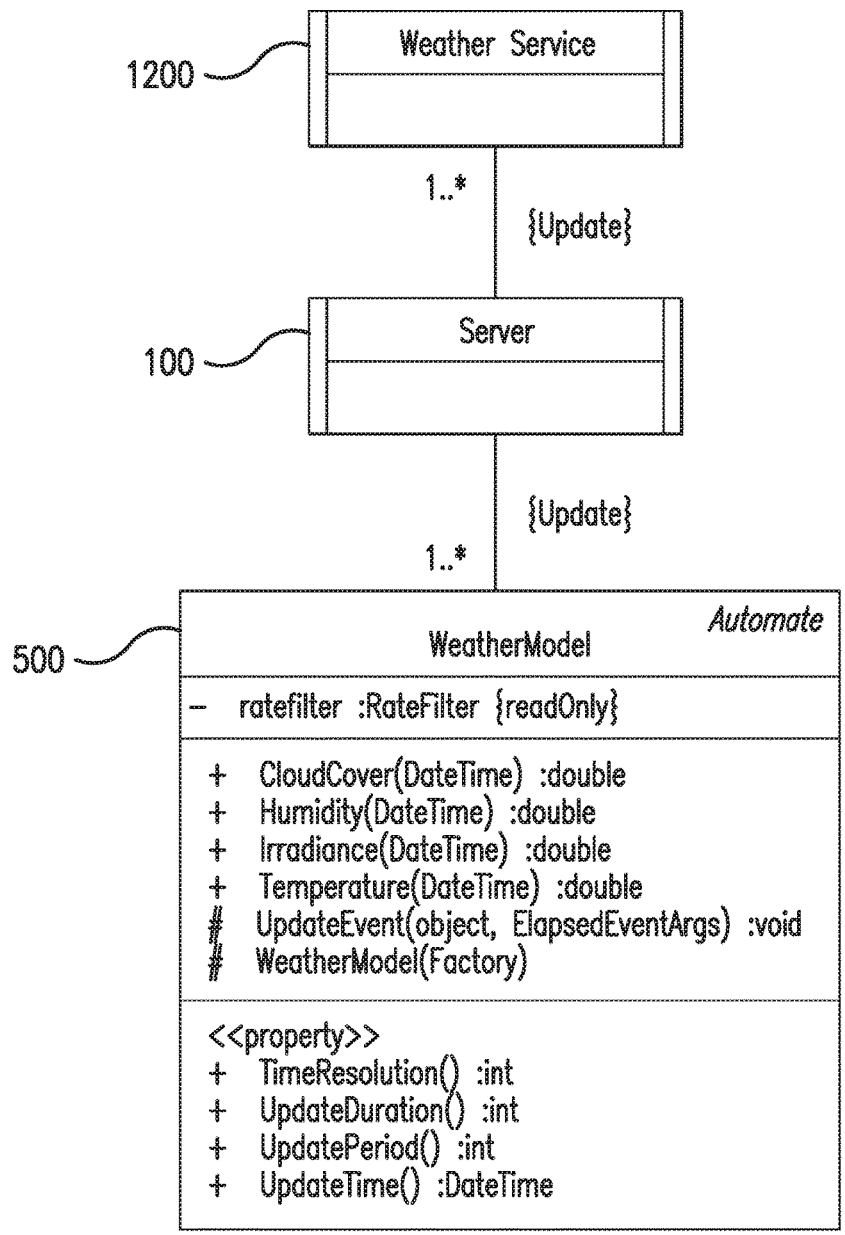
FIG. 10 shows a UML object diagram illustrating a structure and interactions of an exemplary weather model object for a site, in one embodiment.

With reference to FIG. 10, in some embodiments a weather model 500 interacts with a server 100 to indirectly exchange information with a weather service 1200. A weather model 500 defines properties associated with a specific region of interest, such as, but not limited to, cloud cover, humidity, solar irradiance, and/or temperature. Humidity, solar irradiance, and temperature estimation can be provided as a weather model 500 service. A weather model 500 defines events to provide observer notifications, including update(s). Update events are signaled during each update period, for example when a weather model 500 update is complete.

The cloud cover property can be the cloud cover derived from forecast estimations associated with a region, evaluated at a specified time, and normalized to unity range. The humidity property can be the humidity derived from forecast estimations associated with a region, evaluated at a specified time, and normalized to unity range. The irradiance property can be the solar irradiance derived from forecast estimations associated with a region, evaluated at a specified time, in units of W/m². The temperature property can be the temperature derived from forecast estimations associated with a region, evaluated at a specified time, in units of ° C. The time resolution property can be the resolution to which weather service 1200 properties are interpolated to form forecast estimations, nominally 10 minutes, in units of s. The update period property can be the time interval of a weather model 500 update, which corresponds to the interval at which weather service 1200 properties are modified, nominally 1 hour, in units of s. The weather duration property can be the contiguous window of time over which a weather model 500 provides forecast estimations, for example 24 hours, in units of s.

Update of the Weather Model

In some embodiments, a weather model 500 can interpolate a sequence of properties provided from a weather service 1200 in each update period, (e.g., nominally 1 hour), with weather duration, (e.g., nominally 24 hours), to ensure that the effective resolution (e.g., nominally 10 minutes) is sufficient to meet the needs of the application. During each update, sequences of properties can be retrieved with overlapping duration with respect to previous sequences, and estimates can be improved, for example by incorporating recent observations. A weather service 1200 can provide a sequence of forecast estimations of weather model 500 properties, e.g., at a default resolution. A weather model 500 can interpolate weather model 500 properties to an effective resolution in each update period, as necessary.

Alternatively, a weather model 500 can characterize estimations of sequences of forecast estimations of weather model 500 properties by constructing independent models, efficiently encoding temporal sequences in the form of model coefficients, which can be subsequently evaluated to estimate properties at a specified time on demand.

Interpolation

Figure 11:
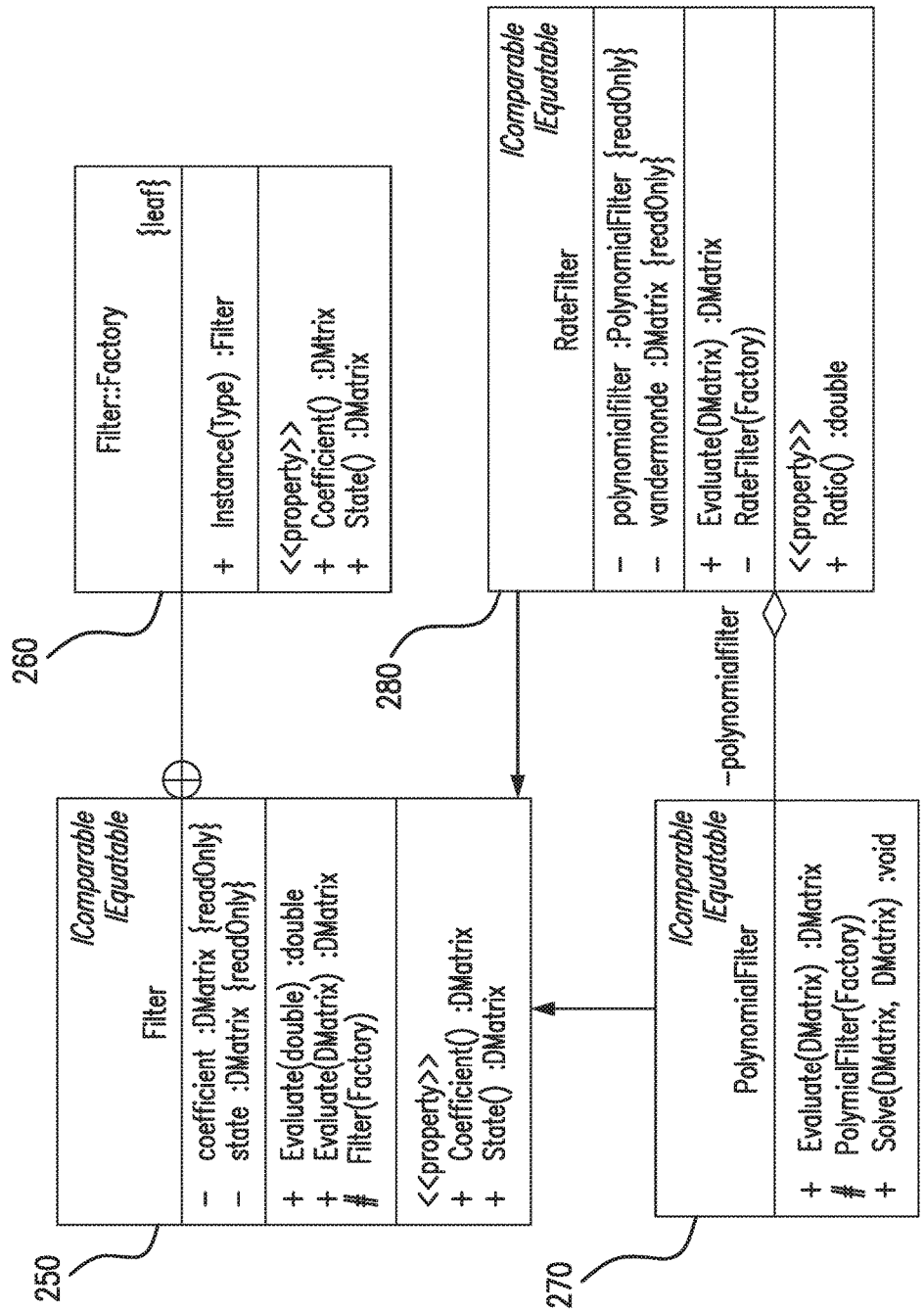
FIG. 11 shows a UML class diagram illustrating the structure of a filter, polynomial filter, and rate filter classes, in one embodiment.

With reference to FIG. 11, a rate filter 280, according to some embodiments, can employ a polynomial filter 270, classes derived from a filter 250, to characterize a sequence of properties and efficiently model the sequence as a vector of polynomial coefficients, which are evaluated at specific times to form an interpolated sequence of properties at an effective resolution. A filter factory 260 is a class which provides a means to construct or retrieve instances of derived concrete types.

The property type, u, can be introduced for notational convenience in the set of cloud cover, humidity, solar irradiance, and temperature, such that the sequence corresponding to each property type, and the corresponding polynomial models characterizing each property, are formed and evaluated independently.

The reference vector, $\bar{y}_{i,u,n}$, associated with region i, of property type u, at sample n, with dimension [N,1], can be formed from N sequential estimations of references, $y_{i,u,m}$, at sample m, where m:[0,N−1]. The incident vector, $\bar{x}_{i,u,n}$, is a sequence of specific times, in units of s, at which corresponding references, $y_{i,u,m}$, are estimated.

The incident matrix, $\bar{X}_{i,u,n}$, associated with region i, of property type u, at sample n, with dimension [N,N], can consist of a Vandermonde matrix, whose elements, $\bar{X}_{i,u,n,j,k}$, at row j and column k, where j, k:[0,N−1], are formed by increasing powers of the incident vector, $\bar{x}_{i,u,n}$.

$$\bar{X}_{i,u,n,j,k} = x_{i,u,n+j}^k \quad (2.35)$$

In some embodiments, the memory duration, N, of the incident matrix, $\bar{X}_{i,u,n}$, and reference vector, $\bar{y}_{i,u,n}$, associated with region i, of property type u, at sample n, is dependent on the default resolution and expected behavior of the property type. A memory duration, N, where N:[4,6] is nominally acceptable, assuming a default resolution of 1 hour, for the property types considered. An even memory duration, N, is preferred, to facilitate symmetry in estimations.

The reference vector, $\bar{y}_{i,u,n}$, associated with region i, of property type u, at sample n, can be equal to the product of the incident matrix, $\bar{X}_{i,u,n}$, and the polynomial coefficient vector, $\bar{p}_{i,u,n}$. The polynomial coefficient vector, $\bar{p}_{i,u,n}$, is indirectly solved by minimizing the $L_2$ error in the linear system.

$$\bar{y}_{i,u,n} = \bar{X}_{i,u,n} \bar{p}_{i,u,n} \quad (2.36)$$

The polynomial coefficient vector, $\bar{p}_{i,u,n}$, associated with region i, of property type u, at sample n, can be directly extracted in increasing order from the product of the inverse of the incident matrix, $\bar{X}_{i,u,n}^{-1}$, and the reference vector, $\bar{y}_{i,u,n}$.

$$\bar{p}_{i,u,n} = \bar{X}_{i,u,n}^{-1} \bar{y}_{i,u,n} \quad (2.37)$$

The polynomial coefficient vector, $\bar{p}_{i,u,n}$, associated with zone 900 i, of property type u, at sample n, can be extracted by explicit matrix inversion, (2.37), as the incident matrix, $\bar{X}_{i,u,n}$, is square, though this technique is computationally more expensive, at $O(N^3)$, and can be numerically less accurate than several alternative methods. The polynomial coefficient vector, $\bar{p}_{i,u,n}$, can be practically solved using methods including, but not limited to, a variant of QR decomposition, single value decomposition, or Gaussian elimination.

The polynomial coefficient vector, $\bar{p}_{i,u,n}$, associated with zone 900 i, of property type u, at sample n, can be independently solved in windows of duration equal to the memory duration, N, by advancing the windows by a duration M, where M:[1,N−1]. Each polynomial coefficient vector is utilized for estimation only over the temporal window immediately preceding the midpoint of the memory duration, N, and corresponding to its duration, M.

Property behavior can be modeled using overlapping windows, increasing estimation accuracy by temporally localizing property characterization, and minimizing edge effects at window transition boundaries.

Estimation

The interpolated references, $\tilde{y}_{i,u,m}$, associated with region i, of property type u, at sample m, are formed by evaluating the polynomial coefficient vector, $\bar{p}_{i,u,n}$, associated with zone 900 i, of property type u, at sample n, where $$m: \left[n + \left\lfloor \frac{N}{2} \right\rfloor - M, n + \left\lfloor \frac{N}{2} \right\rfloor\right],$$

at intervals equal to the effective resolution, $T_S$, in units of s.

$$\tilde{y}_{i,u,m} = \sum_{j=0}^{N-1} \bar{p}_{i,u,n,j} x_{i,u,m}^j \quad (2.38)$$

Figure 12:
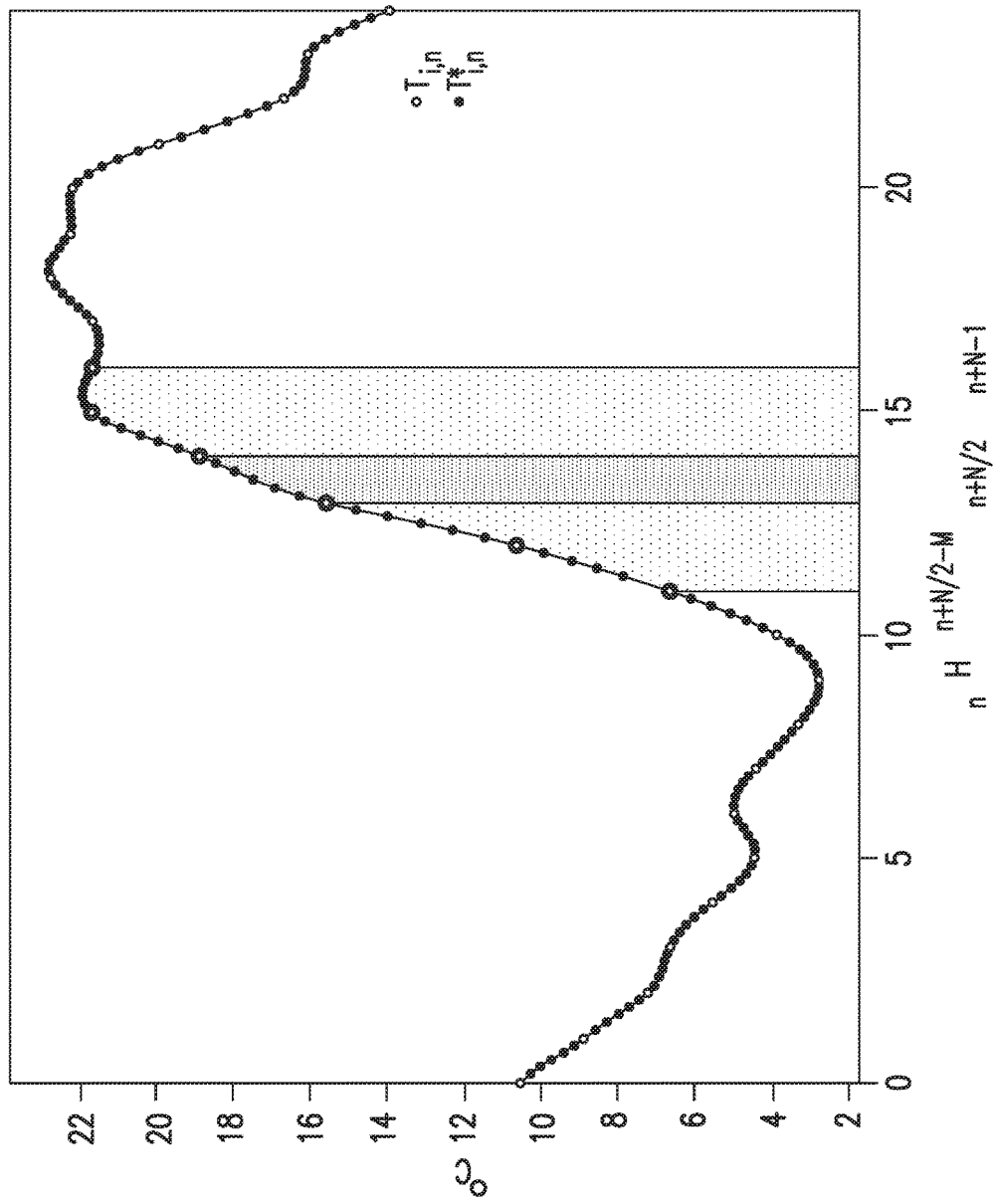
FIG. 12 shows a graph illustrating a weather model temperature estimation sequence for an exemplary site, in one embodiment.

With reference to FIG. 12, the temperature, $T_{i,n}^*$, associated with region i, at sample n, in units of ° C., is estimated at an effective resolution, $T_S$, equal to 10 minutes, from a sequence of temperatures, $T_{i,n}$, at default resolution of 1 hour, over a duration of 24 hours.

The memory duration, N, corresponds to 5 hours, as illustrated by the light shaded window over the range n, where n:[11,16]. Temperatures, $T_{i,n}$, associated with region i, at sample n, constrained within this window, indicated by circles, were used to synthesize a polynomial coefficient vector, $\bar{p}_{i,u,n}$, associated with region i, of temperature property type u, at sample n, which was evaluated at the effective resolution to estimate the temperature, $T_{i,n}^*$, in the dark shaded window over the range m, where m:[13,14].

Comfort Model

A comfort model 400 is a representation of the thermal comfort in a volume in a thermal system, which estimates the effective temperature at which an occupant is unlikely to object, or is implicitly comfortable. One or more comfort models can be used in determining temperatures that minimize energy consumption due to active cooling and/or heating, while maintaining comfort. A thermal system can be generalized as a collection of interdependent volumes and boundaries and a surrounding environment, whose behavior is described by the transfer of mass, work, and heat across the boundaries. A thermal system is defined as a site 800, and each volume, a contiguous region of uniform thermal control, is defined as a zone 900.

In some embodiments, multiple independent temperature profiles are learned from observation of the device temperature, and occupant interactions indicating a preference to lower or raise the temperature, resulting in the synthesis of "minus" events and "plus" events, respectively.

Thermal comfort is a subjective property, and generally may not be quantified with sufficient confidence or rigor to be applied universally with respect to diverse conditions and occupant preferences.

The temperature of a zone 900 is certainly important to assessing thermal comfort. Humidity, ventilation or air flow, clothing, activity level, physical state or condition, and occupancy, can also be useful properties in a comprehensive effort to quantify thermal comfort.

In some instances, properties that are potentially useful in quantifying thermal comfort may not be practically observable or sufficiently complete. Occupancy can be observable, though without explicit knowledge of the specific occupants in a zone 900, their immediate physical states, and their individual preferences, estimating an effective temperature at which all occupants would express similar thermal comfort is not necessarily a reasonable expectation.

In some embodiments, an effort to quantify and learn thermal comfort, by estimating an effective temperature, can be enhanced and simplified by explicit interaction with an occupant, who can elect to indicate whether the temperature subjectively feels too cool or warm. In such embodiments, since commissioning and schedule information are not required, occupant interactions are minimized.

Comfort Model Architecture

Figure 13:
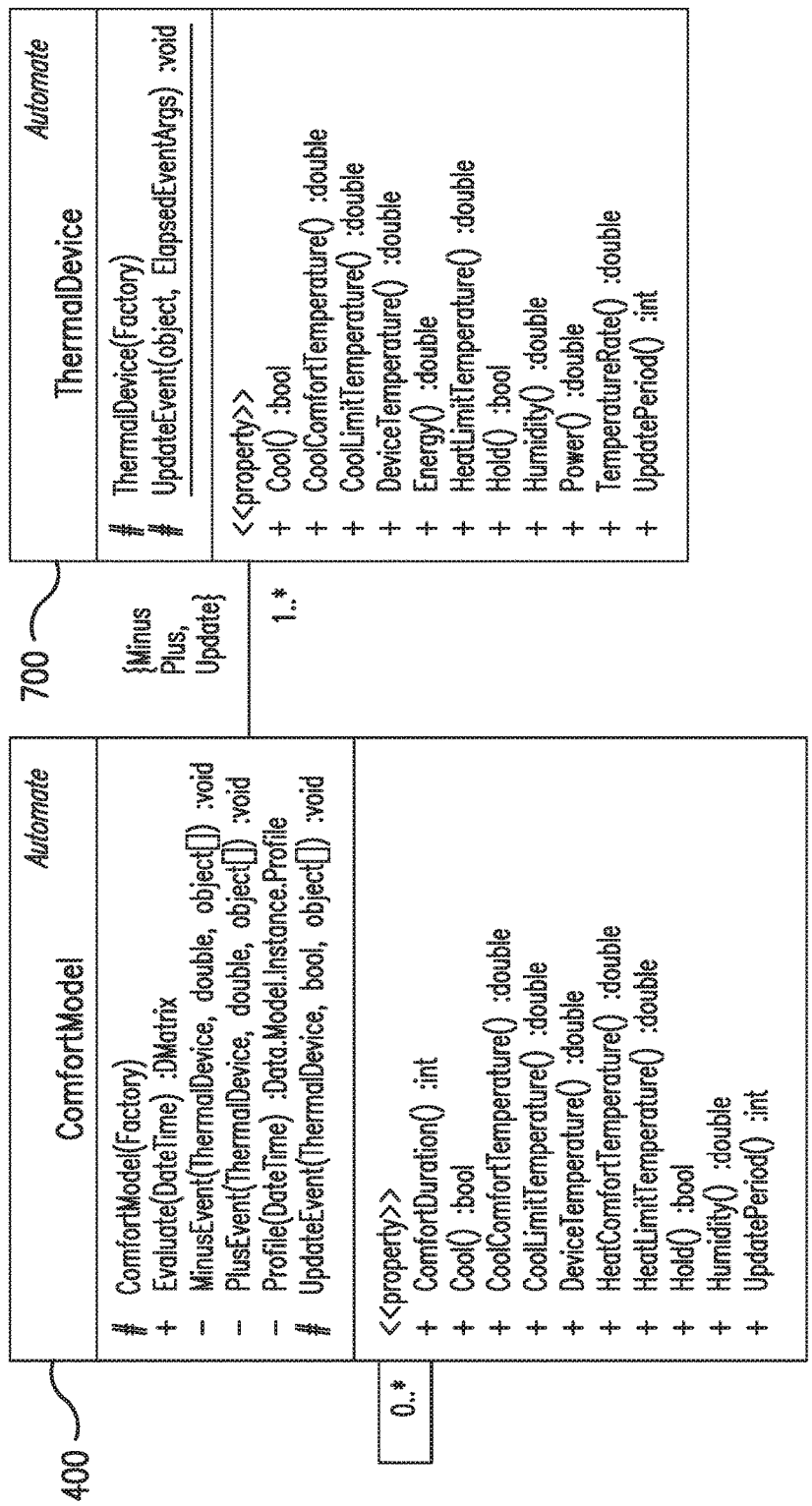
FIG. 13 shows a UML object diagram illustrating a structure and interactions of an exemplary comfort model object for a zone, in one embodiment.

With reference to FIG. 13, a comfort model 400 observes one or more thermal devices 700, and interacts with zero or more comfort models 400 associated with a site 800, according to some embodiments. The comfort model 400 updates properties and events at an update period. The comfort model 400 aggregates thermal device 700 properties and/or events associated with a zone 900 which electively defines multiple thermal devices 700. The aggregation of the thermal device 700 properties and/or events can include filtering, integration, or selection, as appropriate, to form a unified representation of comfort model 400 properties.

The comfort model 400 can interact with zero or more comfort models 400 associated with a site 800. Interaction between the zero or more comfort models 400 associated with a site 800 can be employed for convenience to improve estimation efficiency.

The comfort model 400 can observe thermal device 700 properties associated with a zone 900, and learns multiple independent temperature profiles from observation of the device temperature and occupant interactions. Effective temperature estimation is provided as a comfort model 400 service.

In some embodiments, a comfort model 400 defines properties, including cool, device temperature, hold, and humidity associated with a specific zone 900.

In some embodiments, a comfort model 400 defines events, for example to provide observer notifications, including update(s). Update events are signaled during each update period, for example when a comfort model 400 update is complete.

The comfort duration property is the contiguous window of time over which a comfort model 400 defines a persistent action to improve thermal comfort in response to a minus or plus event, for example nominally 4 hours, in units of s (e.g., 14,400 s.).

The cool property indicates active cooling selection. The cool property is true if the device temperature is greater than or equal to the cool comfort temperature, or if the cool property value from the previous evaluation is true and the device temperature is greater than the heat comfort temperature.

The cool comfort temperature and heat comfort temperature properties define the control temperatures which maximize energy consumption, or the minimum and maximum supported control temperatures, in active cooling and heating, respectively, in units of ° C. The range of temperatures between the cool comfort temperature and heat comfort temperature of a zone 900 form a comfort band in which the occupant is implicitly comfortable.

The cool limit temperature and heat limit temperature properties define the control temperatures which minimize energy consumption, or the maximum and minimum supported control temperatures, in active cooling and heating, respectively, in units of ° C. Temperatures outside of this range can be observed, due the system inactivity or capacity limitations in active cooling or heating relative to environmental conditions, though temperature control outside of this range can be restricted.

The device temperature property is the temperature observed in a zone 900, in units of ° C.

The hold property indicates an occupant preference for manual thermal control.

The humidity property is the humidity observed in a zone 900, normalized to unity range.

The update period property is the time interval of a comfort model 400 update, which corresponds to the update event period of an observed thermal device 700, for example nominally 10 minutes, in units of s (e.g., 600 s.).

Update of the Comfort Model

In some embodiments, a comfort model 400 defines and maintains a collection of temperature profiles, or temporal sequences of temperatures which quantify and learn thermal comfort, each with an epoch of midnight in the local time reference and a duration of 24 hours. A temperature profile is a pattern of temperatures corresponding to a collection of one or more days which have previously been determined to be sufficiently similar in observed occupant behavior that a single temperature pattern is applicable to each day in the collection.

The comfort model 400 can define, by way of example, two temperature profiles, for convenience, one corresponding to a weekday and one corresponding to a weekend. The weekday temperature profile can be active beginning on Monday at 00:00 local time, and until the weekend temperature profile becomes active at 00:00 Saturday morning local time. Precisely one temperature profile is active at any time, though occupant interactions can result in the modification of one or more temperature profiles.

The comfort model 400 can employ a simplifying assumption that the pattern of behavior of an occupant can be sufficiently defined in a collection of temperature profiles, each a collection of days with transitions specified according to a local time reference. Day transition at midnight local time is a convenient assumption, which in some embodiments can be representative of typical occupant behavior.

The comfort model 400 can define temperature profiles with support for temperatures between the heat limit temperature and cool limit temperature. Two temperature regions of support can be defined in each temperature profile, for independent and symmetric operation in active cooling and heating. If the cool property is true, the active region of support is between the cool comfort temperature and cool limit temperature. If the cool property is false, the active region of support is between the heat limit temperature and heat comfort temperature.

The temperature profile can independently define two contiguous persistent sequences, for active cooling and heating, each consisting of reference temperature and erosion temperature, at a resolution equal to the update period, nominally 10 minutes, and a duration of 24 hours. Each sample in the sequence corresponds to a temporal reference of 00:00 local time, and an offset equal to an integral multiple of the update period.

The reference temperature is a temperature sequence which characterizes the preferences of an occupant, defined over some duration of occupant interactions (e.g., historical and/or contemporaneous) and observations.

The erosion temperature is a temperature sequence which represents the offset in temperature applied to opportunistically reduce energy consumption at times when it is determined that an occupant may either not be present in a zone 900, or may be tolerant of reduced thermal comfort. The erosion temperature sign (i.e., the direction, in temperature, of the opportunistic change) is positive if the cool property is true, and negative if it is false.

When a temperature profile is constructed, the reference temperature associated with each region of support is a reference pattern, which can consist of one or more temperatures between the cool comfort temperature and the cool limit temperature, or between the heat limit temperature and the heat comfort temperature, in active cooling or heating, respectively. The erosion temperature associated with each region of support can be initialized to zero.

Exactly one temperature profile is selected to be active, dependent upon the day associations defined in a collection of temperature profiles, at the current time. The active temperature profile can be modified in any update period in which the hold property is false. If the hold property is true, the control temperature is directly modified by the occupant, and inference of the thermal comfort of an occupant in a zone 900 may not be available.

The specific interface of a system which allows an occupant to modify the control temperature when the hold property is true, can be aliased or re-tasked to support occupant interactions which indicate a preference (e.g., a qualitative indication) to lower or raise the temperature, resulting in the synthesis of minus and plus events, respectively, when the hold property is false.

Events

A comfort model 400 can modify the reference temperature, $T_{R,i,c,m}$, and erosion temperature, $T_{O,i,c,m}$, in zone 900 $i$, in cool state c, at sample m, in units of ° C., over a contiguous window of time containing current sample n, in one or more temperature profiles, if a minus or plus event, $E_{M,i,n}$ or $E_{P,i,n}$, occurs, and if the hold state, h, is false.

If a minus event, $E_{M,i,n}$, in zone 900 $i$, at sample n, occurs, an occupant has indicated a preference to lower the temperature. If a plus event, $E_{P,i,n}$, in zone 900 $i$, at sample n, occurs, an occupant has indicated a preference to raise the temperature. A minus or plus event, $E_{M,i,n}$ or $E_{P,i,n}$, can represent an occupant's expression of an intent to increase thermal comfort or to conserve energy, for example depending on the context in which the event occurs. The behavior of a comfort model 400 in response to a minus or plus event, $E_{M,i,n}$ or $E_{P,i,n}$, can be symmetric with respect to active cooling or heating.

If a minus event, $E_{M,i,n}$, in zone 900 $i$, at sample n, occurs, the reference temperature, $T_{R,i,c,m}$, in zone 900 $i$, in cool state c, at sample m, in units of ° C., can be decreased over a range of samples containing the current sample n. One form of modification to the reference temperature, $T_{R,i,c,m}$, consists of applying a fuzzy logic and operation to the device temperature, $T_{i,n}$, minus a reference temperature offset, $T_X$, nominally 1° C., and the reference temperature, $T_{R,i,c,m}$, retaining the minimum.

If a plus event, $E_{P,i,n}$, in zone 900 $i$, at sample n, occurs, the reference temperature, $T_{R,i,c,m}$, in zone 900 $i$, in cool state c, at sample m, in units of ° C., can be increased over a range of samples containing the current sample n. One form of modification to the reference temperature, $T_{R,i,c,m}$, consists of applying a fuzzy logic or operation to the device temperature, $T_{i,n}$, plus a reference temperature offset, $T_X$, nominally 1° C., and the reference temperature, $T_{R,i,c,m}$, retaining the maximum.

The reference temperature, $T_{R,i,c,m}$, in zone 900 $i$, in cool state c, at sample m, in units of ° C., in a temperature profile, can be modified over a contiguous window of time corresponding to a range between the current sample, n, minus a prefix duration, $N^-$, for example nominally 0 hours, and the current sample, n, plus a comfort duration, $N^+$, for example nominally 4 hours.

$$T_{R,i,c,m} = \begin{cases} \text{and } (T_{i,n} - T_X, T_{R,i,c,m}) = E_{M,i,n} \\ \min(T_{i,n} - T_X, T_{R,i,c,m}) \\ \text{or } (T_{i,n} - T_X, T_{R,i,c,m}) = E_{P,i,n} \\ \max(T_{i,n} + T_X, T_{R,i,c,m}) \end{cases} \bigg|_{m:[n-N^-, n+N^+]} \quad (3.39)$$

The erosion temperature, $T_{O,i,c,m}$, in zone 900 $i$, in cool state c, at sample m, in units of ° C., in a temperature profile, is set to zero if any reference temperature, $T_{R,i,c,m}$, is modified over a contiguous window of time corresponding to a range between the current sample, n, minus a prefix duration, $N^-$, for example nominally 0 hours, and the current sample, n, plus a comfort duration, $N^+$, for example nominally 4 hours.

$$T_{O,i,c,m} = 0|_{m:[n-N^-, n+N^+]} \quad (3.40)$$

The reference temperature, $T_{R,i,c,m}$, and erosion temperature, $T_{O,i,c,m}$, in zone 900 $i$, in cool state c, at sample m, in units of ° C., can be modified by linear or non-linear operations, and specific forms are provided for convenience. If a sample m extends across a day transition, and the days are in different temperature profiles, the modification can extend across profile transition. If the days are in the same profile, modulus indexing can be employed across the profile transition to modify the active profile.

The reference recovery behavior of a comfort model 400 in response to a minus event, $E_{M,i,n}$, in active cooling, or a plus event, $E_{P,i,n}$, in active heating, can increase thermal comfort by preserving or modifying the reference temperature, $T_{R,i,c,m}$, while eliminating the cumulative effects of erosion temperature, $T_{O,i,c,m}$, in zone 900 $i$, in cool state c, at sample m, in units of ° C., over a contiguous window of time since a previous minus or plus event, $E_{M,i,n}$ or $E_{P,i,n}$. Conversely, a plus event, $E_{P,i,n}$, in active cooling, or a minus event, $E_{M,i,n}$, in active heating, can reduce energy consumption.

Erosion

In some embodiments, a comfort model 400 modifies the erosion temperature, $T_{O,i,c,n}$, in zone 900 $i$, in cool state c, at sample n, in units of ° C., in the active temperature profile, if a minus or plus event, $E_{M,i,n}$ or $E_{P,i,n}$, has not been received within the comfort duration, $N^+$, the observed state, o, of the effective temperature, $T_{E,i,c,n}$, is true, and the hold state, h, is false. Erosion can be applied at a sample or day resolution.

In some embodiments, a comfort model 400 classifies the observed state, o, of the effective temperature, $T_{E,i,c,n}$, in zone 900 $i$, in cool state c, at sample n, in units of ° C., as true if it is sufficiently proximate to the device temperature, $T_{i,n}$, applying an observe temperature offset, $T_Y$, nominally 1° C., that the effective temperature, $T_{E,i,c,n}$, or a temperature with lower relative thermal comfort, was observed in zone 900 $i$.

$$o = \begin{cases} T_{E,i,c,n} \leq (T_{i,n} + T_Y) & c \\ T_{E,i,c,n} \geq (T_{i,n} - T_Y) & \bar{c} \end{cases} \quad (3.41)$$

In some embodiments, a comfort model 400 does not perform erosion if the effective temperature, $T_{E,i,c,n}$, in zone 900 $i$, in cool state c, at sample n, in units of ° C., is not observed. Erosion may not be reasonably applied if the effective temperature, $T_{E,i,c,n}$, indicates a lower relative thermal comfort than the device temperature, $T_{i,n}$, which was observed, as the assumption of tolerance of reduced thermal comfort by an occupant is not supported.

In some embodiments, the erosion temperature offset, $T_{Z,i,c}$, in zone 900 $i$, in cool state c, in units of ° C., is equal to the product of a specified erosion rate, $$\frac{d}{dt}(T_{Z,i,c}),$$

for example nominally 1.4467593e-6° C./s, or 0.125° C./day, and the sample rate, $T_S$, in units of s, normalized with respect to quantity of days, M, in the temperature profile collection. Rate normalization as specified establishes a consistent maximum erosion rate at any time, on any day, over an interval of one week.

$$T_{Z,i,c} = \frac{d}{dt}(T_{Z,i,c})T_S\left(\frac{M}{7}\right)(2c-1) \quad (3.42)$$

In some embodiments, the erosion temperature, $T_{S,i,c,n}$, in zone 900 $i$, in cool state c, at sample n, in units of ° C., positive in active cooling, and negative in active heating, is modified by adding the erosion temperature offset, $T_{Z,i,c}$, and is limited in range by the difference of the cool or heat limit temperature, $T_{LT,c}$, and the reference temperature, $T_{R,i,c,n}$.

$$T_{S,i,c,n} = \begin{cases} \min(T_{O,i,c,n} + T_{Z,i,c}, T_{LT,c} - T_{R,i,c,n}) & c \\ \max(T_{O,i,c,n} + T_{Z,i,c}, T_{LT,c} - T_{R,i,c,n}) & \bar{c} \end{cases} \quad (3.43)$$

Estimation

The reference temperature, $T_{R,i,c,n}$, and erosion temperature, $T_{S,i,c,n}$, in zone 900 $i$, in cool state c, at sample n, in units of ° C., can be modified in an update process. The utility of the reference temperature, $T_{R,i,c,n}$, and erosion temperature, $T_{S,i,c,n}$, can be found, for example, in the estimation of effective temperature, $T_{E,i,c,n}$, representing thermal comfort.

Temperature

In some embodiments, the effective temperature, $T_{E,i,c,n}$, in zone 900 $i$, in cool state c, at sample n, in units of ° C., is equal to the sum of the reference temperature, $T_{R,i,c,n}$, and erosion temperature, $T_{S,i,c,n}$, and is limited in range by the cool or heat comfort temperature, $T_{CT,c}$, and the cool or heat limit temperature, $T_{LT,c}$.

$$T_{E,i,c,n} = \begin{cases} \max(\min(T_{R,i,c,n} + T_{S,i,c,n}, T_{LT,c}), T_{CT,c}) & c \\ \max(\min(T_{R,i,c,n} + T_{S,i,c,n}, T_{CT,c}), T_{LT,c}) & \bar{c} \end{cases} \quad (3.44)$$

Figure 14:
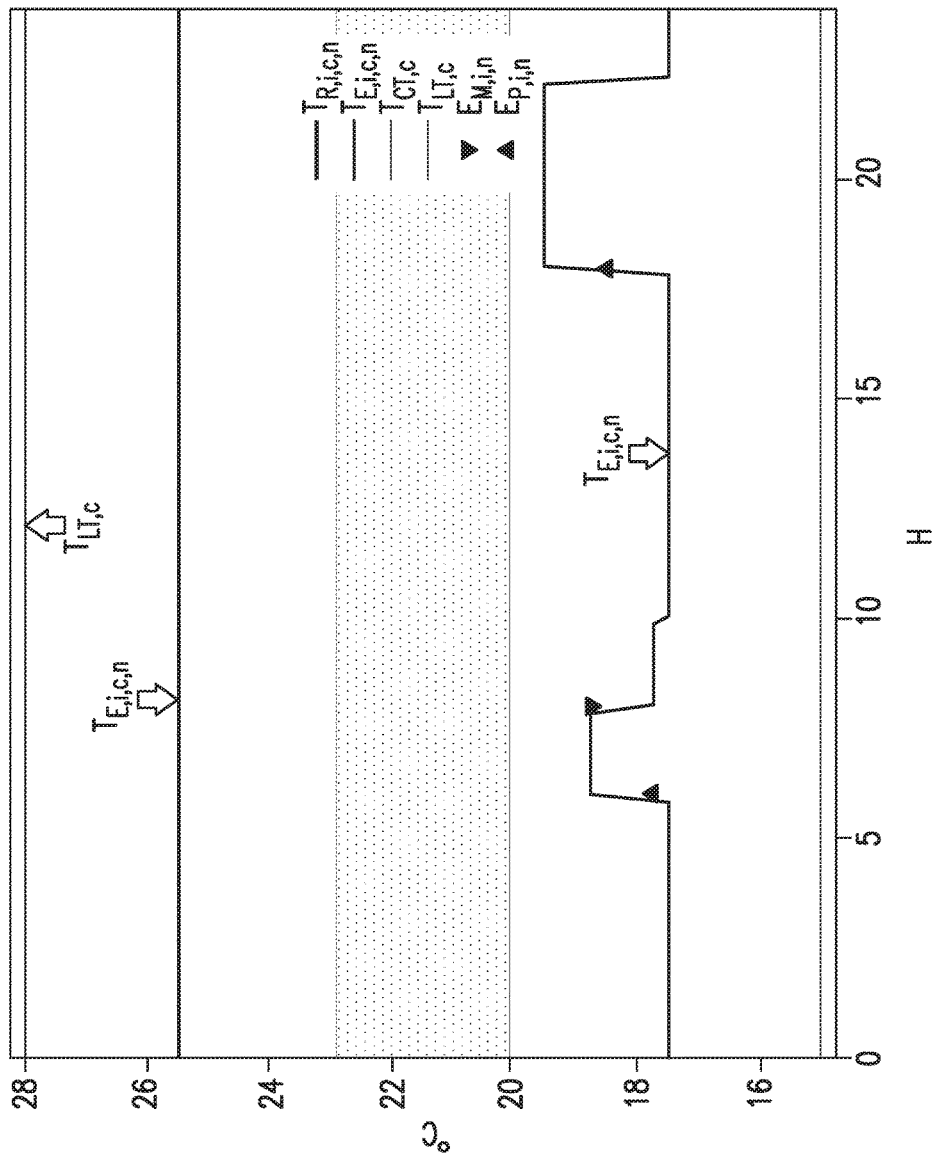
FIG. 14 shows a graph illustrating a comfort model temperature profile with a plus event, a minus event, and a plus event, occurring in active heating, over the course of one day, illustrating event response for an exemplary zone, in one embodiment.

With reference to FIG. 14, a comfort model 400 associated with zone 900 $i$, in a site 800 with two zones 900, according to some embodiments, was initialized with cool and heat comfort temperatures, $T_{CT,c}$, equal to 23.0° C. and 20.0° C., respectively, and cool and heat limit temperatures, $T_{LT,c}$, equal to 28.0° C. and 15.0° C., respectively. The reference temperature, $T_{R,i,c,n}$, in zone 900 $i$, in cool state c, was initialized to the mean of the comfort temperature, $T_{CT,c}$, and limit temperature, $T_{LT,c}$, or 23.5° C. and 17.5° C. A reference temperature offset, $T_X$, of 1° C., and an erosion temperature offset, $T_{Z,i,c}$, of 0.125° C./day, were defined. The comfort model 400 was updated over a duration of 24 hours after initialization, exclusively in active heating, modifying a weekday active temperature profile in response to minus or plus events, $E_{M,i,n}$ or $E_{P,i,n}$.

An occupant indicated a preference to raise the temperature, perhaps after waking, in a plus event, $E_{P,i,n}$, in zone 900 $i$, at sample n, corresponding to 06:00 local time. The device temperature, $T_{i,n}$, in zone 900 $i$, at sample n, was 17.75° C., causing the reference temperature, $T_{R,i,c,m}$, to increase to 18.75° C., until 10:00 local time, the maximum of the reference temperature, $T_{R,i,c,m}$, and the device temperature, $T_{i,n}$, plus reference temperature offset, $T_X$, at each sample m, over a comfort duration, $N^+$.

An occupant indicated a preference to lower the temperature, perhaps before leaving, in a minus event, $E_{M,i,n}$, in zone

900 $i$, at sample n, corresponding to 08:00 local time. The device temperature, $T_{i,n}$, in zone 900 $i$, at sample n, was 18.5° C., causing the reference temperature, $T_{R,i,c,m}$, to decrease to 17.75° C., until 10:00 local time, and to 17.5° C., until 12:00 local time, the minimum of the reference temperature, $T_{R,i,c,m}$, and the device temperature, $T_{i,n}$, minus reference temperature offset, $T_X$, at each sample m, over a comfort duration, $N^+$.

An occupant indicated a preference to raise the temperature, perhaps after returning, in a plus event, $E_{P,i,n}$, in zone 900 $i$, at sample n, corresponding to 18:00 local time. The device temperature, in zone 900 $i$, at sample n, was 18.5° C., causing the reference temperature, $T_{R,i,c,m}$, to increase to 19.5° C., until 22:00 local time.

Figure 15:
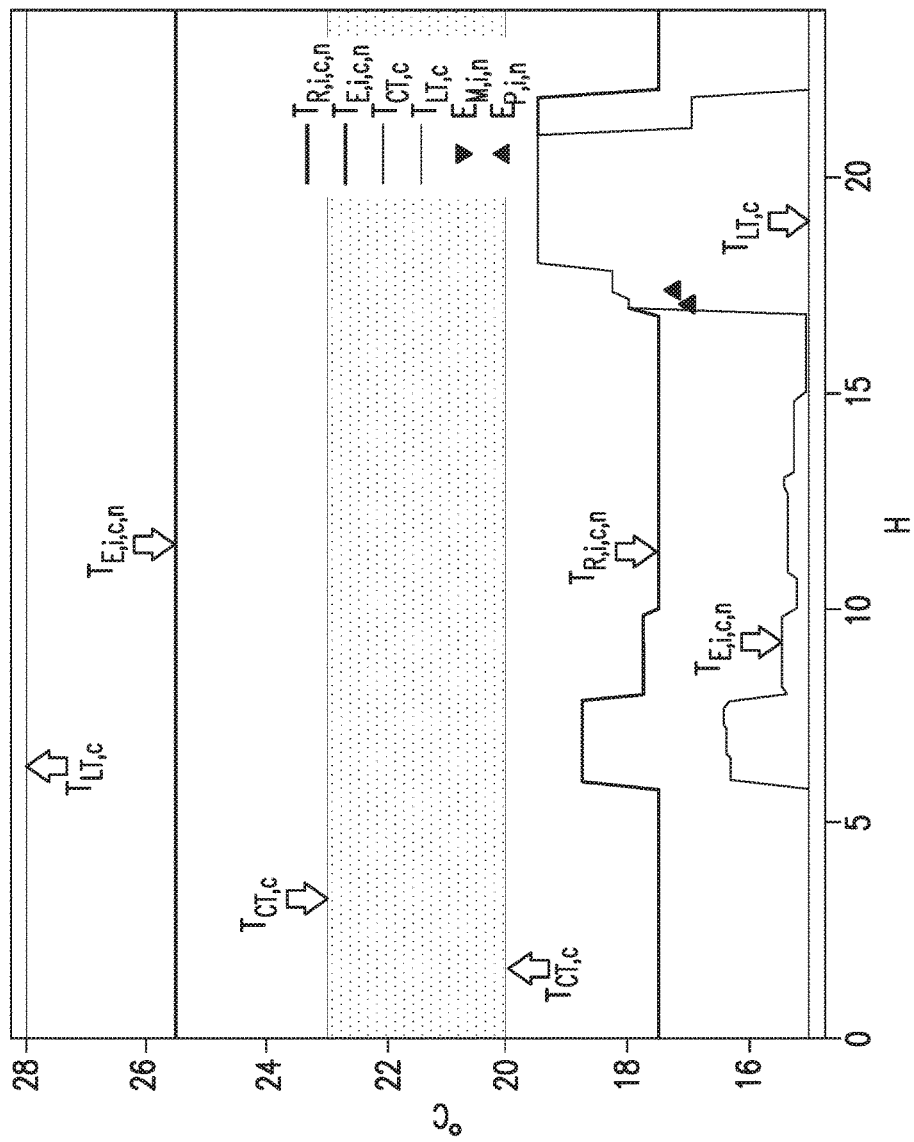
FIG. 15 shows a graph illustrating a comfort model temperature profile with two plus events, occurring in active heating, over the course of one day, illustrating reference recovery for an exemplary zone, in one embodiment.

With reference to FIG. 15, a comfort model 400 associated with zone 900 $i$, in a site 800 with two zones 900, was updated over a duration of several days, exclusively in active heating. The erosion temperature, $T_{S,i,c,m}$, was decreased as applicable. The weekday active temperature profile was modified as illustrated, in response to minus or plus events, or $E_{P,i,n}$, over a duration of 24 hours.

An occupant indicated a preference to raise the temperature, perhaps after returning, as illustrated by a plus event, $E_{P,i,n}$, in zone 900 $i$, at sample n, corresponding to 17:00 local time. The device temperature, $T_{i,n}$, in zone 900 $i$, at sample n, was 17.0° C., causing the reference temperature, $T_{R,i,c,m}$, to increase to 18.0° C., until 18:00 local time, and to 19.5° C., until 21:00 local time. The comfort model 400 response to the plus event, $E_{P,i,n}$, illustrates both a persistent increase in the reference temperature, $T_{R,i,c,m}$, and reference recovery, or restoration of a previously established reference temperature, $T_{R,i,c,m}$.

An occupant indicated a preference to raise the temperature, perhaps due to impatience, as illustrated by a plus event, $E_{P,i,n}$ in zone 900 $i$, at sample n, corresponding to 17:20 local time. The device temperature, $T_{i,n}$, in zone 900 $i$, at sample n, was 17.25° C., causing the reference temperature, $T_{R,i,c,m}$, to increase to 18.25° C., until 18:00 local time, and to 19.5° C., until 21:20 local time.

In FIG. 14 and FIG. 15, a comfort model 400 operated exclusively in active heating, and the region of support for active cooling was unmodified, though the preceding discussion is relevant and applicable to active cooling, as operation is symmetric.

Comfort Agent

In some embodiments, a comfort agent 300 interacts with thermal models 600 to estimate physically realizable discrete temperature states with associated transition values, constrained by comfort model 400 effective temperature estimates, to identify an optimal path and define control temperatures for each volume in a thermal system, facilitating optimal start and deterministic temperature control. A thermal system can be generalized as a collection of interdependent volumes and boundaries and a surrounding environment, whose behavior is described by the transfer of mass, work, and heat across the boundaries. A thermal system is defined as a site 800, and each volume, a contiguous region of uniform thermal control, is defined as a zone 900.

The comfort agent 300 can use thermal models 600 to estimate physically realizable discrete temperature states over a comfort duration, by estimating temperature as a function of energy consumption, in the form of a collection of interconnected states with associated transition values. The states within a collection can be constrained by the effective temperatures estimated by comfort models 400.

The comfort agent 300 can identify an optimal path through the collection which minimizes a cost function in terms of energy, power, current, temperature, financial resources, social resources, resource availability, and/or time, in any units or range, respecting established constraints. Financial resources can include currency, credits, rebates, and/or any other direct or indirect financial consideration. Social resources can include advertisements, acknowledgements, likes and/or any other direct or indirect social consideration. Constraints can be defined in any denomination suitable for definition of a cost function, and in some embodiments constraints may be absolute and inviolate, or flexible such that violating a constraint is permitted and associated with a cost. Control temperatures can be synthesized for each zone 900 in the site 800 over a control duration, reconciling effective temperatures with an optimal path, facilitating optimal start and deterministic temperature control by thermal control units 1000.

Optimal start refers to the adjustment of control temperatures to cool or heat a zone 900 by advancing the times at which specific effective temperature transitions are applied, to ensure that the device temperature observed at an effective temperature discontinuity which results in increased energy consumption, is approximately equal to the specified effective temperature. Optimal start can compensate for control temperature latency, a dynamic characteristic dependent upon thermal time constants and conditions associated with the site 800 and the surrounding environment.

Comfort Agent Architecture

Figure 16:
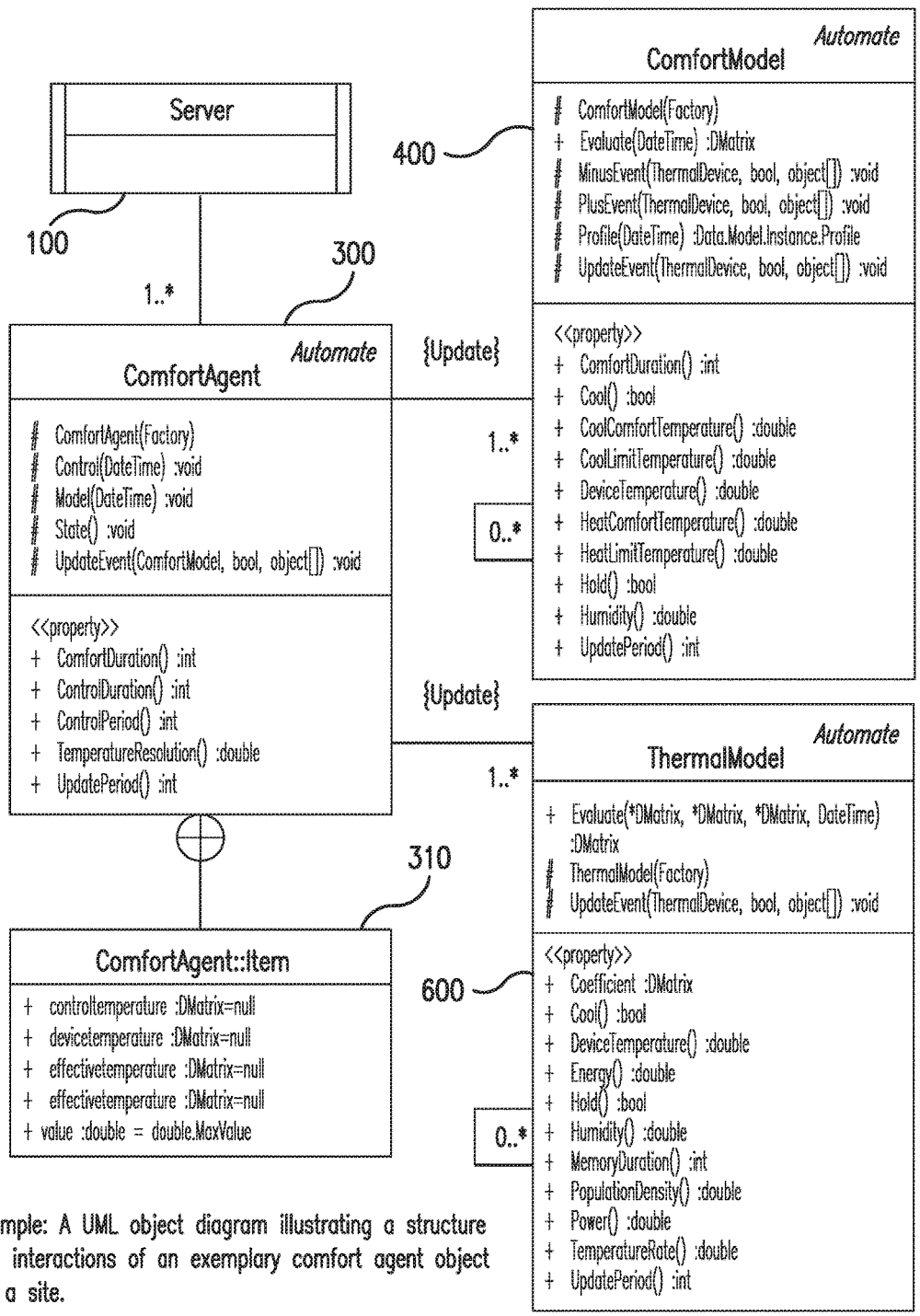
FIG. 16 shows a UML object diagram illustrating a structure and interactions of an exemplary comfort agent object for a site, in one embodiment.

With respect to FIG. 16, in some embodiments a comfort agent 300 interacts with a server 100, and observes one or more comfort models 400 and one or more thermal models 600 associated with a site 800. An item 310 defines representative discrete temperature state properties employed to construct a collection.

A comfort agent 300 observes comfort models 400 and thermal models 600 associated with each zone 900 in a site 800, and reports control temperatures to a server 100, at integral multiples of an update period.

A comfort agent 300 defines properties, including comfort duration, control duration, and control period associated with a specific site 800.

The comfort duration property is the contiguous window of time over which a comfort agent 300 considers thermal model 600 energy and temperature estimations used to define control temperatures, for example nominally 4 hours, in units of s (e.g., 14,400 s.).

The control duration property is the contiguous window of time over which a comfort agent 300 defines control temperatures in a control period, for example nominally 2 hours, in units of s (e.g., 7,200 s.).

The control period property is the maximum time interval at which a comfort agent 300 defines control temperatures, for example nominally 1 hour, in units of s (e.g., 3,600 s.).

The temperature resolution property is the maximum absolute temperature difference in any dimension between an existing state and a candidate state in a collection, evaluated at the same time interval, such that the states are considered sufficiently similar to be merged, in units of ° C., for example nominally 0.05° C.

The update period property is the time interval of a comfort agent 300 update, which corresponds to the update event period of an observed comfort model 400, for example nominally 10 minutes, in units of s (e.g., 600 s.).

Update of the Comfort Agent

In some embodiments, a comfort agent 300 constructs a collection of physically realizable states, each defining a device temperature vector, $T_{u,c,n}$, in state u, in cool state c, at sample n, in units of ° C., an effective temperature vector, $\overline{T}_{E,c,n}$, in units of ° C., and a state value vector, $\overline{s}_{u,c,n}$, in state u, in units of J, retaining the cost of inter-state transitions, or action value vectors, $\overline{q}_{u,v,c,n}$, from state u to state v, in units of J.

A state value vector, $\overline{s}_{u,c,n}$, in state u, in cool state c, at sample n, in units of J, represents the expected cost of being in a specific state, assuming future traversal of an optimal path, expressing the lowest relative cost discounted for time, over an infinite horizon. An action value vector, $\overline{q}_{u,v,c,n}$, from state u to state v, in cool state c, at sample n, in units of J, expresses the immediate cost of traversal from state u to state v. State value vectors, $\overline{s}_{u,c,n}$, and action value vectors, $\overline{q}_{u,v,c,n}$, can be defined in any suitable denomination, including energy, power, current, financial resources, social resources, resource availability, and/or time, in any units or range. The selection of energy, in units of J, can be employed as a matter of convenience.

A collection can have a temporal resolution equal to update period, $T_S$, in units of s, and a temporal range equal to a comfort duration, equivalently N update periods. A site 800 with a zone 900 quantity, J, corresponds to a collection dimension of [J,N], with a computational complexity and state quantity dependent upon the specific type of collection employed, quantization of the action values, $\overline{q}_{u,v,c,n}$, in units of J, with density, V, and temperature resolution, R.

A collection can be expressed as a collection of interconnected states in several suitable forms, such as (but not limited to): a hypercube, a tree, and a mesh. Each state relates a multidimensional temperature, and the energy necessary to transition to a subsequent state, associated with a site 800 with a zone 900 quantity, J.

A hypercube is a collection that expresses scalar states by symmetrically quantizing device temperature, $T_{u,j,c,n}$, in state u, in zone 900 j, in cool state c, at sample n, in units of ° C., and time over a comfort duration, N. A hypercube can populate states at each discrete quantization in temperature and time, with a temperature dimension equal to zone 900 quantity, J, without determining a priori if a state is physically realizable. A hypercube with temperature resolution, R, in units of ° C., scales in computational complexity and state quantity exponentially with respect to zone 900 quantity, J, at:

$$O\left(\left(\left(\frac{|\max(\overline{T}_{CT,c}) - \min(\overline{T}_{E,c,n})|}{R} + 1\right)N\right)^J\right). \quad (4.45)$$

A tree is a collection which can be defined to express only physically realizable vector states, in an asymmetric progression of unique states. A root state transitions to child states which are explicitly defined by quantizing an action value vector, $\overline{q}_{u,v,c,n}$, from state u to state v, in cool state c, at sample n, over a range of available maximum energy, $\overline{E}_M$, in units of J. Energy is, $\overline{E}_M$, uniformly quantized with a density, V, and zone 900 quantity, J, expressing $V^J$ discrete action value vectors, $\overline{q}_{u,v,c,n}$, for each state. Child states are only created if temperature constraints are not violated, in a context dependent progression. Each parent state expresses [0,$V^J$] child states. An unconstrained tree scales exponentially with both zone 900 quantity, J, and comfort duration, N, at $$O\left(\frac{V^{JN} - 1}{V^J - 1}\right).$$

In practice, application of temperature constraints results in significantly reduced populations.

A mesh is a collection which can be defined to express only physically realizable vector states, in an asymmetric progression of unique and merged states. A root state transitions to child states which are explicitly defined by quantizing an action value vector, $\overline{q}_{u,v,c,n}$, from state u to state v, in cool state c, at sample n, over a range of available maximum energy, $\overline{E}_M$, in units of J. Energy is, $\overline{E}_M$, uniformly quantized with a density, V, and zone 900 quantity, J, expressing $V^J$ discrete action value vectors, $\overline{q}_{u,v,c,n}$, for each state.

In a mesh, child states are only created if temperature constraints are not violated, and if the candidate child state is not sufficiently similar to an existing child state, in a context dependent progression. Each parent state expresses [0,$V^J$] child states. A candidate child state is merged with an existing child state at sample n, independent of their parent states, in lieu of creating a new state, if their respective device temperature vectors, $T_{v,c,n}$ and $T_{k,c,n}$, in units of ° C., are sufficiently similar.

A mesh opportunistically merges similar states, which significantly reduces the computational complexity and state quantity, relative to a tree, and often expresses approximately linear order, depending upon environment conditions and the invocation of temperature constraints. Relative to a tree, a mesh introduces additional quantization error, dependent upon the temperature resolution, R, in units of ° C., employed in the merge criterion. Judicious selection of merge criterion minimizes quantization error, and allows a mesh to be practically employed in environments where alternative collections, including a hypercube and a tree, are prohibitive in a computational or storage context.

In some embodiments, a comfort agent 300 update is defined to occur at a maximum control period, for example nominally 1 hour, in units of s (e.g., 3,600 s.), or at integral multiples of update period, $T_S$, for example nominally 10 minutes, in units of s (e.g., 600 s.), when one of several conditions are observed. A comfort agent 300 update occurs when a cool state, c, comfort temperature, $T_{CT,c}$, or limit temperature, $T_{LT,c}$, is modified, or when a minus or plus event, $E_{M,i,n}$, or $E_{P,i,n}$, respectively, is observed in any zone 900 in a site 800.

Figure 17:
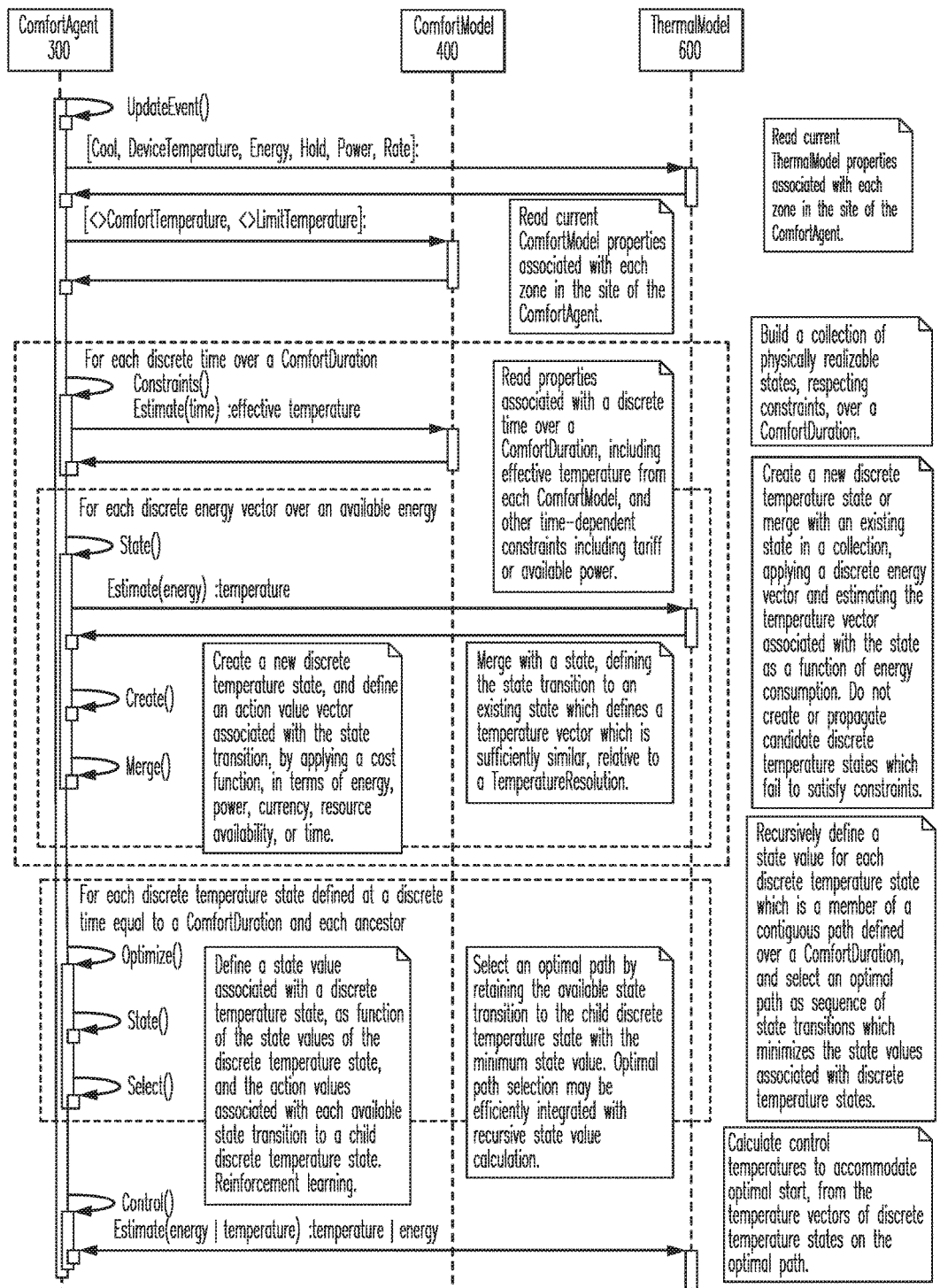
FIG. 17 shows a UML sequence diagram illustrating an update event of a comfort agent object for a site, in one embodiment.

With respect to FIG. 17, a comfort agent 300 observes one or more comfort models 400, and one or more thermal models 600 associated with a site 800, in an update event.

Collection

In some embodiments, a collection can be iteratively constructed from a root state, at the current device temperature vector, $T_{u,c,n}$, in state u, in cool state c, at sample n, in units of ° C., over a comfort duration, N.

In each state, u, at sample n, a thermal model 600 is employed to estimate candidate child state device temperature vectors, $T_{v,c,n+1}$, in state v, in cool state c, at sample n+1, in units of ° C., in terms of an action value vector, $\overline{q}_{u,v,c,n}$, from state u to state v, in cool state c, at sample n, in units of J. The action value vector, $\bar{q}_{u,v,c,n}$, with density, V, and zone 900 quantity, J, represents $V^J$ discrete quantized scaled combinations of available maximum energy, $\bar{E}_M$, in units of J.

A root state, u, is created with a device temperature vector, $T_{u,c,n}$, in state u, in cool state c, at sample n, in units of °C., equal to the current device temperature, $T_{c,n}$.

$$\bar{T}_{u,c,n} = \bar{T}_{c,n} \quad (4.46)$$

A candidate child state, v, is created by employing a thermal model 600 to provide a forward estimate of the device temperature, $T_{v,c,n+1}$, in state v, in cool state c, at sample n+1, in units of °C., relative to the parent device temperature, $T_{u,c,n}$, at each of $V^J$ action state vectors, $\bar{q}_{u,v,c,n}$, from state u to state v, in units of J.

$$\bar{T}_{v,c,n+1} = \bar{T}_{u,c,n} + \frac{d}{dn}(\bar{T}_{u,c,n}):\bar{q}_{u,v,c,n} = \bar{E}_{u,v,c,n}\Big|_{\substack{v:[0,V^J) \\ n:[0,N-1)}} \quad (4.47)$$

Action state vectors, $\bar{q}_{u,v,c,n}$, from state u to state v, in cool state c, at sample n, in units of J, are constructed at each of $V^J$ possible discrete quantized energy vectors, $\bar{E}_{u,v,c,n}$, distributed over a range of available maximum energy, $\bar{E}_{M,c}$, in cool state c, in units of J, equal to the product of the available maximum power vector, $\bar{P}_{M,c}$, in units of W, and update period, $T_S$, in units of s.

$$\bar{q}_{u,v,c,n} = \bar{E}_{u,v,c,n} = \left(\frac{v}{V-1}\right)\bar{P}_{M,c}T_S = \left(\frac{v}{V-1}\right)\bar{E}_{M,c}\Big|_{\substack{v:[0,V^J) \\ n:[0,N-1)}} \quad (4.48)$$

In some embodiments, a temperature constraint is defined such that the candidate child state device temperature vector, $T_{v,c,n}$, in state v, in cool state c, at sample n, in units of °C., must not exceed the temperature range of the comfort temperature, $T_{CT,c}$, in cool state c, and the effective temperature vector, $\bar{T}_{E,c,n}$, for any zone 900 in a site 800. This constraint represents the time dependent range of control temperature, $T_{C,n}$, specified by a comfort agent 300, in active cooling or heating operation.

If a candidate device temperature vector, $T_{v,c,n}$, is sufficiently similar to an existing child state device temperature, $T_{k,c,n}$, for any of K existing child states, at sample n, the candidate child state, v, is merged with an existing child state, k, by defining a new state transition, if an equivalent state transition does not already exist, and discarding the candidate child state, v. If the parents of the candidate child state, v, and existing child state, k, are not the same, the child states are merged and a state transition is constructed between the parent of the candidate child state, u, and the existing child state, k.

A candidate child state, v, can be merged with existing child state, k, for any of K existing child states, if the error temperature, $e_{v,k,c,n+1}$, from state v to state k, in cool state c, at sample n+1, in units of °C., equal to the maximum absolute difference in candidate child state device temperature, $T_{v,c,n+1}$, and existing child state device temperature, $T_{k,c,n+1}$, over each of J zones 900, is less than or equal to a temperature resolution, $T_R$, in units of °C.

$$e_{v,k,c,n+1} = \max(|T_{v,j,c,n+1} - T_{k,j,c,n+1}|)_{\substack{v:[0,V^J) \\ k:[0,K) \\ j:[0,J) \\ n:[0,N-1)}} \leq T_R \quad (4.49)$$

It can be useful to retain a collection of references to unique child states at the same sample, n. Only child states at the same sample, n, need to be considered when evaluating merge constraints. The collection is initially populated with the root state, and repopulated with unique newly constructed child states at each sample n, where n:[0,N).

An effective temperature, $T_{E,c,n+1}$, in cool state c, at sample n+1, in units of °C., is retained for each time sample in which at least one child state exists.

A collection is completed by constructing $[0,V^J]$ child states, v, for each parent state, u, at sample n, over a comfort duration, N, opportunistically discarding or merging candidate child states to comply with temperature and merge constraints.

Optimization

In some embodiments, a comfort agent 300 identifies an optimal path through a collection, considering only child states, v, at sample N-1, and each of their parent states, u, iterating through each sample index in the collection until reaching the root state.

Parent states at sample n that are not successful in creating direct descendant states at sample N-1 can electively be recursively discarded, though it is often convenient to retain and ignore terminal states rather than expend the effort required to identify and discard them.

It can be useful to retain a collection of references to unique parent states at the same sample, n. Only parent states at the same sample, n, need to be considered when evaluating state vector values, $\bar{s}_{u,c,n}$. The collection is initially populated with the child states at sample n equal to the comfort duration, N, and is repopulated with unique parent states at each sample n, where n:[N-1,0).

A state value vector, $\bar{s}_{v,c,N-1}$, in state v, in cool state c, at sample N-1, in units of J, represents the expected cost of being in a state at the terminus of the comfort duration, N, or window of observation, can be assigned any appropriate value which represents the cost of being in the state, assuming that all future state traversals are optimal, and discounted in time over an infinite horizon. A state value vector, $\bar{s}_{v,c,N-1}$, can electively be initialized, for example, as a ratio of an available maximum energy vector, $\bar{E}_{M,c}$, in cool state c, in units of J, scaled by a temperature dependent anticipated duty cycle, $\bar{D}_v$, and the complement of gamma, $\gamma$, a property which defines an exponential time discount rate.

$$\bar{s}_{v,c,N-1} \approx \left(\frac{(\bar{D}_v \bar{1})\bar{E}_{M,c}}{1-\gamma}\right) \quad (4.50)$$

A state value vector, $\bar{s}_{v,c,N-1}$, in state v, in cool state c, at sample N-1, in units of J, can require heuristic initialization, for each state at sample N-1, as a finite window of observation is employed, causing uncertainty regarding future possible states and their associated costs.

A deterministic and recursive method, an application of reinforcement learning, is employed to define remaining requisite state value vectors, $\bar{s}_{u,c,n}$, in state u, in cool state c, at sample n, where n:[0,N), in units of J.

A state value vector, $\bar{s}_{u,c,n}$, in state u, in cool state c, at sample n, in units of J, is equal to the sum of child state value vector, $\bar{s}_{k,c,n+1}$, in state k, in cool state c, at sample n+1, in units of J, whose value is discounted in time by gamma, $\gamma$, and an action value vector, $\bar{q}_{u,k,c,n}$, from state u to state k, in cool state c, at sample n+1, in units of J, such that the resulting state value vector, $\bar{s}_{u,c,n+1}$, expresses the minimum scalar summation, in J zones 900, possible for any child state, v.

$$\bar{s}_{u,c,n} = \bar{q}_{u,k,c,n} + \gamma \bar{s}_{k,c,n+1} : \sum_{j=0}^{J-1}(q_{u,v,k,c,n} + \gamma s_{k,j,c,n+1}) = \quad (4.51)$$

$$\min\left(\sum_{j=0}^{J-1}(q_{u,v,j,c,n} + \gamma s_{v,j,c,n+1})\right)\Bigg|_{\substack{v:[0,V^J)\\k:v\\j:[0,J)\\n:(N-1,0]}}$$

Gamma, $\gamma$, a time discount rate, is equal to the complement of the inverse of memory duration, M, where $\gamma:[0,1)$. The successive application of gamma in estimating a state value vector, $\bar{s}_{u,c,n}$, in state u, in cool state c, at state n, by recursively discounting a constituent future state value vector, $\bar{s}_{v,c,m}$, in state v, in cool state c, at sample m, is exponential.

$$\gamma = 1 - \frac{1}{M}\bigg|_{M>0} \quad (4.52)$$

A state value vector, $\bar{s}_{u,c,n}$, in state u, in cool state c, at sample n, in units of J, (4.51), can be specified to assess the value, or cost, of existing in a specific state defined by a device temperature vector, $T_{u,c,n}$. The specific form defined can be elective, and in some embodiments expresses a cost function in terms of energy. An implicit assumption apparent in this form is that the cost of energy is constant with respect to time, and dynamic tariffs are not supported. A state value vector, $\bar{s}_{u,c,n}$, can be alternatively defined to facilitate dynamic tariffs, or to express cost in any suitable denomination, including energy, power, current, financial resources, social resources, resource availability, and/or time, in any units or range, as a matter of convenience.

A state value vector, $\bar{s}_{u,c,n}$, in state u, in cool state c, at sample n, in units of J, (4.51), is significantly simplified in the specific case where an action value vector, $\bar{q}_{u,v,c,n}$, from state u to state v, is equal to an energy vector, $E_{u,v,c,n}$, in units of J, (4.48), consumed in the state transition, and gamma, $\gamma$, is equal to zero.

$$\bar{s}_{u,c,n} = \bar{q}_{u,k,c,n} + \gamma \bar{s}_{k,c,n+1}\big|_{\gamma=0} = \quad (4.53)$$

$$E_{u,k,c,n} : \sum_{j=0}^{J-1} E_{u,k,j,c,n} = \min\left(\sum_{j=0}^{J-1} E_{u,v,j,c,n}\right)\Bigg|_{\substack{v:[0,V^J)\\k:v\\j:[0,J)\\n:(N-1,0]}}$$

A state value vector, $\bar{s}_{u,c,n}$, in state u, in cool state c, at sample n, in units of J, with gamma, $\gamma$, equal to zero, effectively discounts all future state values, $\bar{s}_{v,c,m}$, completely, so that each state value vector, $\bar{s}_{u,c,n}$, is defined exclusively in terms of an immediate minimum action value vector, $\bar{q}_{u,v,c,n}$, (4.53). Application of this cost function eliminates edge effects caused by a finite window of observation, as future state values, $\bar{s}_{v,c,n}$, are infinitely discounted, and negates the requirement to initialize a state value vector, $\bar{s}_{v,c,N-1}$.

In some embodiments, comfort agent 300 retains a reference to the child state, k, which minimizes the state value vector, $\bar{s}_{u,c,n}$, in state u, in cool state c, at sample n, where n:[0,N), in units of J, (4.51), for each state. A unique optimal path can be identified by traversing the retained sequence of minimum state value vectors, $\bar{s}_{u,c,n}$.

An optimal temperature vector, $T_{O,c,n}$, in cool state c, at sample n, in units of ° C., can be identified from the device temperature vector, $T_{k,c,n}$, in each state along an optimal path:

$$T_{O,c,n} = T_{k,c,n} : \sum_{j=0}^{J-1}(q_{u,v,k,c,n} + \gamma s_{k,j,c,n+1}) = \quad (4.54)$$

$$\min\left(\sum_{j=0}^{J-1}(q_{u,v,j,c,n} + \gamma s_{v,j,c,n+1})\right)\Bigg|_{\substack{v:[0,V^J)\\k:v\\j:[0,J)\\n:(N-1,0]}}$$

An optimal energy vector, $E_{O,c,n}$, in cool state c, at sample n, in units of J, can be identified from the energy vector, $E_{u,k,c,n}$, in each state along an optimal path:

$$E_{O,c,n} = E_{u,k,c,n} : \sum_{j=0}^{J-1}(q_{u,v,k,c,n} + \gamma s_{k,j,c,n+1}) = \quad (4.55)$$

$$\min\left(\sum_{j=0}^{J-1}(q_{u,v,j,c,n} + \gamma s_{v,j,c,n+1})\right)\Bigg|_{\substack{v:[0,V^J)\\k:v\\j:[0,J)\\n:(N-1,0]}}$$

In some embodiments, a control temperature vector, $T_{C,c,n}$, in cool state c, at sample n, in units of ° C., is initially defined to equal an effective temperature vector, $T_{E,c,n}$, in each state along an optimal path. The optimal temperature vector, $T_{O,c,n}$, is traversed over the comfort duration, N, to determine if the control temperature vector, $T_{C,c,n}$, must be modified to facilitate optimal start.

If the optimal temperature vector, $T_{O,c,n}$, in cool state c, at sample n, in units of ° C., has a component, $T_{Oj,c,n}$, in zone 900 j, which is more comfortable than the corresponding effective temperature, $T_{Ej,c,n}$, by a temperature offset, $T_Z$, nominally 0.5° C., and the energy, $E_{Oj,c,n}$, consumed in zone 900 j, in units of J, is not negligible, indicating that active cooling or heating is required, the control temperature, $T_{Cj,c,n}$, is modified by assigning the next effective temperature, $T_{Ej,c,m}$, in which this condition is false. The application of hysteresis or momentum to the decision criterion can reduce transient conditions and improve consistency of the control temperature vector, $T_{C,c,n}$.

The control temperature vector, $T_{C,c,n}$, in cool state c, at sample n, in units of ° C., can be quantized to facilitate deterministic temperature control by thermal control units 1000. Thermal control units 1000 employ hysteresis in relatively high frequency temperature regulation, and can employ nonlinear control behavior, including overshoot correction, minimum run duration, and minimum hold off duration, which may not be observable or predictable by a comfort agent 300. Definition of quasi-stationary segments of control temperature, $T_{C,j,c,n}$, in zone 900 $j$, significantly reduces interference with deterministic temperature regulation.

Figure 18:
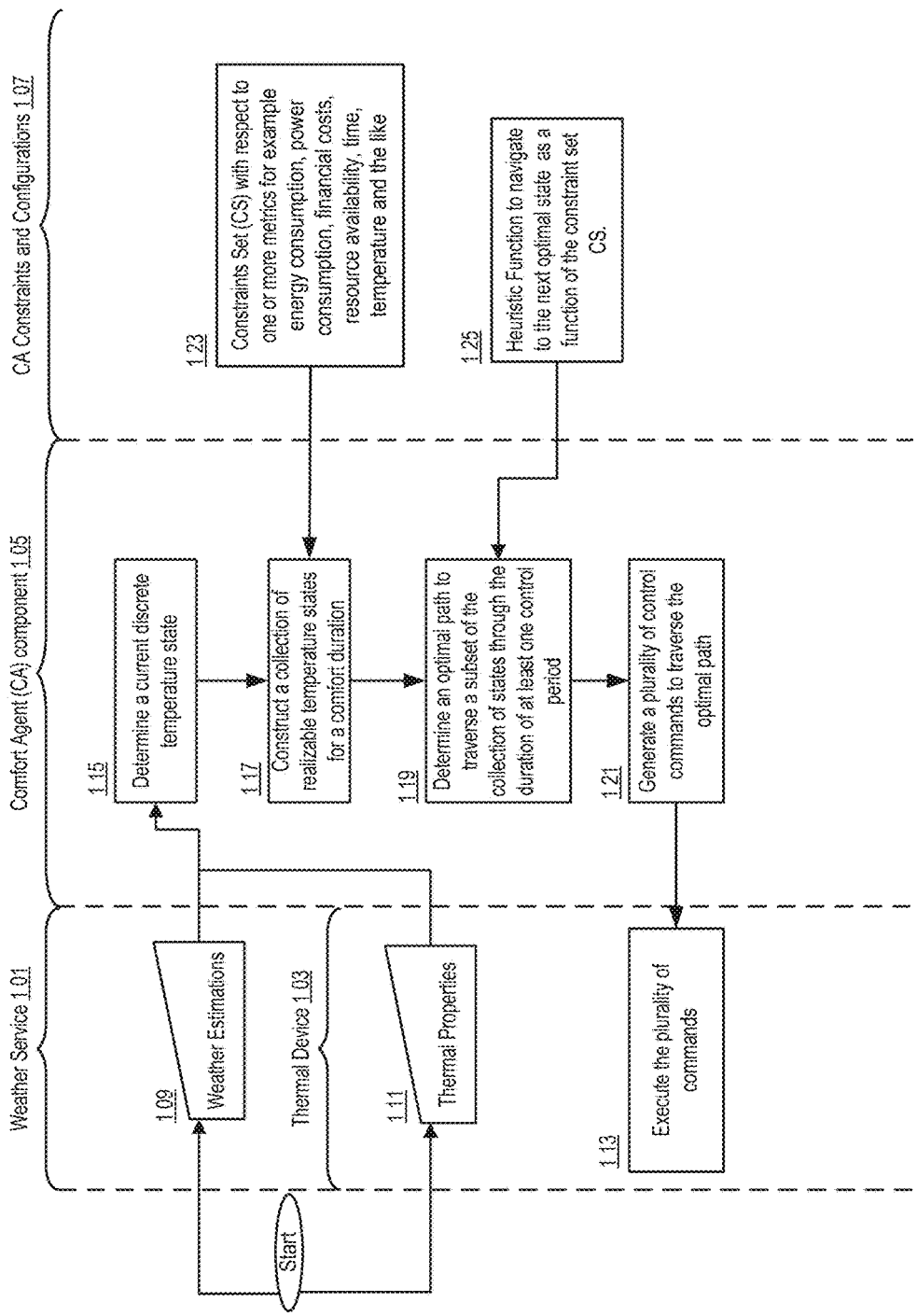
FIG. 18 shows an example of a generation of a plurality of commands to optimally control an environment according to one or more constraints, in one embodiment.

FIG. 18 shows an example of a generation of a plurality of commands to optimally control an environment according to one or more constraints, in one embodiment. In one embodiment, a comfort agent (CA) component 105 can receive weather estimations 109 from a weather service provider 101. For example weather estimations 109 can indicate a cloud cover, humidity, solar irradiance, and/or temperature of one or more areas. Similarly, the CA component can receive a plurality of thermal properties 111 observed by a thermal device 103 including but not limited to cool, coefficient, device temperature, energy consumed in active cooling or heating, hold, power capacity, and temperature rate, associated with a specific zone.

The received weather estimations 109 and thermal properties 111 can be used by the CA component to determine a current discrete temperature state 115. Thereafter, the CA component can construct a collection of realizable temperature states that can be achieved within a period of time or control duration 117. In some embodiments, a realizable temperature can be defined as a temperature that can be physically achieved by controlling a device for example an HVAC and that is not inhibited by an existing constraint, for example, a candidate temperature state can be physically realizable from a current temperature state however, the candidate temperature state may not be chosen as the next state if is constrained by a user's preference, for example, a user's perception of a comfortable temperature.

In some embodiments, a plurality of constraints can be specified in a constraint set including but not limited to temperature constraints, energy efficiency constraints, power consumption constraints, financial costs constraints and the like constraints 123. Thereafter, the CA component 105 can determine an optimal path to traverse a non-constrained subset of the collection of states through the duration of at least one control period 119. In some embodiments, a control period can be defined as a contiguous window of time over which a comfort agent CA component 105 can define or control temperatures in a determined environment.

In some embodiments, an optimal path is determined by utilizing a heuristic function 125. A heuristic function can be defined as a function of a current temperature state, a candidate temperature state and one or more constraints. In some embodiments, a heuristic function can be an estimate or an underestimate of the cost of the shortest path from a current temperature state to a goal temperature state, where the cost can be defined as a measure of how well the one or more constraints are satisfied.

In some embodiments constraints and configurations 107 can be interpreted as complex goals for example reaching a certain temperature at the end of a control period at a minimal financial cost, wherein the rate at which the financial cost is charged can change during the control period. In such a case, the heuristic function can determine when a candidate temperature state leads to an optimal path or optimal global solution even when the candidate temperature state is not a local minimal but, however, due to an emergent property (change of charge rate over time) is a candidate temperature state leading to an optimal global solution.

In some embodiments, once the optimal path is determined, the control agent CA 105 can produce an action plan in the form of a sequence of commands 121 to be executed by a thermal device 103 for example and HVAC to navigate the subset of temperature states comprised in the optimal path during the time specified by the control duration 113.

Figure 19:
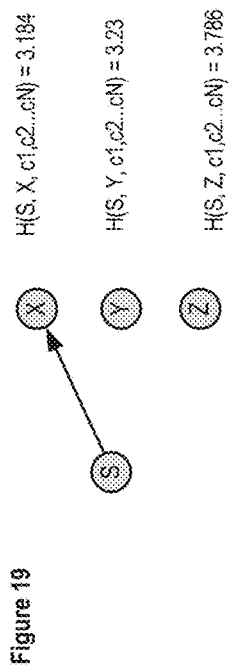
FIG. 19 shows an example of a heuristic as a function of multiple constraints and the identification of an optimal path, in one embodiment.
Figure 20:
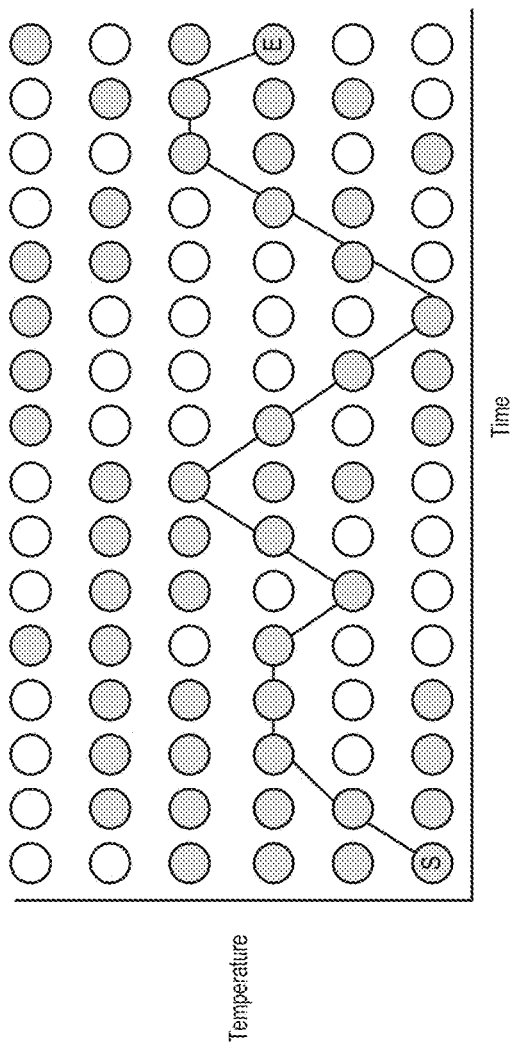
FIG. 20 shows an example of a heuristic as a function of multiple constraints and the identification of an optimal path, in one embodiment.

FIGS. 19 and 20 show examples of heuristics as a function of multiple constraints and the identification of an optimal path, in one embodiment. FIG. 19 shows a stating temperature state S, and three candidate temperature states X, Y and Z. In some embodiments the heuristic function is a function of the current state, a candidate state, and one or more constraints. The heuristic function can inform the CA component 105 of the best candidate temperature state to take considering a set of constraints and configurations. Some constraints can have an associated weight proportional to the impact that they are allowed to have over the global solution. For example, if reducing financial costs is prioritized over users comfort then, financial costs constraints can have a greater weight. In some embodiments, the heuristic function can deal with multiple competing goals. In such a case, the heuristic function can utilized a Pareto analysis and/or the like multiple-objective techniques to determine a best candidate temperature.

FIG. 20, shows an example of an optimal path to traverse from the starting state S to the goal state E. Each circle in the grid represents temperature states. The gray circles represent realizable candidate states (i.e., states that are non-constrained). Therefore, the optimal path must consist of only temperature states represented in gray. In some embodiments, the algorithm determining an optimal path can utilize an irrevocable control strategy based on for example a greedy algorithm or nearest neighbor algorithm, driven by a local minimum. In other embodiments, the CA component 105 can utilize a heuristic representing an underestimate of the remaining cost between a current temperature state and a goal temperature state. Wherein the cost can be defined as a measure of how well the one or more constraints are satisfied. In such a case, a tentative control strategy can be enabled based for example on an A*(A star) algorithm or other type of branch and bound algorithm and/or backtracking algorithm.

Figure 21:
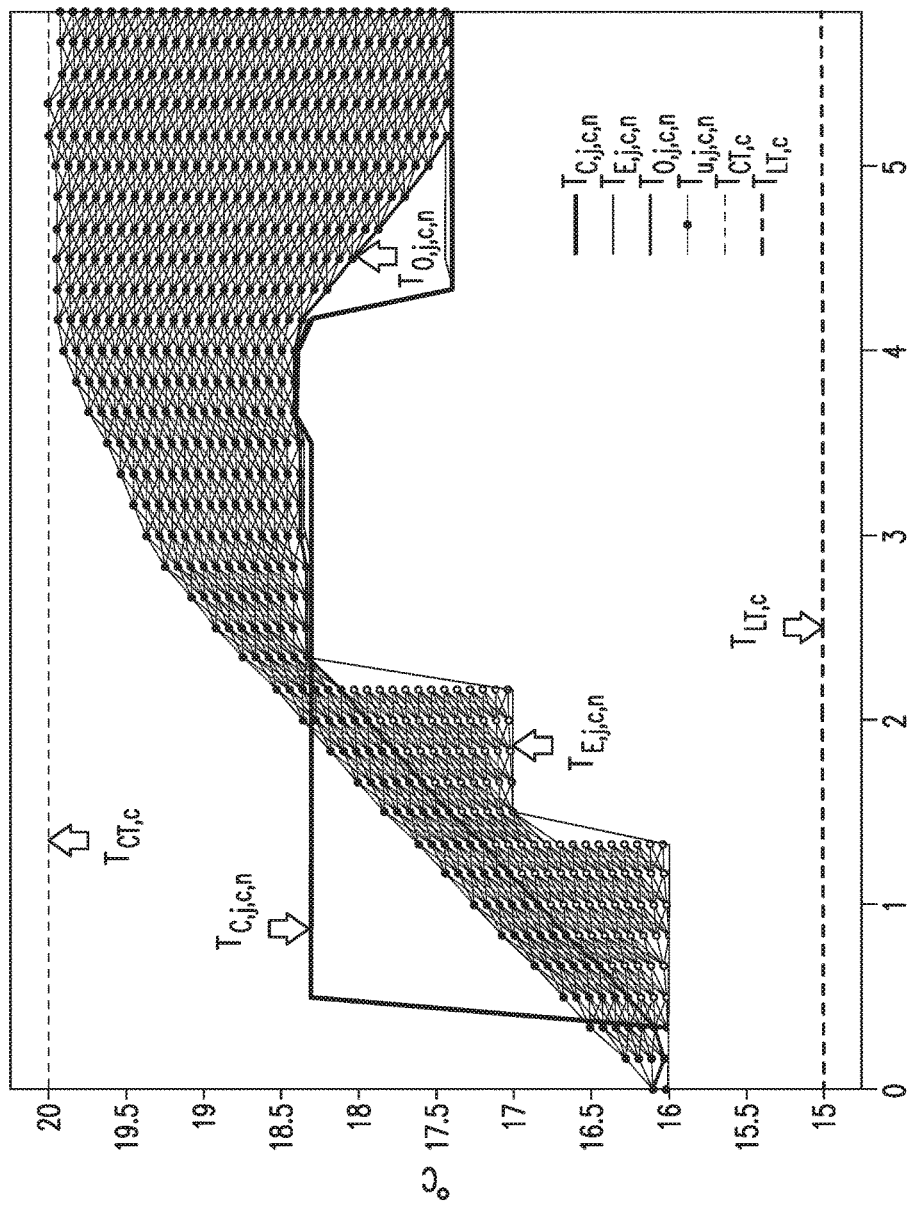
FIG. 21 shows a graph illustrating a comfort agent effective temperature, optimization temperature, and control temperature sequence for a site, in one embodiment.

With respect to FIG. 21, a comfort agent 300 associated with a site 800 with two zones 900, with comfort duration equal to 6 hours, control duration equal to 3 hours, control period equal to 1 hour, and temperature resolution equal to 0.1° C., was initialized and updated over a duration of 20 days, exclusively in active heating. Thermal models 600 in each zone 900 were initialized and updated over the same duration, with a diversity of conditions sufficient to demonstrate quasi-stationary thermal coefficient vector, $\overline{\omega}_{c,n}$, convergence.

Comfort models 400 in each zone 900 were initialized with cool and heat comfort temperatures, $T_{CT,c}$, equal to 23.0 and 20.0° C., and cool and heat limit temperatures, $T_{LT,c}$, equal to 28.0 and 15.0° C., respectively. The reference temperature, $T_{Tj,c,n}$, in zone 900 $j$, in cool state c, at sample n, was initialized to the mean of the corresponding comfort temperature, $T_{CT,c}$, and limit temperature, $T_{LT,c}$, or 23.5 and 17.5° C. The comfort models 400 were updated over a duration sufficient to define weekday active temperature profiles in response to minus or plus events, $E_{M,i,n}$ or $E_{P,i,n}$.

A comfort model 400 defined a weekday temperature profile with effective temperature, $T_{E,j,c,n}$, in zone 900 $j$, in cool state c, at 16.0° C. until 01:30 hours, at 17.0° C. until 02:20 hours, at 18.3° C. until 03:00 hours, at 18.35° C. until 03:40 hours, at 18.4° C. until 04:20 hours, and at 17.4° C. until 06:00 hours, with time relative to the comfort duration.

The comfort agent 300 constructed a collection of states, with density, V, equal to 8, to represent the physically realizable discrete temperature vectors, $T_{u,c,n}$, in state u, in cool state c, at sample n, in units of ° C., and associated energy transitions, $\bar{E}_{u,k,c,n}$, in units of J, constrained by the effective temperature, $T_{E,c,n}$, and the comfort temperature, $T_{CT,c}$, over a comfort duration. Device temperatures, $T_{u,j,c,n}$, in state u, in zone 900 j, in cool state c, at sample n, are projected onto a two-dimensional surface to illustrate a single zone 900 to enhance visualization.

The optimal temperature, $T_{O,j,c,n}$, in zone 900 j, in cool state c, at sample n, in units of ° C., corresponds to the device temperature, $T_{u,j,c,n}$, identified in an optimal path, which minimizes a state value vector, $\bar{s}_{u,c,n}$, in units of J, (4.53). The control temperature, $T_{C,j,c,n}$, reconciles the effective temperature, $T_{E,j,c,n}$, with the optimal temperature, $T_{O,j,c,n}$, facilitating optimal start, at 18.3° C., from 00:30 to 02:20 hours. Terminal states are not considered in the identifying the optimal path, as illustrated by states below the optimal temperature, $T_{O,j,c,n}$, from 00:30 to 02:10 hours.

Figure 22:
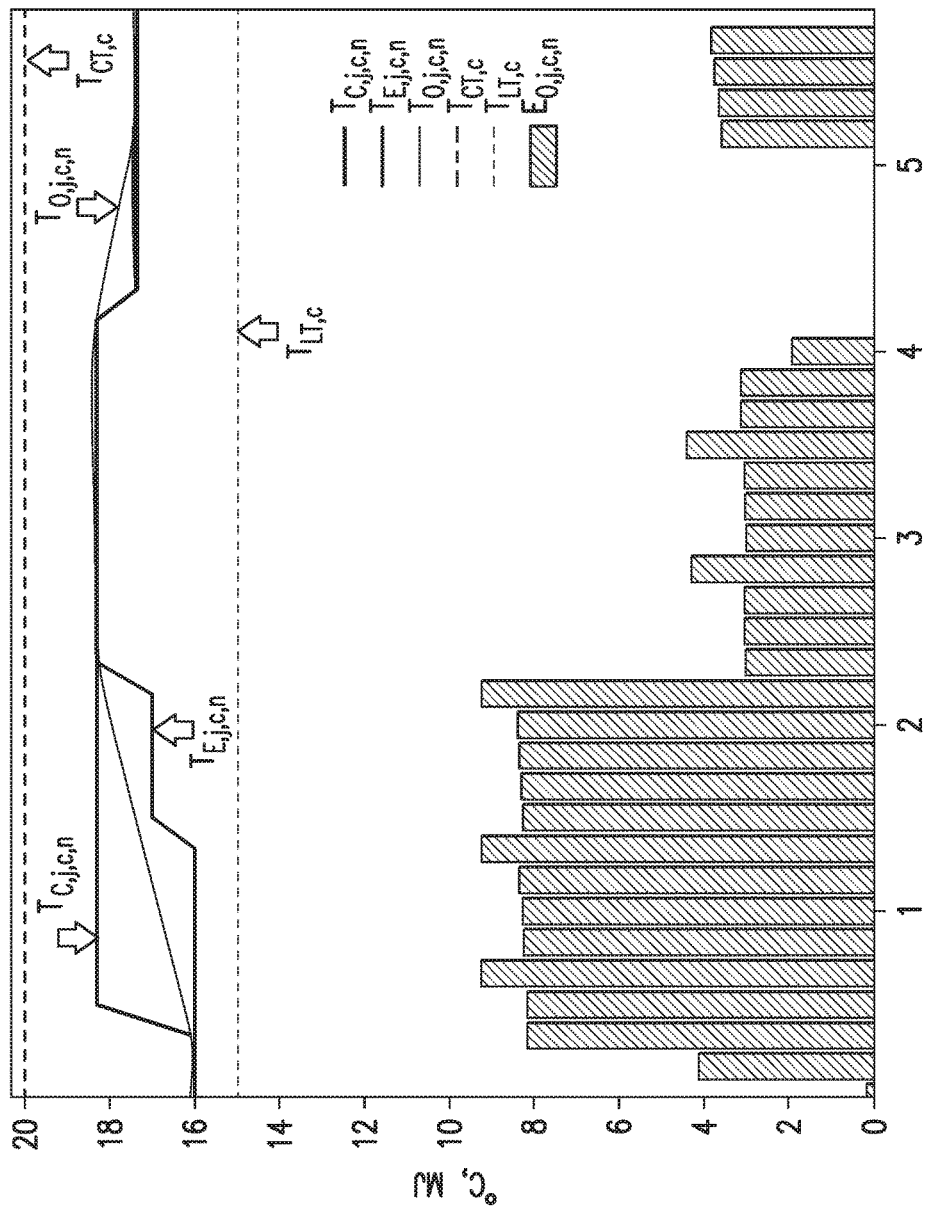
FIG. 22 shows a graph illustrating comfort agent 300 optimization energy for a site, in one embodiment.

With respect to FIG. 22, the optimal energy, $E_{O,j,c,n}$, consumed in zone 900 j, in cool state c, at sample n, in units of J, in a site 800 with two zones 900, illustrates the estimated energy consumption expected if the optimal temperature, $T_{O,j,c,n}$, were utilized as the control temperature, $T_{C,j,c,n}$, over a comfort duration. The optimal energy, $E_{O,j,c,n}$, increases to values approximately equal to the available maximum energy, $E_{M,j,c}$, consumed in zone 900 j, from 00:20 to 02:10 hours, in agreement with previous observations of the control temperature, $T_{C,j,c,n}$, modification necessary to facilitate optimal start.

The optimal energy, $E_{O,j,c,n}$, consumed in zone 900 j, in cool state c, at sample n, in units of J, decreases to approximately 0.4 $E_{M,j,c}$, reflecting the energy required to sustain regulation at a control temperature, $T_{C,j,c,n}$, of 18.3° C., from 02:20 to 04:00 hours, and decreases to approximately 0.0, from 04:10 to 05:00 hours, as the optimal temperature, $T_{O,j,c,n}$, is significantly more comfortable than the effective temperature, $T_{E,j,c,n}$, and active heating is not required.

Optimal start is context dependent, as varied environmental conditions, realizing an identical effective temperature, $T_{E,j,c,n}$, sequence would require a different control temperature, $T_{C,j,c,n}$, solution.

In FIG. 21 and FIG. 22, a comfort agent 300 operated exclusively in active heating, and estimates for active cooling were not calculated, though the preceding discussion is relevant and applicable to active cooling, as operation is symmetric.

Estimation

In some embodiments, relative or absolute energy savings can be determined by comparing accumulated observed energy consumption in a site 800 that exclusively regulates temperature at control temperatures published by a comfort agent 300, to estimated energy consumption at a reference control temperature. The selection of an appropriate reference control temperature to make such a comparison can be heuristic. In some embodiments, the reference control temperature can be a temperature that is likely to have been selected by an occupant if manual temperature control had been utilized over an identical or similar window of observation.

A thermal model 600 can be employed to perform forward energy estimation to define a sequence of reference energy estimates over the window of observation, selecting the comfort temperature, $T_{CT,c}$, in cool state c, as an appropriate constant reference control temperature.

OCO Controller

Figure 23:
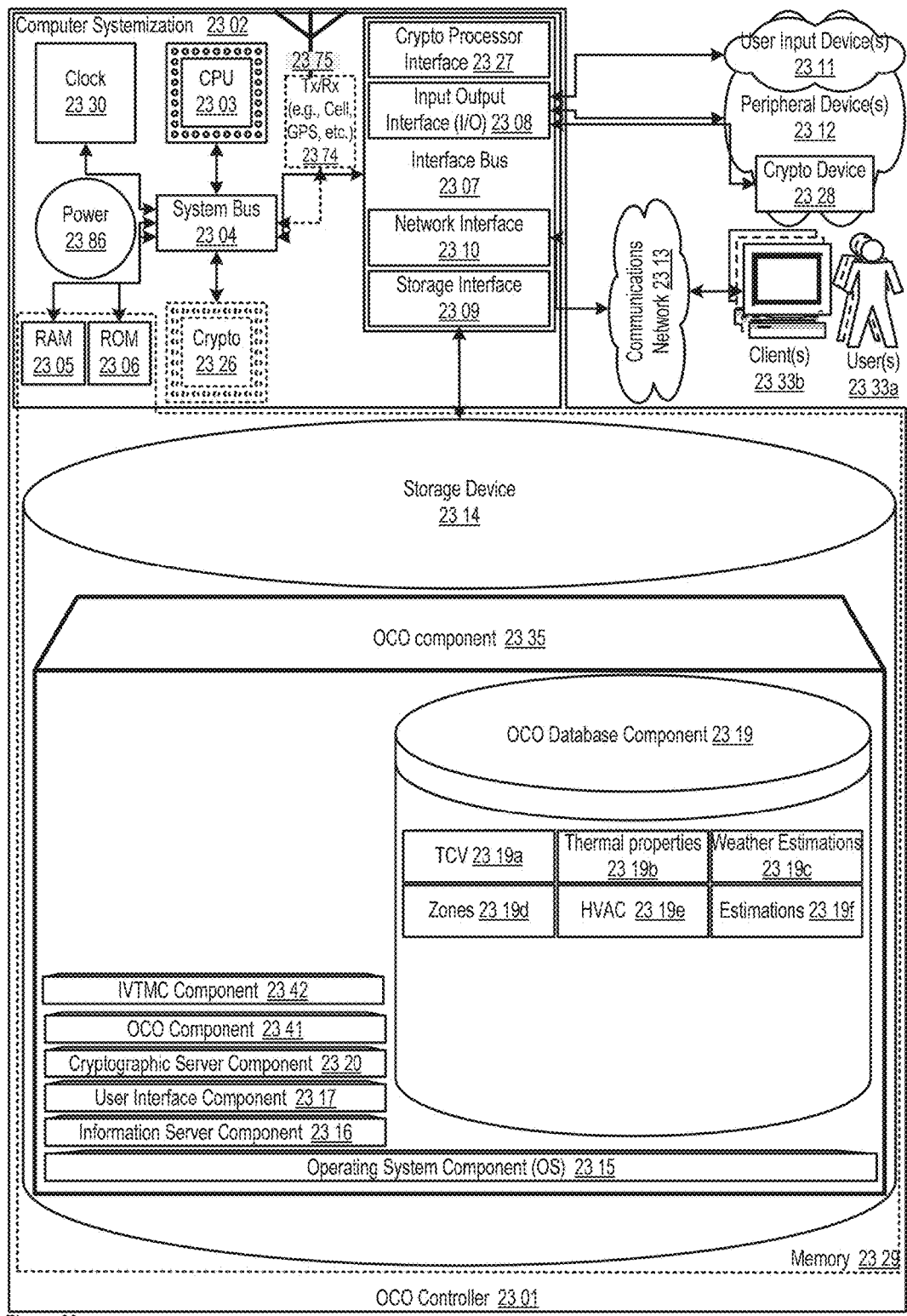
FIG. 23 shows a block diagram illustrating aspects of an exemplary embodiment of a OCO controller, in one embodiment.

FIG. 23 shows a block diagram illustrating embodiments of an OCO controller. In this embodiment, the OCO controller 2301 may serve to aggregate, process, store, search, serve, identify, instruct, generate, match, and/or facilitate interactions with a computer through various technologies, and/or other related data.

Typically, users, which may be people and/or other systems, may engage information technology systems (e.g., computers) to facilitate information processing. In turn, computers employ processors to process information; such processors 2303 may be referred to as central processing units (CPU). One form of processor is referred to as a microprocessor. CPUs use communicative circuits to pass binary encoded signals acting as instructions to enable various operations. These instructions may be operational and/or data instructions containing and/or referencing other instructions and data in various processor accessible and operable areas of memory 2329 (e.g., registers, cache memory, random access memory, etc.). Such communicative instructions may be stored and/or transmitted in batches (e.g., batches of instructions) as programs and/or data components to facilitate desired operations. These stored instruction codes, e.g., programs, may engage the CPU circuit components and other motherboard and/or system components to perform desired operations. One type of program is a computer operating system, which, may be executed by CPU on a computer; the operating system enables and facilitates users to access and operate computer information technology and resources. Some resources that may be employed in information technology systems include: input and output mechanisms through which data may pass into and out of a computer; memory storage into which data may be saved; and processors by which information may be processed. These information technology systems may be used to collect data for later retrieval, analysis, and manipulation, which may be facilitated through a database program. These information technology systems provide interfaces that allow users to access and operate various system components.

In one embodiment, the OCO controller 2301 may be connected to and/or communicate with entities such as, but not limited to: one or more users from user input devices 2311; peripheral devices 2312; an optional cryptographic processor device 2328; and/or a communications network 2313.

Networks are commonly thought to comprise the interconnection and interoperation of clients, servers, and intermediary nodes in a graph topology. It should be noted that the term "server" as used throughout this application refers generally to a computer, other device, program, or combination thereof that processes and responds to the requests of remote users across a communications network. Servers serve their information to requesting "clients." The term "client" as used herein refers generally to a computer, program, other device, user and/or combination thereof that is capable of processing and making requests and obtaining and processing any responses from servers across a communications network. A computer, other device, program, or combination thereof that facilitates, processes information and requests, and/or furthers the passage of information from a source user to a destination user is commonly referred to as a "node." Networks are generally thought to facilitate the transfer of information from source points to destinations. A node specifically tasked with furthering the passage of information from a source to a destination is commonly called a "router." There are many forms of networks such as Local Area Networks (LANs), Pico networks, Wide Area Networks (WANs), Wireless Networks (WLANs), etc. For example, the Internet is generally accepted as being an interconnection of a multitude of networks whereby remote clients and servers may access and interoperate with one another.

The OCO controller 2301 may be based on computer systems that may comprise, but are not limited to, components such as: a computer systemization 2302 connected to memory 2329.

Computer Systemization

A computer systemization 2302 may comprise a clock 2330, central processing unit ("CPU(s)") and/or "processor(s)" (these terms are used interchangeable throughout the disclosure unless noted to the contrary)) 2303, a memory 2329 (e.g., a read only memory (ROM) 2306, a random access memory (RAM) 2305, etc.), and/or an interface bus 2307, and most frequently, although not necessarily, are all interconnected and/or communicating through a system bus 2304 on one or more (mother)board(s) 2302 having conductive and/or otherwise transportive circuit pathways through which instructions (e.g., binary encoded signals) may travel to effectuate communications, operations, storage, etc. The computer systemization may be connected to a power source 2386; e.g., optionally the power source may be internal. Optionally, a cryptographic processor 2326 and/or transceivers (e.g., ICs) 2374 may be connected to the system bus. In another embodiment, the cryptographic processor and/or transceivers may be connected as either internal and/or external peripheral devices 2312 via the interface bus I/O. In turn, the transceivers may be connected to antenna(s) 2375, thereby effectuating wireless transmission and reception of various communication and/or sensor protocols; for example the antenna(s) may connect to: a Texas Instruments WILINK WL1283 transceiver chip (e.g., providing 802.11n, BLUETOOTH protocol 3.0, FM, global positioning system (GPS) (thereby allowing OCO controller to determine its location)); Broadcom BCM4329FKUBG transceiver chip (e.g., providing 802.11n, BLUETOOTH protocol 2.1+EDR, FM, etc.); a Broadcom BCM4750IUB8 receiver chip (e.g., GPS); an Infineon Technologies X-GOLD chip 618-PMB9800 (e.g., providing 2G/3G HSDPA/HSUPA communications); and/or the like. The system clock typically has a crystal oscillator and generates a base signal through the computer systemization's circuit pathways. The clock is typically coupled to the system bus and various clock multipliers that will increase or decrease the base operating frequency for other components interconnected in the computer systemization. The clock and various components in a computer systemization drive signals embodying information throughout the system. Such transmission and reception of instructions embodying information throughout a computer systemization may be commonly referred to as communications. These communicative instructions may further be transmitted, received, and the cause of return and/or reply communications beyond the instant computer systemization to: communications networks, input devices, other computer systemizations, peripheral devices, and/or the like. It should be understood that in alternative embodiments, any of the above components may be connected directly to one another, connected to the CPU, and/or organized in numerous variations employed as exemplified by various computer systems.

The CPU comprises at least one high-speed data processor adequate to execute program components for executing user and/or system-generated requests. Often, the processors themselves will incorporate various specialized processing units, such as, but not limited to: integrated system (bus) controllers, memory management control units, floating point units, and even specialized processing sub-units like graphics processing units, digital signal processing units, and/or the like. Additionally, processors may include internal fast access addressable memory, and be capable of mapping and addressing memory 2329 beyond the processor itself; internal memory may include, but is not limited to: fast registers, various levels of cache memory (e.g., level 1, 2, 3, etc.), RAM, etc. The processor may access this memory through the use of a memory address space that is accessible via instruction address, which the processor can construct and decode allowing it to access a circuit path to a specific memory address space having a memory state. The CPU may be a microprocessor such as: AMD's ATHLON microprocessor, DURON microprocessor and/or Opteron OPTERON microprocessor; ARM's application, embedded and secure processors; IBM and/or Motorola's DRAGONBALL microprocessor and POWERPC microprocessor; IBM's and Sony's Cell processor; Intel's CELERON microprocessor, Core (2) Duo CORE (2) DUO microprocessor, ITANIUM microprocessor, PENTIUM microprocessor, XEON microprocessor, and/or XSCALE microprocessor; and/or the like processor(s). The CPU interacts with memory through instruction passing through conductive and/or transportive conduits (e.g., (printed) electronic and/or optic circuits) to execute stored instructions (i.e., program code) according to conventional data processing techniques. Such instruction passing facilitates communication within the OCO controller and beyond through various interfaces. Should processing requirements dictate a greater amount speed and/or capacity, distributed processors (e.g., Distributed OCO), mainframe, multi-core, parallel, and/or supercomputer architectures may similarly be employed. Alternatively, should deployment requirements dictate greater portability, smaller Personal Digital Assistants (PDAs) may be employed.

Depending on the particular implementation, features of the OCO may be achieved by implementing a microcontroller such as CAST's R8051XC2 microcontroller; Intel's MCS 51 (i.e., 8051 microcontroller); and/or the like. Also, to implement certain features of the OCO, some feature implementations may rely on embedded components, such as: Application-Specific Integrated Circuit ("ASIC"), Digital Signal Processing ("DSP"), Field Programmable Gate Array ("FPGA"), and/or the like embedded technology. For example, any of the OCO component collection (distributed or otherwise) and/or features may be implemented via the microprocessor and/or via embedded components; e.g., via ASIC, coprocessor, DSP, FPGA, and/or the like. Alternately, some implementations of the OCO may be implemented with embedded components that are configured and used to achieve a variety of features or signal processing.

Depending on the particular implementation, the embedded components may include software solutions, hardware solutions, and/or some combination of both hardware/software solutions. For example, OCO features discussed herein may be achieved through implementing FPGAs, which are a semiconductor devices containing programmable logic components called "logic blocks", and programmable interconnects, such as the high performance FPGA Virtex series and/or the low cost Spartan series manufactured by Xilinx. Logic blocks and interconnects can be programmed by the customer or designer, after the FPGA is manufactured, to implement any of the OCO features. A hierarchy of programmable interconnects allow logic blocks to be interconnected as needed by the OCO system designer/administrator, somewhat like a one-chip programmable breadboard. An FPGA's logic blocks can be programmed to perform the operation of basic logic gates such as AND, and XOR, or more complex combinational operators such as decoders or mathematical operations. In most FPGAs, the logic blocks also include memory elements, which may be circuit flip-flops or more complete blocks of memory. In some circumstances, the OCO may be developed on regular FPGAs and then migrated into a fixed version that more resembles ASIC implementations. Alternate or coordinating implementations may migrate OCO controller features to a final ASIC instead of or in addition to FPGAs. Depending on the implementation all of the aforementioned embedded components and microprocessors may be considered the "CPU" and/or "processor" for the OCO.

Power Source

The power source 2386 may be of any standard form for powering small electronic circuit board devices such as the following power cells: alkaline, lithium hydride, lithium ion, lithium polymer, nickel cadmium, solar cells, and/or the like. Other types of AC or DC power sources may be used as well. In the case of solar cells, in one embodiment, the case provides an aperture through which the solar cell may capture photonic energy. The power cell 2386 is connected to at least one of the interconnected subsequent components of the OCO thereby providing an electric current to all subsequent components. In one example, the power source 2386 is connected to the system bus component 2304. In an alternative embodiment, an outside power source 2386 is provided through a connection across the I/O 2308 interface. For example, a USB and/or IEEE 1394 connection carries both data and power across the connection and is therefore a suitable source of power.

Interface Adapters

Interface bus(es) 2307 may accept, connect, and/or communicate to a number of interface adapters, conventionally although not necessarily in the form of adapter cards, such as but not limited to: input output interfaces (I/O) 2308, storage interfaces 2309, network interfaces 2310, and/or the like. Optionally, cryptographic processor interfaces 2327 similarly may be connected to the interface bus. The interface bus provides for the communications of interface adapters with one another as well as with other components of the computer systemization. Interface adapters are adapted for a compatible interface bus. Interface adapters conventionally connect to the interface bus via a slot architecture. Conventional slot architectures may be employed, such as, but not limited to: Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and/or the like.

Storage interfaces 2309 may accept, communicate, and/or connect to a number of storage devices such as, but not limited to: storage devices 2314, removable disc devices, and/or the like. Storage interfaces may employ connection protocols such as, but not limited to: (Ultra) (Serial) Advanced Technology Attachment (Packet Interface) ((Ultra) (Serial) ATA(PI)), (Enhanced) Integrated Drive Electronics ((E)IDE), Institute of Electrical and Electronics Engineers (IEEE) 1394, fiber channel, Small Computer Systems Interface (SCSI), Universal Serial Bus (USB), and/or the like.

Network interfaces 2310 may accept, communicate, and/or connect to a communications network 2313. Through a communications network 2313, the OCO controller is accessible through remote clients 2333b (e.g., computers with web browsers) by users 2333a. Network interfaces may employ connection protocols such as, but not limited to: direct connect, Ethernet (thick, thin, twisted pair 10/100/1000 Base T, and/or the like), Token Ring, wireless connection such as IEEE 802.11a-x, and/or the like. Should processing requirements dictate a greater amount speed and/or capacity, distributed network controllers (e.g., Distributed OCO), architectures may similarly be employed to pool, load balance, and/or otherwise increase the communicative bandwidth required by the OCO controller. A communications network may be any one and/or the combination of the following: a direct interconnection; the Internet; a Local Area Network (LAN); a Metropolitan Area Network (MAN); an Operating Missions as Nodes on the Internet (OMNI); a secured custom connection; a Wide Area Network (WAN); a wireless network (e.g., employing protocols such as, but not limited to a Wireless Application Protocol (WAP), I-mode, and/or the like); and/or the like. A network interface may be regarded as a specialized form of an input output interface. Further, multiple network interfaces 2310 may be used to engage with various communications network types 2313. For example, multiple network interfaces may be employed to allow for the communication over broadcast, multicast, and/or unicast networks.

Input Output interfaces (I/O) 2308 may accept, communicate, and/or connect to user input devices 2311, peripheral devices 2312, cryptographic processor devices 2328, and/or the like. I/O may employ connection protocols such as, but not limited to: audio: analog, digital, monaural, RCA, stereo, and/or the like; data: Apple Desktop Bus (ADB) protocol, IEEE 1394a-b, serial, universal serial bus (USB); infrared; joystick; keyboard; midi; optical; PC AT; PS/2; parallel; radio; video interface: Apple Desktop Connector (ADC) protocol, BNC protocol, coaxial, component, composite, digital, Digital Visual Interface (DVI), high-definition multimedia interface (HDMI), RCA, RF antennae, S-Video, VGA, and/or the like; wireless transceivers: 802.11a/b/g/n/x; BLUETOOTH protocol; cellular (e.g., code division multiple access (CDMA), high speed packet access (HSPA (+)), highspeed downlink packet access (HSDPA), global system for mobile communications (GSM), long term evolution (LTE), WIMAX protocol, etc.); and/or the like. One typical output device may include a video display, which typically comprises a Cathode Ray Tube (CRT) or Liquid Crystal Display (LCD) based monitor with an interface (e.g., DVI circuitry and cable) that accepts signals from a video interface, may be used. The video interface composites information generated by a computer systemization and generates video signals based on the composited information in a video memory frame. Another output device is a television set, which accepts signals from a video interface. Typically, the video interface provides the composited video information through a video connection interface that accepts a video display interface (e.g., an RCA composite video connector accepting an RCA composite video cable; a DVI connector accepting a DVI display cable, etc.).

User input devices 2311 often are a type of peripheral device 512 (see below) and may include: card readers, dongles, finger print readers, gloves, graphics tablets, joysticks, keyboards, microphones, mouse (mice), remote controls, retina readers, touch screens (e.g., capacitive, resistive, etc.), trackballs, trackpads, sensors (e.g., accelerometers, ambient light, GPS, gyroscopes, proximity, etc.), styluses, and/or the like.

Peripheral devices 2312 may be connected and/or communicate to I/O and/or other facilities of the like such as network interfaces, storage interfaces, directly to the interface bus, system bus, the CPU, and/or the like. Peripheral devices may be external, internal and/or part of the OCO controller. Peripheral devices may include: antenna, audio devices (e.g., line-in, line-out, microphone input, speakers, etc.), cameras (e.g., still, video, webcam, etc.), dongles (e.g., for copy protection, ensuring secure transactions with a digital signature, and/or the like), external processors (for added capabilities; e.g., crypto devices 528), force-feedback devices (e.g., vibrating motors), network interfaces, printers, scanners, storage devices, transceivers (e.g., cellular, GPS, etc.), video devices (e.g., goggles, monitors, etc.), video sources, visors, and/or the like. Peripheral devices often include types of input devices (e.g., cameras).

It should be noted that although user input devices and peripheral devices may be employed, the OCO controller may be embodied as an embedded, dedicated, and/or monitor-less (i.e., headless) device, wherein access would be provided over a network interface connection.

Cryptographic units such as, but not limited to, microcontrollers, processors 2326, interfaces 2327, and/or devices 2328 may be attached, and/or communicate with the OCO controller. A MC68HC16 microcontroller, manufactured by Motorola Inc., may be used for and/or within cryptographic units. The MC68HC16 microcontroller utilizes a 16-bit multiply-and-accumulate instruction in the 16 MHz configuration and requires less than one second to perform a 512-bit RSA private key operation. Cryptographic units support the authentication of communications from interacting agents, as well as allowing for anonymous transactions. Cryptographic units may also be configured as part of the CPU. Equivalent microcontrollers and/or processors may also be used. Other commercially available specialized cryptographic processors include: Broadcom's CRYPTONETX processor and other Security Processors; nCipher's NSHIELD processor; SafeNet's LUNA PCI processor (e.g., 7100) series; Semaphore Communications' 40 MHz ROADRUNNER processor 184; Sun's Cryptographic Accelerators (e.g., Accelerator 6000 PCIe Board, Accelerator 500 Daughtercard); VIA NANO Processor (e.g., L2100, L2200, U2400) line, which is capable of performing 500+ MB/s of cryptographic instructions; VLSI Technology's 33 MHz 6868; and/or the like.

Memory

Generally, any mechanization and/or embodiment allowing a processor to affect the storage and/or retrieval of information is regarded as memory 2329. However, memory is a fungible technology and resource, thus, any number of memory embodiments may be employed in lieu of or in concert with one another. It is to be understood that the OCO controller and/or a computer systemization may employ various forms of memory 2329. For example, a computer systemization may be configured wherein the operation of on-chip CPU memory (e.g., registers), RAM, ROM, and any other storage devices are provided by a paper punch tape or paper punch card mechanism; however, such an embodiment would result in an extremely slow rate of operation. In a typical configuration, memory 2329 will include ROM 2306, RAM 2305, and a storage device 2314. A storage device 2314 may be any conventional computer system storage. Storage devices may include a drum; a (fixed and/or removable) magnetic disk drive; a magneto-optical drive; an optical drive (i.e., Blueray, CD ROM/RAM/Recordable (R)/ ReWritable (RW), DVD R/RW, HD DVD R/RW etc.); an array of devices (e.g., Redundant Array of Independent Disks (RAID)); solid state memory devices (USB memory, solid state drives (SSD), etc.); other processor-readable storage mediums; and/or other devices of the like. Thus, a computer systemization generally requires and makes use of memory.

Component Collection

The memory 2329 may contain a collection of program and/or database components and/or data such as, but not limited to: operating system component 2315; information server component 2316; user interface component 2317; OCO database component 2319; cryptographic server component 2327; OCO Component 2341; and/or the like (i.e., collectively a component collection). The aforementioned components may be incorporated into (e.g., be sub-components of), loaded from, loaded by, or otherwise operatively available to and from the OCO component(s) 2335.

Any component may be stored and accessed from the storage devices and/or from storage devices accessible through an interface bus. Although program components such as those in the component collection, typically, are stored in a local storage device 2314, they may also be loaded and/or stored in other memory such as: remote "cloud" storage facilities accessible through a communications network; integrated ROM memory; via an FPGA or ASIC implementing component logic; and/or the like.

Operating System Component

The operating system component 2315 is an executable program component facilitating the operation of the OCO controller. Typically, the operating system facilitates access of I/O, network interfaces, peripheral devices, storage devices, and/or the like. The operating system may be a highly fault tolerant, scalable, and secure system such as: Unix and Unix-like system distributions (such as AT&T's UNIX operating system; Berkley Software Distribution (BSD) variations such as FREEBSD operating system, NETBSD operating system, OPENBSD operating system, and/or the like; Linux distributions such as RED HAT operating system, DEBIAN operating system, UBUNTU operating system, and/or the like); and/or the like operating systems. However, more limited and/or less secure operating systems also may be employed such as Apple OS-X, Microsoft Windows 2000/2003/3.1/95/98/CE/MILLENIUM/NT/ VISTA/XP/WIN7 (Server) operating systems, and/or the like. An operating system may communicate to and/or with other components in a component collection, including itself, and/or the like. Most frequently, the operating system communicates with other program components, user interfaces, and/or the like. The operating system, once executed by the CPU, may enable the interaction with communications networks, data, I/O, peripheral devices, program components, memory, user input devices, and/or the like. The operating system may provide communications protocols that allow the OCO controller to communicate with other entities through a communications network 2313. Various communication protocols may be used by the OCO controller as a subcarrier transport mechanism for interaction, such as, but not limited to: multicast, TCP/IP, UDP, unicast, and/or the like.

Information Server Component

An information server component 2316 is a stored program component that is executed by a CPU. The information server may be a conventional Internet information server such as, but not limited to Apache Software Foundation's Apache, Microsoft's Internet Information Server, and/or the like. The information server may allow for the execution of program components through facilities such as Active Server Page (ASP), ActiveX, (ANSI) (Objective-) C (++), C# and/or .NET, Common Gateway Interface (CGI) scripts, dynamic (D) hypertext markup language (HTML), FLASH, JAVA, JAVASCRIPT, Practical Extraction Report Language (PERL), Hypertext Pre-Processor (PHP), pipes, PYTHON, wireless application protocol (WAP), WebObjects, and/or the like. The information server may support secure communications protocols such as, but not limited to, File Transfer Protocol (FTP); HyperText Transfer Protocol (HTTP); Secure Hypertext Transfer Protocol (HTTPS), Secure Socket Layer (SSL), messaging protocols (e.g., ICQ, Internet Relay Chat (IRC), Presence and Instant Messaging Protocol (PRIM), Internet Engineering Task Force's (IETF's) Session Initiation Protocol (SIP), SIP for Instant Messaging and Presence Leveraging Extensions (SIMPLE), open XML-based Extensible Messaging and Presence Protocol (XMPP) (i.e., JABBER or Open Mobile Alliance's (OMA's) Instant Messaging and Presence Service (IMPS)), Representational State Transfer (REST) and/or the like. The information server provides results in the form of Web pages to Web browsers, and allows for the manipulated generation of the Web pages through interaction with other program components. After a Domain Name System (DNS) resolution portion of an HTTP request is resolved to a particular information server, the information server resolves requests for information at specified locations on the OCO controller based on the remainder of the HTTP request. For example, a request such as http://123.124.125.126/myInformation.html might have the IP portion of the request "123.124.125.126" resolved by a DNS server to an information server at that IP address; that information server might in turn further parse the http request for the "/myInformation.html" portion of the request and resolve it to a location in memory containing the information "myInformation.html." Additionally, other information serving protocols may be employed across various ports, e.g., FTP communications across port 21, and/or the like. An information server may communicate to and/or with other components in a component collection, including itself, and/or facilities of the like. Most frequently, the information server communicates with the OCO database component 2319, operating system component 2315, other program components, user interfaces, and/or the like.

Access from the Information Server Component 2316 to the OCO database component 2319 may be achieved through a number of database bridge mechanisms such as through scripting languages as enumerated below (e.g., CGI) and through inter-application communication channels as enumerated below (e.g., CORBA, WEBOBJECTS, etc.). Any data requests through a Web browser are parsed through the bridge mechanism into appropriate grammars as required by the OCO. In one embodiment, the information server would provide a Web form accessible by a Web browser. Entries made into supplied fields in the Web form are tagged as having been entered into the particular fields, and parsed as such. The entered terms are then passed along with the field tags, which act to instruct the parser to generate queries directed to appropriate tables and/or fields. In one embodiment, the parser may generate queries in standard SQL by instantiating a search string with the proper join/select commands based on the tagged text entries, wherein the resulting command is provided over the bridge mechanism to the OCO as a query. Upon generating query results from the query, the results are passed over the bridge mechanism, and may be parsed for formatting and generation of a new results Web page by the bridge mechanism. Such a new results Web page is then provided to the information server, which may supply it to the requesting Web browser. Also, an information server may contain, communicate, generate, obtain, and/or provide program component, system, user, and/or data communications, requests, and/or responses.

User Interface Component

Computer interfaces in some respects are similar to automobile operation interfaces. Automobile operation interface elements such as steering wheels, gearshifts, and speedometers facilitate the access, operation, and display of automobile resources, and status. Computer interaction interface elements such as check boxes, cursors, menus, scrollers, and windows (collectively and commonly referred to as widgets) similarly facilitate the access, capabilities, operation, and display of data and computer hardware and operating system resources, and status. Operation interfaces are commonly called user interfaces. Graphical user interfaces (GUIs) such as the Apple Macintosh Operating System's Aqua AQUA, IBM's OS/2, Microsoft's Windows 2000/2003/3.1/95/98/CE//MILLENIUM/NT/XP/VISTA/7 (i.e., AERO), Unix's X-Windows, web interface libraries such as, but not limited to, DOJO, JQUERY UI, MOOTOOLS, PROTOTYPE; SCRIPT.ACULO.US SWFOBJECT, YAHOO! User Interface, any of which may be used and provide a baseline and means of accessing and displaying information graphically to users.

A user interface component 2317 is a stored program component that is executed by a CPU. The user interface may be a conventional graphic user interface as provided by, with, and/or atop operating systems and/or operating environments such as already discussed. The user interface may allow for the display, execution, interaction, manipulation, and/or operation of program components and/or system facilities through textual and/or graphical facilities. The user interface provides a facility through which users may affect, interact, and/or operate a computer system. A user interface may communicate to and/or with other components in a component collection, including itself, and/or facilities of the like. Most frequently, the user interface communicates with operating system component 2315, other program components, and/or the like. The user interface may contain, communicate, generate, obtain, and/or provide program component, system, user, and/or data communications, requests, and/or responses.

Cryptographic Server Component

A cryptographic server component 2320 is a stored program component that is executed by a CPU 2303, cryptographic processor 2326, cryptographic processor interface 2327, cryptographic processor device 2328, and/or the like. Cryptographic processor interfaces will allow for expedition of encryption and/or decryption requests by the cryptographic component; however, the cryptographic component, alternatively, may run on a conventional CPU. The cryptographic component allows for the encryption and/or decryption of provided data. The cryptographic component allows for both symmetric and asymmetric (e.g., Pretty Good Protection (PGP)) encryption and/or decryption. The cryptographic component may employ cryptographic techniques such as, but not limited to: digital certificates (e.g., X.509 authentication framework), digital signatures, dual signatures, enveloping, password access protection, public key management, and/or the like. The cryptographic component will facilitate numerous (encryption and/or decryption) security protocols such as, but not limited to: checksum, Data Encryption Standard (DES), Elliptical Curve Encryption (ECC), International Data Encryption Algorithm (IDEA), Message Digest 5 (MD5, which is a one way hash operation), passwords, Rivest Cipher (RC5), Rijndael (AES), RSA, Secure Hash Algorithm (SHA), Secure Socket Layer (SSL), Secure Hypertext Transfer Protocol (HTTPS), and/or the like. Employing such encryption security protocols, the OCO may encrypt all incoming and/or outgoing communications and may serve as node within a virtual private network (VPN) with a wider communications network. The cryptographic component facilitates the process of "security authorization" whereby access to a resource is inhibited by a security protocol wherein the cryptographic component effects authorized access to the secured resource. In addition, the cryptographic component may provide unique identifiers of content, e.g., employing and MD5 hash to obtain a unique signature for an digital audio file. A cryptographic component may communicate to and/or with other components in a component collection, including itself, and/or facilities of the like. The cryptographic component supports encryption schemes allowing for the secure transmission of information across a communications network to enable the OCO component to engage in secure transactions if so desired. The cryptographic component facilitates the secure accessing of resources on the OCO and facilitates the access of secured resources on remote systems; i.e., it may act as a client and/or server of secured resources. Most frequently, the cryptographic component communicates with information server component 2316, operating system component 2315, other program components, and/or the like. The cryptographic component may contain, communicate, generate, obtain, and/or provide program component, system, user, and/or data communications, requests, and/or responses.

OCO Database Component

The OCO database component 2319 may be embodied in a database and its stored data. The database is a stored program component, which is executed by the CPU; the stored program component portion configuring the CPU to process the stored data. The database may be a conventional, fault tolerant, relational, scalable, secure database such as Oracle or Sybase. Relational databases are an extension of a flat file. Relational databases consist of a series of related tables. The tables are interconnected via a key field. Use of the key field allows the combination of the tables by indexing against the key field; i.e., the key fields act as dimensional pivot points for combining information from various tables. Relationships generally identify links maintained between tables by matching primary keys. Primary keys represent fields that uniquely identify the rows of a table in a relational database. More precisely, they uniquely identify rows of a table on the "one" side of a one-to-many relationship.

Alternatively, the OCO database may be implemented using various standard data-structures, such as an array, hash, (linked) list, struct, structured text file (e.g., XML), table, and/or the like. Such data-structures may be stored in memory and/or in (structured) files. In another alternative, an object-oriented database may be used, such as FRONTIER; OBJECTSTORE, POET, ZOPE, and/or the like. Object databases can include a number of object collections that are grouped and/or linked together by common attributes; they may be related to other object collections by some common attributes. Object-oriented databases perform similarly to relational databases with the exception that objects are not just pieces of data but may have other types of capabilities encapsulated within a given object. Also, the database may be implemented as a mix of data structures, objects, and relational structures. Databases may be consolidated and/or distributed in countless variations through standard data processing techniques. Portions of databases, e.g., tables, may be exported and/or imported and thus decentralized and/or integrated.

In one embodiment, the database component 2319 includes several tables 2319*a-f*. A thermal coefficient vector table (TCV) 2319*a* may include fields such as, but not limited to: tcv_id, tcv_type, tcv_value, tcv_date, and/or the like. A thermal properties (TP) table 2319*b* may include fields such as, but not limited to: tp_id, tp_value, hvac_id, zone_id, and/or the like. A weather estimations (WE) table 2319*c* may include fields such as, but not limited to: we_id, we_time, we_value, we_serviceProvider, and/or the like. A zone table 2319*d* may include fields such as, but not limited to: zone_id, thermalDevice_id, hvac_id, tvc_id, and/or the like. A HVAC table 2319*e* may include fields such as, but not limited to: hvac_id, hvac_model, hvac_zoneID, hvac_avgPowerConsumption, hvac_avgEnergyEfficiency, and/or the like. An estimations (EST) table 2319*f* may include fields such as, but not limited to: est_id, est_time, est_type, est_value, est_zondeID and/or the like. Any of the aforementioned tables may support and/or track multiple entities, accounts, users and/or the like.

In one embodiment, the OCO database component may interact with other database systems. For example, when employing a distributed database system. In such an embodiment, queries and data access by any OCO component may treat the combination of the OCO database component results and results from a second segment in a distributed database system as an integrated database layer. Such a database layer may be accessed as a single database entity, for example through OCO database component 2319, by any OCO component.

In one embodiment, user programs may contain various user interface primitives, which may serve to update the OCO. Also, various accounts may require custom database tables depending upon the environments and the types of clients the OCO may need to serve. It should be noted that any unique fields may be designated as a key field throughout. In an alternative embodiment, these tables have been decentralized into their own databases and their respective database controllers (i.e., individual database controllers for each of the above tables). Employing standard data processing techniques, one may further distribute the databases over several computer systemizations and/or storage devices. Similarly, configurations of the decentralized database controllers may be varied by consolidating and/or distributing the various database components 2319a-f. The OCO may be configured to keep track of various settings, inputs, and parameters via database controllers.

The OCO database may communicate to and/or with other components in a component collection, including itself, and/or facilities of the like. Most frequently, the OCO database communicates with the OCO component, other program components, and/or the like. The database may contain, retain, and provide information regarding other nodes and data.

OCO Component

The OCO component 2335 is a stored program component that is executed by a CPU. In one embodiment, the OCO component incorporates any and/or all combinations of the aspects of the OCO that was discussed in the previous figures. As such, the OCO affects accessing, obtaining and the provision of information, services, transactions, and/or the like across various communications networks. The features and embodiments of the OCO discussed herein increase network efficiency by reducing data transfer requirements the use of more efficient data structures and mechanisms for their transfer and storage. As a consequence, more data may be transferred in less time, and latencies with regard to data processing operations and transactions, are also reduced. In many cases, such reduction in storage, transfer time, bandwidth requirements, latencies, etc., will reduce the capacity and structural infrastructure requirements to support the OCO's features and facilities, and in many cases reduce the costs, energy consumption/requirements, and extend the life of OCO's underlying infrastructure; this has the added benefit of making the OCO more reliable. Similarly, many of the features and mechanisms are designed to be easier for users to use and access, thereby broadening the audience that may enjoy/employ and exploit the feature sets of the OCO; such ease of use also helps to increase the reliability of the OCO. In addition, the feature sets include heightened security as noted via the Cryptographic components 2320, 2326, 2328 and throughout, making access to the features and data more reliable and secure.

The OCO component may transform user weather estimations and thermal properties and/or the like, via various components described herein, into estimated temperature, estimated energy consumption, estimated power consumption and the like metrics. In one embodiment, the OCO takes inputs (e.g., weather estimations 109, thermal properties 111, and/or the like) etc., and transforms the inputs via various components (e.g., OCO component 2341, IVTMC component 2342 (e.g., as detailed in copending U.S. patent application Ser. No. 14/955,971, expressly incorporated herein by reference) and/or the like), into outputs (e.g., estimated temperature, estimated energy consumption, estimated power consumption 1 and/or the like).

The OCO component enabling access of information between nodes may be developed by employing standard development tools and languages such as, but not limited to: Apache components, Assembly, ActiveX, binary executables, (ANSI) (Objective-) C (++), C# and/or .NET, database adapters, CGI scripts, JAVA, JAVASCRIPT, mapping tools, procedural and object oriented development tools, PERL, PHP, PYTHON, shell scripts, SQL commands, web application server extensions, web development environments and libraries (e.g., Microsoft's ActiveX; Adobe AIR, FLEX & FLASH; AJAX; (D)HTML; DOJO, JAVA, JAVASCRIPT; JQUERY UI, MOOTOOLS, PROTOTYPE SCRIPT.ACULO.US; Simple Object Access Protocol (SOAP); SWFOBJECT, YAHOO! User Interface; and/or the like), WEBOBJECTS, and/or the like. In one embodiment, the OCO server employs a cryptographic server to encrypt and decrypt communications. The OCO component may communicate to and/or with other components in a component collection, including itself, and/or facilities of the like. Most frequently, the OCO component communicates with the OCO database component 2319, operating system component 2315, other program components, and/or the like. The OCO may contain, communicate, generate, obtain, and/or provide program component, system, user, and/or data communications, requests, and/or responses.

Distributed OCO Components

The structure and/or operation of any of the OCO node controller components may be combined, consolidated, and/or distributed in any number of ways to facilitate development and/or deployment. Similarly, the component collection may be combined in any number of ways to facilitate deployment and/or development. To accomplish this, one may integrate the components into a common code base or in a facility that can dynamically load the components on demand in an integrated fashion.

The component collection may be consolidated and/or distributed in countless variations through standard data processing and/or development techniques. Multiple instances of any one of the program components in the program component collection may be instantiated on a single node, and/or across numerous nodes to improve performance through load-balancing and/or data-processing techniques. Furthermore, single instances may also be distributed across multiple controllers and/or storage devices; e.g., databases. All program component instances and controllers working in concert may do so through standard data processing communication techniques.

The configuration of the OCO controller will depend on the context of system deployment. Factors such as, but not limited to, the budget, capacity, location, and/or use of the underlying hardware resources may affect deployment requirements and configuration. Regardless of if the configuration results in more consolidated and/or integrated program components, results in a more distributed series of program components, and/or results in some combination between a consolidated and distributed configuration, data may be communicated, obtained, and/or provided. Instances of components consolidated into a common code base from the program component collection may communicate, obtain, and/or provide data. This may be accomplished through intra-application data processing communication techniques such as, but not limited to: data referencing (e.g., pointers), internal messaging, object instance variable communication, shared memory space, variable passing, and/or the like.

If component collection components are discrete, separate, and/or external to one another, then communicating, obtaining, and/or providing data with and/or to other component components may be accomplished through inter-application data processing communication techniques such as, but not limited to: Application Program Interfaces (API) information passage; (distributed) Component Object Model ((D)COM), (Distributed) Object Linking and Embedding ((D)OLE), and/or the like), Common Object Request Broker Architecture (CORBA), Jini local and remote application program interfaces, JavaScript Object Notation (JSON), Remote Method Invocation (RMI), SOAP, Representational State Transfer (REST), process pipes, shared files, and/or the like. Messages sent between discrete component components for inter-application communication or within memory spaces of a singular component for intra-application communication may be facilitated through the creation and parsing of a grammar. A grammar may be developed by using development tools such as lex, yacc, XML, and/or the like, which allow for grammar generation and parsing capabilities, which in turn may form the basis of communication messages within and between components.

For example, a grammar may be arranged to recognize the tokens of an HTTP post command, e.g.:

w3c-post http:// . . . Value1 where Value1 is discerned as being a parameter because "http://" is part of the grammar syntax, and what follows is considered part of the post value. Similarly, with such a grammar, a variable "Value1" may be inserted into an "http://" post command and then sent. The grammar syntax itself may be presented as structured data that is interpreted and/or otherwise used to generate the parsing mechanism (e.g., a syntax description text file as processed by lex, yacc, etc.). Also, once the parsing mechanism is generated and/or instantiated, it itself may process and/or parse structured data such as, but not limited to: character (e.g., tab) delineated text, HTML, structured text streams, XML, and/or the like structured data. Further, the parsing grammar may be used beyond message parsing, but may also be used to parse: databases, data collections, data stores, structured data, and/or the like. Again, the desired configuration will depend upon the context, environment, and requirements of system deployment.

Additional OCO Configurations

In order to address various issues and advance the art, the entirety of this application for OCO (including the Cover Page, Title, Headings, Field, Background, Summary, Brief Description of the Drawings, Detailed Description, Claims, Abstract, Figures, Appendices, and otherwise) shows, by way of illustration, various embodiments in which the claimed innovations may be practiced. The advantages and features of the application are of a representative sample of embodiments only, and are not exhaustive and/or exclusive. They are presented only to assist in understanding and teach the claimed principles. It should be understood that they are not representative of all claimed innovations. As such, certain aspects of the disclosure have not been discussed herein. That alternate embodiments may not have been presented for a specific portion of the innovations or that further undescribed alternate embodiments may be available for a portion is not to be considered a disclaimer of those alternate embodiments. It will be appreciated that many of those undescribed embodiments incorporate the same principles of the innovations and others are equivalent. Thus, it is to be understood that other embodiments may be utilized and functional, logical, operational, organizational, structural and/or topological modifications may be made without departing from the scope and/or spirit of the disclosure. As such, all examples and/or embodiments are deemed to be non-limiting throughout this disclosure. Also, no inference should be drawn regarding those embodiments discussed herein relative to those not discussed herein other than it is as such for purposes of reducing space and repetition. For instance, it is to be understood that the logical and/or topological structure of any combination of any program components (a component collection), other components and/or any present feature sets as described in the figures and/or throughout are not limited to a fixed operating order and/or arrangement, but rather, any disclosed order is exemplary and all equivalents, regardless of order, are contemplated by the disclosure. Furthermore, it is to be understood that such features are not limited to serial execution, but rather, any number of threads, processes, services, servers, and/or the like that may execute asynchronously, concurrently, in parallel, simultaneously, synchronously, and/or the like are contemplated by the disclosure. As such, some of these features may be mutually contradictory, in that they cannot be simultaneously present in a single embodiment. Similarly, some features are applicable to one aspect of the innovations, and inapplicable to others. In addition, the disclosure includes other innovations not presently claimed. Applicant reserves all rights in those presently unclaimed innovations including the right to claim such innovations, file additional applications, continuations, continuations-in-part, divisionals, and/or the like thereof. As such, it should be understood that advantages, embodiments, examples, functional, features, logical, operational, organizational, structural, topological, and/or other aspects of the disclosure are not to be considered limitations on the disclosure as defined by the claims or limitations on equivalents to the claims. It is to be understood that, depending on the particular needs and/or characteristics of a OCO individual and/or enterprise user, database configuration and/or relational model, data type, data transmission and/or network framework, syntax structure, and/or the like, various embodiments of the OCO, may be implemented that enable a great deal of flexibility and customization as described herein.

The invention claimed is:

1. A processor-implemented method for adaptive temperature control of Heating, Ventilation, and Air Conditioning (HVAC) unit of a thermal system, the method comprising:
  receiving, at a comfort agent system, one or more thermal device properties associated with one or more volumes of the thermal system;
  receiving, at the comfort agent system, one or more weather estimates associated with a surrounding environment of the thermal system;
  determining a root state associated with a temperature vector comprising a plurality of temperatures associated with the one or more volumes of the thermal system, and the root state being associated with a first time, and a plurality of transitions;
  calculating a plurality of states including the root state, originating at the first time and extending over a duration of time, each state of the plurality of states being associated with a respective temperature vector, a respective time, and a respective plurality of transitions;
  determining one or more constraint properties, the one or more constraint properties being associated with a time originating at the first time and extending over the duration of time;
  selecting an optimal path comprising one or more of the plurality of states, the optimal path: (1) originating with the root state; (2) including transitions of the respective plurality of transitions, (3) defining a contiguous sequence of one or more of the plurality of states extending over the duration of time, each state in the sequence of one or more of the plurality of states being associated with a unique respective time; and (4) minimizing a cost associated with the optimal path determined by a cost function;

calculating one or more control temperature vectors each comprising a plurality of control temperatures associated with the one or more volumes of the thermal system; and communicating the one or more control temperature vectors to one or more thermal control units of the one or more volumes of the thermal system, to regulate temperature during an active cooling mode or an active heating mode of the one or more thermal control units;

wherein the method further comprises:

estimating a sequence of optimal temperature vectors, $\overline{T}_{o,c,n}$, in cool state c, at sample n, where n:[0,N), equal to the sequence of reference temperature vectors, $\overline{T}_{k,c,n}$, associated with the one or more of the plurality of states of the optimal path, calculated as a function of: a child state value vector, $\overline{s}_{k,c,n+1}$, of a plurality of $[0,V^J)$ child states, v, an action value vector, $\overline{q}_{u,k,c,n}$, associated with the transition to a plurality of $[0,V^J)$ child states, a time discount rate, γ, a density, V, and J volumes of the thermal system, wherein the resulting state value vector is selected to minimize a vector norm of the plurality of candidate state value vectors, according to:

$$\overline{T}_{O,c,n} = \overline{T}_{k,c,n} : \sum_{j=0}^{J-1}(q_{u,v,k,c,n}+\gamma s_{k,j,c,n+1}) = \min\left(\sum_{j=0}^{J-1}(q_{u,v,j,c,n}+\gamma s_{v,j,c,n+1})\right)\Bigg|_{\substack{v:[0,V^J)\\k:v\\j:[0,J)\\n:(N-1,0]}}$$

2. The processor-implemented method of claim 1, wherein the one or more thermal control units of the one or more volumes of the thermal system are associated with one or more HVAC units.

3. The processor-implemented method of claim 1, wherein the one or more thermal device properties includes at least one of: a temperature, a humidity, an energy consumption of an HVAC unit, or a power consumption of an HVAC unit, and wherein the thermal device properties are collected from one or more sensing devices.

4. The processor-implemented method of claim 1, wherein the one or more weather estimates includes at least one of: a temperature, a cloud cover, a humidity, or a solar irradiance.

5. The processor-implemented method of claim 1, wherein at least one of the one or more weather estimates is received from at least one of: one or more weather service providers, or one or more sensing devices associated with the surrounding environment of the thermal system.

6. The processor-implemented method of claim 1, wherein at least one of the one or more weather estimates is one of: a forecast weather estimate, an historical weather estimate, or an historical weather observation.

7. The processor-implemented method of claim 1, wherein each state of the plurality of states is associated with a respective temperature vector, the respective temperature vector comprising a plurality of temperatures associated with the one or more volumes of the thermal system, wherein each temperature of the plurality of temperatures is calculated as a function of at least one of: the one or more thermal device properties, or the one or more weather estimates.

8. The processor-implemented method of claim 1, wherein each state of the plurality of states is associated with a respective temperature vector that is calculated to define physically realizable transitions as a function of at least one of: an energy, a power, a current, a temperature, a financial resource, a social resource, a resource availability, or a time.

9. The processor-implemented method of claim 1, wherein each state of the plurality of states is associated with a respective time that is defined at discrete constant or variable time intervals originating at the first time and extending over the duration of time.

10. The processor-implemented method of claim 1, wherein the plurality of states and associated transitions are contained in a collection, wherein the collection is a representation of at least one of: a hypercube, a tree, or a mesh.

11. The processor-implemented method of claim 1, wherein two or more states of the plurality of states associated with the same respective time are merged into a single state if a vector norm of a difference between the respective temperature vectors associated with the two or more states is less than a temperature resolution.

12. The processor-implemented method of claim 1, wherein the one or more constraint properties includes at least one of: an energy, a power, a current, a temperature, a financial resource, a social resource, a resource availability, or a time.

13. The processor-implemented method of claim 12, wherein the one or more constraint properties includes one or more effective temperature vectors, the effective temperature vector comprising a plurality of effective temperatures associated with the one or more volumes of the thermal system, wherein the effective temperature represents an estimate of a temperature that minimizes energy consumption due to active cooling or heating while maintaining comfort.

14. The processor-implemented method of claim 1, wherein each transition of the respective plurality of transitions is associated with a respective action value vector, the respective action value vector comprising a plurality of action values associated with the one or more volumes of the thermal system, wherein each respective action value vector represents an immediate cost of transitioning from a specific state to a child state calculated as a function of at least one of: an energy, a power, a current, a temperature, a financial resource, a social resource, a resource availability, or a time.

15. The processor-implemented method of claim 14, wherein each state of the plurality of states is associated with a respective state value vector, the respective state value vector comprising a plurality of state values associated with the one or more volumes of the thermal system, wherein each respective state value vector represents the cost of being in a specific state calculated as a function of at least one of: one or more state value vectors associated with one or more child states, one or more action value vectors associated with transitions to one or more child states, or a time discount rate.

16. The processor-implemented method of claim 15, wherein the selecting an optimal path comprises selecting transitions of the respective plurality of transitions to minimize a vector norm of a plurality of candidate state value vectors, where each candidate state value vector is calculated as a function of at least one of: a state value vector associated with a child state, an action value vector associated with a transition to a child state, or a time discount rate.

17. The processor-implemented method of claim 1, wherein the cost function is a function of at least one of: an energy, a power, a current, a temperature, a financial resource, a social resource, a resource availability, or a time.

18. The processor-implemented method of claim 1, wherein the calculating the one or more control temperature vectors is a function of at least one of: the respective temperature vectors associated with the one or more of the plurality of states of the optimal path, or the one or more constraint properties.

19. The processor-implemented method of claim 1, wherein the method is implemented iteratively, asynchronously or synchronously, at a constant or variable frequency rate.

20. A processor-implemented method for adaptive temperature control of a Heating, Ventilation, and Air Conditioning (HVAC) unit of thermal system, the method comprising:

receiving, at a comfort agent system, one or more thermal device properties associated with one or more volumes of the thermal system;

receiving, at the comfort agent system, one or more weather estimates associated with a surrounding environment of the thermal system;

determining a root state associated with a temperature vector comprising a plurality of temperatures associated with the one or more volumes of the thermal system, and the root state being associated with a state value vector comprising a plurality of state values that represent a cost of being in a specific state, a first time, and a plurality of transitions, each transition associated with an action value vector comprising a plurality of action values which represent the immediate cost of transitioning from a specific state to a child state;

calculating a plurality of states, including the root state, originating at the first time and extending over a duration of time, each state of the plurality of states being associated with a respective temperature vector, a respective state value vector comprising a plurality of state values which represent the cost of being in a specific state, a respective time, and a respective plurality of transitions, each transition associated with an action value vector comprising a plurality of action values which represent the immediate cost of transitioning from a specific state to a child state;

determining one or more constraint properties, wherein the one or more constraint properties include at least one of: an energy, a power, a current, a temperature, a financial resource, a social resource, a resource availability, or a time, the one or more constraint properties being associated with a time originating at the first time and extending over the duration of time;

selecting an optimal path comprising one or more of the plurality of states, the optimal path: (1) originating with the root state; (2) including transitions of the respective plurality of transitions, (3) defining a contiguous sequence of one or more of the plurality of states extending over the duration of time, each state in the sequence of one or more of the plurality of states being associated with a unique respective time; and (4) minimizing the cost associated with the optimal path determined by a cost function, wherein the cost function is a function of at least one of: an energy, a power, a current, a temperature, a financial resource, a social resource, a resource availability, or a time;

calculating one or more control temperature vectors each comprising a plurality of control temperatures associated with the one or more volumes of the thermal system, based on at least one of: the one or more respective temperature vectors associated with the one or more of the plurality of states of the optimal path, or the one or more constraint properties; and communicating the one or more control temperature vectors to one or more thermal control units of the one or more volumes of the thermal system, to regulate temperature during an active cooling mode or an active heating mode of the one or more thermal control units, wherein each thermal control unit is associated with one or more (HVAC) units;

wherein the method further comprises:

estimating a sequence of optimal temperature vectors, $T_{o,c,n}$, in cool state c, at sample n, where n:[0,N), equal to the sequence of reference temperature vectors, $\overline{T}_{k,c,n}$, associated with the one or more of the plurality of states of the optimal path, calculated as a function of: a child state value vector, $\overline{s}_{k,c,n+1}$, of a plurality of $[0,V^J)$ child states, v, an action value vector, $\overline{q}_{u,k,c,n}$, associated with the transition to a plurality of $[0,V^J)$ child states, a time discount rate, γ, a density, V, and J volumes of the thermal system, wherein the resulting state value vector is selected to minimize a vector norm of the plurality of candidate state value vectors, according to:

$$T_{O,c,n} = \overline{T}_{k,c,n} : \sum_{j=0}^{J-1}(q_{u,v,k,c,n} + \gamma s_{k,j,c,n+1}) = \min\left(\sum_{j=0}^{J-1}(q_{u,v,j,c,n} + \gamma s_{v,j,c,n+1})\right)\Bigg|_{\substack{v:[0,V^J) \\ k:v \\ j:[0,J) \\ n:(N-1,0]}}$$

21. The processor-implemented method of claim 20, wherein each state of the plurality of states is associated with a respective temperature vector, the respective temperature vector comprising a plurality of temperatures associated with the one or more volumes of the thermal system, wherein each temperature of the plurality of respective temperatures is calculated as a function of at least one of: the one or more thermal device properties, or one or more weather estimates.

22. The processor-implemented method of claim 20, wherein each state of the plurality of states is associated with a respective temperature vector that is calculated to define physically realizable transitions as a function of at least one of: an energy, a power, a current, a temperature, a financial resource, a social resource, a resource availability, or a time.

23. The processor-implemented method of claim 20, wherein the selecting an optimal path comprises selecting transitions of the respective plurality of transitions to minimize a vector norm of a plurality of candidate state value vectors, where each candidate state value vector is calculated as a function of at least one of: a state value vector associated with a child state, an action value vector associated with to a transition a child state, or a time discount rate.

24. The processor-implemented method of claim 20, wherein the state value vector, $\overline{s}_{u,c,n}$, associated with a specific state, u, in cool state c, at sample n, where n:[0,N), is calculated as a function of: a child state value vector, $\overline{s}_{k,c,n-1}$, of a plurality of $[0,V^J)$ child states, v, an action value vector, $\overline{q}_{u,k,c,n}$, associated with the transition to a plurality of $[0,V^J)$ child states, a time discount rate, γ, a density, V, and J volumes of the thermal system, wherein the resulting state value vector is selected to minimize a vector norm of the plurality of candidate state value vectors, according to:

$$\bar{s}_{u,c,n} = \bar{q}_{u,k,c,n} + \gamma \bar{s}_{k,c,n+1} : \sum_{j=0}^{J-1} (q_{u,v,k,c,n} + \gamma s_{k,j,c,n+1}) = \min\left(\sum_{j=0}^{J-1} (q_{u,v,j,c,n} + \gamma s_{v,j,c,n+1})\right)\bigg|_{\substack{v:[0,V^J) \\ k:v \\ j:[0,J) \\ n:(N-1,0]}}.$$

25. The processor-implemented method of claim 20, wherein the action value vector, $\bar{q}_{u,v,c,n}$, associated with the transition from a specific state, u, to a child state, v, in cool state c, at sample n, where n: [0,N), with a sample period, $T_S$, a density, V, and J volumes of the thermal system, is selected from a plurality of $V^J$ quantized vectors, $\bar{E}_{u,v,c,n}$, as a function of at least one of: an available energy vector, $\bar{E}_{M,c}$, or an available power vector, $\bar{P}_{M,c}$, according to:

$$\bar{q}_{u,v,c,n} = \bar{E}_{u,v,c,n} = \left(\frac{v}{V-1}\right)\bar{P}_{M,c}T_S = \left(\frac{v}{V-1}\right)\bar{E}_{M,c}\bigg|_{\substack{v:[0,V^J) \\ n:[0,N-1)}}.$$

* * * * *